US007659117B2

(12) United States Patent
Laus et al.

(10) Patent No.: US 7,659,117 B2
(45) Date of Patent: Feb. 9, 2010

(54) COMPOSITIONS AND METHODS FOR DENDRITIC CELL-BASED IMMUNOTHERAPY

(75) Inventors: Reiner Laus, Bellevue, WA (US); Damir Vidovic, Bellevue, WA (US); Thomas Graddis, Seattle, WA (US)

(73) Assignee: Dendreon Corporation, Seattle, WA (US)

( * ) Notice: Subject to any disclaimer, the term of this patent is extended or adjusted under 35 U.S.C. 154(b) by 452 days.

(21) Appl. No.: 11/144,912

(22) Filed: Jun. 3, 2005

(65) Prior Publication Data

US 2005/0232932 A1  Oct. 20, 2005

Related U.S. Application Data

(63) Continuation of application No. 09/821,883, filed on Mar. 30, 2001, now Pat. No. 7,060,279.

(60) Provisional application No. 60/193,504, filed on Mar. 30, 2000.

(51) Int. Cl.
C12N 5/06 (2006.01)
(52) U.S. Cl. .................. 435/355; 435/372; 530/300; 530/350
(58) Field of Classification Search .............. 435/372, 435/355; 530/300, 350
See application file for complete search history.

(56) References Cited

U.S. PATENT DOCUMENTS

| 4,399,216 | A | 8/1983 | Axel et al. |
| 5,846,538 | A | 12/1998 | Cheever et al. |
| 6,080,409 | A | 6/2000 | Laus et al. |
| 6,406,681 | B1 | 6/2002 | Adjei et al. |
| 6,544,518 | B1 | 4/2003 | Friede et al. |

OTHER PUBLICATIONS

Kawashima et al. (Cancer Res. Jan. 15, 1999; 59 (2): 431-435).*
Scott et al. (Mol. Cell. Biol. Apr. 1993; 13 (4): 2247-2257).*
Kwong et al. (Mol. Carcinog. Oct. 1998; 23 (2): 62-68).*
Baxevanis et al. (Cancer Immunol. Immunother. 2006; 55: 85-95).*
Adnane, J., et al., Oncogene, 4:1389-1395, (1989).
Akiyama, T., et al., Science, 232:1644-1646, (1986).
Bakker, A., et al., The Journal of Experimental Medicine, 179:1005-1009, (1994).
Beckmann, M., et al., Eur. J. Cancer, 28:322-326, (1992).
Burke, C.L., et al., Oncogene, 14:687-696, (1997).
Chen, CH., et al., J. Biomed Sci., 5:231-252, (1998).
Coulie, P., et al., J. Exp. Med., 180:35-42, (1994).
Coussens, L., et al., Science, 230:1132-1139, (1985).
Cresswell, P., Annu. Rev. Immunol., 12:259-293, (1994).
Czerniecki, B., et al., J. Immunol. 159:3823-3837, (1997).
Di Fiore, P., et al., Science, 237:178-182, (1987).
Disis, M.L., et al., Adv. Cancer Res., 71:343-371, (1997).
Engelhard, E., et al., Proc. Nat. Acad. Sci., 91:3224-3227, (1994).
Fendly, B.M., et al., J. Biol. Response Mod., 9(5):449-455, (1990).
Feinmesser, R.L., et al., Oncogene, 12(12):2725-2730, (1996).
Foy, T.M., et al., Semin Oncol., 29(3 Suppl. 11):53-61, (2002).
Foy, T.M., et al., Vaccine, 29(17-19):2598-2606, (2001).
Germain, R., Ann. NY Acad. Sci., 754:114-125, (1995).
Gotch, F., et al., Nature, 326:881-882, (1987).
Greenberg, P., Adv. Immunol., 49:281-355, (1991).
Heemels M., et al., Annu. Rev. Biochem., 64:463-491, (1995).
Hudziak, R., et al., Proc. Natl. Acad. Sci. USA, 84:7159-7163, (1987).
Inaba, K., et al., J. Exp. Med., 172(2):631-640, (1990).
Jameson, S., et al., J. Exp. Med., 177:1541-1550, (1993).
Kapitanovic, S., et al., Gastroenterology, 112:1103-1113, (1997).
Kawakami, Y., et al., Proc. Natl. Acad. Sci., 91:3515-3519, (1994).
Keown, W., et al., Methods in Enzymology, 185:527-537, (1990).
Kruisbeek, M., in Coligan et al., (eds.) Current Protocols in Immunology, Wiley, New York NY, 3.14.1-3.14.11, (1997).
van Lieshout, E.M., et al., Jpn. J. Cancer Res., 90(1):81-85 (1999).
Mitchell, D.A., et al., Eur. J. Immunol., 28(6):1923-1933, (1998).
Muller, W., et al., Cell, 54:105-115, (1988).
Ossevoort, M.A., et al., J. Immunother. Emphasis Tumor Immunol., 18(2):86-94, (1995).
Paik, S.M., et al., Proc. Am. Assoc. Cancer Res., 32:291, (1991).
Pietras, R., et al., Oncogene, 10:2435-1446, (1995).
Pucetti, P., et al., Eur. J. Immunol., 24(6):1446-1452, (1994).
Ridge, J., et al., Nature, 393:474-478, (1998).
Rieser, C., et al., Urol. Int., 63(3):151-159, (1999).
Saffari, B., et al., Cancer Research, 55:5693-5698, (1995).
Schechtman, D., et al., Parasite Immunol., 23(4):213-217, (2001).
Schirmbeck, R., et al., Eur. J. Immunol., 23:1528-1534, (1993).
Shimizu, K., et al., Cancer Res., 61(6):2618-2624, (2001).
Slamon, D., et al., Science, 235:177-182, (1987).
Slamon, D., et al., Science, 244:707-712, (1989).
Sorkin, A., et al., Oncogene, 8(11):3021-3028, (1993).
Steinman, R.M., Ann. Rev. Immunol., 9:271-296, (1991).
Tanaka, Y., et al., J. Immunol., 147:3646-3652, (1991).
Timmerman, J.M., et al., J. Immunol., 164(9):4797-4803, (2000).
Toes, R.E., et al., J. Immunol., 160(9):4449-4456, (1998).
Toes, R.E.M., et al., Proc Natl. Acad. Sci. USA, 93:7855-7860, (1996).
Tsai, C.M., et al., J. Natl. Cancer Inst., 85:897-901, (1993).

(Continued)

Primary Examiner—Stephen L Rawlings
(74) Attorney, Agent, or Firm—Kim & Spalding LLP; Peter J. Dehlinger; Susan J. Myers Fitch

(57) ABSTRACT

Disclosed are immunostimulatory fusion proteins and methods for generating protective DC-induced, T cell-mediated immune responses in vitro and in vivo. The immunostimulatory fusion proteins comprise a polypeptide antigen component and an immunostimulatory component derived from the intracellular domain of the HER-2 protein. Also disclosed are immunostimulatory compositions comprising dendritic cells pulsed with such an immunostimulatory fusion protein and methods for immunotherapy using the compositions.

3 Claims, 4 Drawing Sheets

OTHER PUBLICATIONS

Tsai, C.M., et al., J. Natl. Cancer Inst., 87:682-684, (1995).
Tuzi, N.L., et al., Biochem Soc. Trans., 16(5):675-677, (1988).
Vidovic, D., et al., Int. J. Cancer, 102:660-664, (2002).
Wada, H., et al., Proc. Natl. Acad. Sci. USA, 94(23):12557-12561, (1997).
Wadhwa, M., et al., Clin. Cancer Res., 5(6):1353-1361, (1999).
Wang, M., et al., J. Immunol., 154:4685-4692, (1995).
Wright, C., et al., Br. J. Cancer, 65:118-121, (1992).
Yu, D., et al., Oncogene, 6:1991-1996, (1991).
Yu, D. et al., Cancer Res., 53:891-898, (1993).
Zeillinger, R., et al., Oncogene, 4:109-114, (1989).
Zhau, H., et al., Prostate, 28:73-83, (1996).
Abbas, A. K. et al., *Cellular and Molecular Immunology Textbook*, W.B. Saunders Company, Saunders Text and Review Series, A Division of Harcourt Brace & Company, pp. 116-123 (Section II), 130-134 (Section II), 394-399 (Section IV), 401-405 (Chapter 18) (1997).
Robinson, Harriet L. et al. "The Scientific Future of DNA for Immunization", *A Report from The American Academy of Microbiology*, pp. 1-31 (1997).

* cited by examiner

COMPOSITIONS AND METHODS FOR DENDRITIC CELL-BASED IMMUNOTHERAPY

This application is a continuation of U.S. Ser. No. 09/821,883 filed Mar. 20, 2001, issued as U.S. Pat. No. 7,060,279, which claims the benefit of U.S. Provisional Application No. 60/193,504, filed Mar. 30, 2000, both of which are incorporated by reference herein in their entirety.

REFERENCE TO SEQUENCE LISTING, TABLE OR COMPUTER PROGRAM

A "Sequence Listing" has been submitted with this application in the form of a text file, created 7 May 2009, and named "57636-8022.US01 SEQLIST" (64,704 bytes), the contents of which are incorporated herein by reference in their entirety.

FIELD OF THE INVENTION

The present invention relates to an immunostimulatory fusion protein comprising a polypeptide antigen sequence component and a sequence component derived from the intracellular domain of the HER-2 protein which is effective to generate a protective DC-induced, T cell-mediated immune response against the polypeptide antigen; dendritic cells treated with such a composition and methods for immunotherapy using the fusion protein.

BACKGROUND OF THE INVENTION

The HER-2/erbB-2 (also called neu) gene encodes a transmembrane glycoprotein of Mr 185,000 (p185) possessing intrinsic tyrosine kinase activity (Akiyama et al., 1986, *Science* 232: 1644) and displaying extensive homology to the epidermal growth factor (EGF) receptor (Coussens et al., 1985, *Science* 230: 1132).

Several lines of evidence suggest a link between the amplification of HER-2 and neoplastic transformation. Amplification and overexpression of the HER-2 proto-oncogene occurred in human breast and ovarian cancers and correlated with both poor prognosis and decreased survival in patients (Slamon et al., 1987, *Science* 235: 177; Slamon et al., 1989, *Science* 244: 707).

In experimental systems, tumor antigen specific cytotoxic T lymphocytes (CTL) are the most powerful immunological mechanism for the elimination of tumors. (Greenberg, 1991, *Adv. Immunol.* 49: 281). Therefore, tumor specific antigens (Ag) recognized by CTL are likely to function as tumor rejection Ag, capable of inducing protective immunity in vivo.

CTL recognize class I molecules containing peptidic fragments of intracellular proteins that have been transported into endoplasmic reticulum prior to their transfer to the MHC molecule (Germain, 1995, *Ann. NY Acad. Sci.* 754:114; Heemels & Ploegh, 1995, *Annu. Rev. Biochem.* 64:463), while the bulk of class II complexed peptides presented to Th cells are degradation products of exogenous or cell surface proteins that enter the biosynthetic pathway of class II molecules via endocytosis and a subsequent fusion with lysosomes (Cresswell, 1994, *Annu. Rev. Immunol.* 12: 259). CTL are induced when a protein enters the major histocompatibility complex class I ("MHC I" or "class I") pathway of antigen processing. To enter this pathway the protein must be present in the cytosol of an antigen presenting cell (APC). There it is degraded into peptides which are then transported into the endoplasmic reticulum, where they associate with HLA class I molecules. These peptides are then displayed together with the class I molecules on the cell surface and can serve as an inducer and target of class I restricted antigen-specific CTL (Rothbard et al., 1987, *Nature* 326: 881).

The priming of an immune response expands and activates "naive" lymphocytes, i.e., those that have not previously seen a given immunogen such that they become "effector" cells that actively respond. Each naive cell has the potential for seeing one and only one antigenic epitope, a situation analogous to a key fitting into a lock. Only those cells that recognize their cognate epitope become effector cells.

T-cells can be of the "helper" or "cytotoxic" type. Helper T cells secrete growth factors for lymphoid cells that stimulate the activation and function of B and T cells. The cytotoxic T cells recognize and either directly, or indirectly, kill cells that express a particular antigen. Like B cells, each T cell has receptors specific for one and only one antigenic epitope. T cell receptors recognize fragments of proteins that are displayed on the cell surface by major histocompatibility complexes (MHC). The in vivo induction of CTL has typically been accomplished by immunization with live virus or cells (Tanaka, et al., *J. Immunol.*, (1991), 147, 3646-52, Wang, et al., *J. Immunol.*, (1995), 4685-4692). A characteristic of DC, a potent subset of APC, is their ability to trigger in vivo responses of naive $CD8^+$ cytotoxic T-lymphocytes (CTL), after being pulsed with antigen (Ridge et al. 1998 *Nature* 393:474).

Besides their immature (resting or precursor) form, DC exist in two mature states: activated and superactivated. Activated DC can stimulate $CD4^+$ T helper cells, but not $CD8^+$ cytotoxic T cells (CTL), while superactivated DC posses the ability to stimulate $CD8^+$ CTL.

Although tumor cells may express protein antigens that are recognized as foreign by the subject, and immune surveillance may limit the growth and spread of some types of tumors, the immune system does not always protect the subject from lethal human cancers. Such tumors may overwhelm the immune system due to rapid growth and spread and/or the tumor cells may evade immune destruction. Proposed mechanisms for such evasion include, but are not limited to, (1) down-regulation of Class I MHC antigens on the surface of tumor cells resulting in little or no complexing of processed tumor peptide antigens with Class I MHC as required for recognition by cytotoxic T lymphocytes (CTL), (2) a lack of activation of CTL due to little or no expression of Class II MHC molecules by tumor cells such that they cannot directly activate tumor-specific CD4+ helper T cells (which produce signals likely to be needed for CTL activity), (3) a lack of co-stimulation cell surface markers that provide secondary signals for activation of CD4+ helper T cells, and (4) factors produced by tumor cells that suppress anti-tumor responses, such as fas-ligand (Abbas, A. K. et al., Eds., CELLULAR AND MOLECULAR IMMUNOLOGY, $3^{rd}$ edition, W.B. Saunders Co., 394-405, 1997).

It is therefore desirable to provide a means for eliciting CTL responses against tumor-specific proteins. CTL can be induced either in vivo with vaccines or can be generated in vitro and then be re-infused into the tumor-bearing organism.

SUMMARY OF THE INVENTION

The invention is directed to an immunostimulatory fusion protein which includes a polypeptide or protein antigen sequence component and a sequence component derived from the intracellular domain of the HER-2 protein and is effective to elicit an immune response to the polypeptide or protein antigen sequence component of the fusion protein.

In one aspect, the HER-2 intracellular domain sequence component of the immunostimulatory fusion protein has the sequence presented as SEQ. ID. NO: 25.

In another aspect, the polypeptide or protein component is associated with tumor cells or the causative agent of an infectious disease.

In general, the immunostimulatory fusion protein is produced by translation of a continuous nucleic acid coding sequence. However, the fusion protein may also be produced by chemical coupling.

In one preferred embodiment, the polypeptide or protein component of the fusion protein is the mature HER-2 membrane distal extracellular domain sequence presented as SEQ. ID. NO: 23. Examples of such fusion proteins and the associated amino acid sequences are: HER500 (SEQ ID NO: 1), HER500.hGM-CSF (SEQ ID NO: 2), HER500* (SEQ ID NO:3) and HER500*.rGM-CSF (SEQ ID NO: 4).

The invention provides an immunostimulatory fusion protein composition which can mediate a dendritic cell-induced, T cell-mediated immune response.

In one aspect, the immunostimulatory fusion protein composition comprises a polypeptide or protein antigen sequence component and a sequence component derived from the intracellular domain of the HER-2 protein.

In a related aspect, the immunostimulatory fusion protein composition comprises dendritic cells activated by in vitro exposure to an immunostimulatory fusion protein of the invention alone, or in combination with the immunostimulatory fusion protein.

The invention also provides a method of producing superactivated DC, by exposing DC to an immunostimulatory fusion protein of the invention, in a manner effective to result in an acellular immune response to the polypeptide or protein antigen sequence component of the fusion protein. In practicing the method, DC may be exposed to immunostimulatory fusion protein in vitro or in vivo.

The invention provides methods, and compositions, for use immunotherapy of primary or metastatic cancers that are associated with a particular antigen. DC's are obtained from a human donor, exposed to an immunostimulatory fusion protein of the invention in a manner and for a time effective to result in antigen-loaded superactivated DC. The latter are then administered to a subject who has a cancer associated with expression of the polypeptide or protein component of the immunostimulatory fusion protein, resulting in an immunotherapeutic growth inhibiting response against the primary or metastatic cancer or tumor. In such cases, administration of such superactivated DC may be carried out in combination with co-administration of an immunostimulatory fusion protein to the patient.

In another related approach, the invention provides a method of treating cancer where the cancer is associated with the expression of a particular antigen, by administering an immunostimulatory fusion protein of the invention to a patient diagnosed with the cancer in a manner effective to result in an immune response to the polypeptide or protein antigen sequence component of the fusion protein.

In one exemplary embodiment of these aspects of the invention, the cancer is breast carcinoma, ovarian cancer or colon cancer and the polypeptide or protein antigen sequence component of the immunostimulatory fusion protein is the mature HER-2 membrane distal extracellular domain sequence presented as SEQ. ID. NO: 23.

DETAILED DESCRIPTION OF THE INVENTION

I. Definitions

Figure 1:
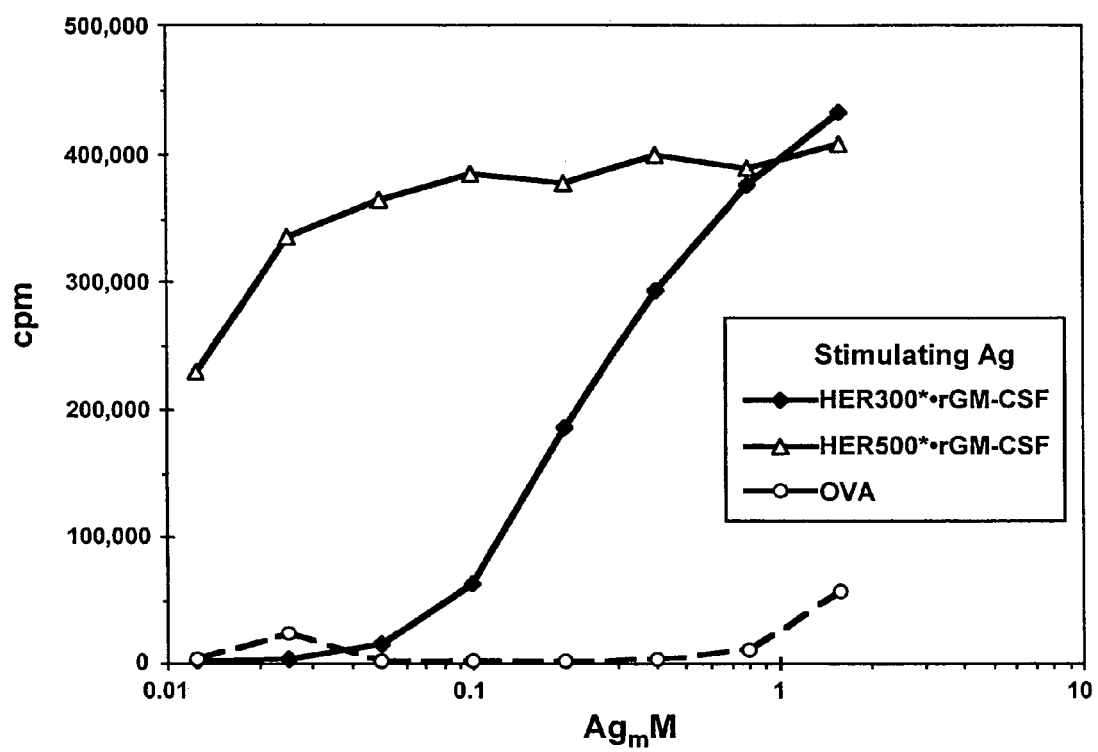
FIG. 1 shows the response of the interleukin-2 (IL-2) secreting mouse MHC class I dependent $CD8^+$ T cell hybridoma, B3Z [specific for the chicken ovalbumin "OVA" derived immunodominant peptide SIINFEKL (SEQ ID NO:22) (Jameson et al., 1993, *J. Exp. Med.* 177:1541)], to various antigens (Ag) presented by syngeneic superactivated dendritic cells (DC). CPM refers to counts per minute; Δcpm refers to a difference between the absolute cpm for a given test group minus the background cpm value obtained in the absence of the soluble Ag (in the experiment shown the latter was 9,581). The composition of the various antigens is indicated in the figure is described below.

Unless otherwise indicated, the terms below have the following meanings:

As used herein, "presentation of soluble protein antigens in the context of major histocompatibility complex class I molecules (MHC I)" means the soluble protein antigen or fragments thereof, are displayed together with major histocompatibility complex class I molecules on the cell surface and can serve as an inducer and target of class I restricted antigen-specific CTL.

As used herein, the term "pulse" means exposure of APC to antigen for a time sufficient to promote presentation of that antigen on the surface of the APC.

As used herein, the term "modified antigen presenting cells" (modified APC) or "modified dendritic cells" (modified DC) refers to a population of APC or DC, respectively, which have been treated (pulsed) ex vivo in manner effective to result in an enhanced ability to present antigen in the context of MHC class I relative to APC or DC which have not been so modified.

The term "more effectively" when used herein relative to the presentation of soluble proteins antigens means at least a 2-fold increase in the magnitude of detectable T cell response following presentation of a soluble protein antigen by APC. For example, this means that at least a 2-fold increase in the magnitude of T cell response is detected following presentation of a given antigen by a designated number of APC relative to magnitude of T cell response obtained when a different or modified antigen is presented by the same number of APC under the same culture conditions and at an equimolar Ag concentration.

As used herein, "antigen presenting cells" (APC) are any cells which, after being pulsed with Ag, can activate T-lymphocytes.

As used herein, "dendritic cells", or "DC", are the most potent subset of APCs that are typically large veiled cells which extend dendrites when cultured in vitro.

As used herein, "activated DC" are mature DC that can stimulate CD4+ helper T cells, but not $CD8^+$ cytotoxic T cells (CTL).

As used herein, "superactivated DC" are mature DC that can stimulate $CD8^+$ cytotoxic T cells (CTL).

As used herein, the term "allostimulatory" means capable of stimulating allogeneic T cells due to differences in MHC molecules expressed on the cell surface.

An "antigen" or "Ag" refers to a substance that reacts alone or in the context of MHC molecules with the products of an immune response (e.g., antibodies, T-cell receptors) which have been stimulated by a specific immunogen. Antigens therefore include the specific immunogens giving rise to the response (e.g., antigenic peptides, proteins or polysaccharides) as well as the entities containing or expressing the specific immunogens (e.g., viruses, bacteria, etc.).

As used herein, "immunogen" refers to a substance that is able to stimulate or induce a humoral antibody and/or cell-mediated immune response.

"Ag-loaded DC", include DC and various types of PBMC including professional APC and monocytes/macrophages, which have been exposed to an antigen and activated by the Ag. DC may become Ag-loaded in vitro, e.g., by culture ex vivo in the presence of a tumor Ag, or in vivo by exposure to a tumor antigen.

As used herein, the term "superactivated dendritic cell" refers to DC or DC precursors which have been treated ex vivo in such a way that they have an enhanced ability to present antigen in the context of MHC class I relative to the untreated DC.

As used herein, the terms "immunostimulatory fusion protein composition" and "antigenic fusion protein composition", may be used interchangeably and refer to a fusion protein of the invention which comprises an antigenic sequence component and a HER-2 intracellular domain sequence component alone and/or DC which have been exposed to such a fusion protein, as further described below.

As used herein, "OVA" refers to native ovalbumin; "*" refers to the immunodominant OVA-derived peptide SIINFEKL (SEQ ID NO:22); "HER500" refers to the recombinant fusion human HER-2 protein consisting of one half of its extracellular portion fused to the ¼ of its intracellular part; "HER500*" refers to the recombinant fusion protein made of HER500 and the immunodominant OVA-derived peptide SIINFEKL (SEQ ID NO:22) inserted between its extracellular and intracellular components; "HER500*.rGM-CSF" refers to the recombinant fusion protein composed of HER500* and rat granulocyte/macrophage colony-stimulating factor (GM-CSF); "HER500.hGM-CSF" refers to the recombinant fusion protein composed of HER500 and human GM-CSF; and "HER300*.rGM-CSF" refers to the recombinant fusion human HER-2 protein consisting of one half of its extracellular portion fused to the immunodominant OVA-derived peptide SIINFEKL (SEQ ID NO:22) and rat GM-CSF, as summarized below.

By "protective T cell mediated response" is meant the T cell activity that leads to a slowing or diminution of the growth of cancer cells or a solid tumor, or a reduction in the total number of cancer cells or total tumor burden.

By "cancer or tumor" cell is meant a cell that exhibits a loss of growth control and forms unusually large clones of cells. Tumor or cancer cells generally have lost contact inhibition and may be invasive and/or have the ability to metastasize.

"Tumor antigens" refer to Ag associated with a particular type of cancer or tumor, including tumor-associated Ag and tumor-specific Ag. Examples of tumor antigens are provided below in Section IIA.

As used herein, the term "improved therapeutic outcome" relative to a cancer patient refers to a slowing or diminution of the growth of cancer cells or a solid tumor, or a reduction in the total number of cancer cells or total tumor burden.

As used herein, the term "improved therapeutic outcome" relative to a subject diagnosed as having an infectious disease, refers to a slowing or diminution in the growth of the causative infectious agent within the subject and/or a decrease in, or elimination of, detectable symptoms typically associated with the particular infectious disease.

II. Immune Response to Soluble Polypeptide Antigens

In experimental systems, tumor antigen specific cytotoxic T lymphocytes (CTL) are the most powerful immunological mechanism for the elimination of tumors. CTL can be induced either in vivo with vaccines or can be generated in vitro and then be re-infused into the tumor-bearing organism. The in vivo induction of CTL is typically accomplished by immunization with live virus or cells (Tanaka, et al., *J. Immunol.*, (1991), 147, 3646-52, Wang, et al., *J. Immunol.*, (1995), 46854692).

With the exception of a few special viral proteins such as the SV40 large T antigen and the Hepatitis B surface antigen, injection of isolated or soluble proteins does not result in induction of CTL (Schirmbeck, et al., *Eur. J. Immunol.*, (1993), 23, 1528-34). CTL are induced when a protein enters the major histocompatibility complex class I ("MHC I" or "class I") pathway of antigen processing. To enter this pathway the protein must be present in the cytosol of an antigen presenting cell (APC). There it is degraded into peptides which are then transported into the endoplasmic reticulum, where they associate with HLA class I molecules. These peptides are then displayed together with the class I molecules on the cell surface and can serve as an inducer and target of class I restricted antigen-specific CTL. Physiologically, only proteins that are endogenously synthesized by the APC enter this pathway.

The priming of an immune response expands and activates "naive" lymphocytes, i.e., those that have not previously seen an immunogen to become "effector" cells that actively respond. Each naive cell has the potential for seeing one and only one antigenic epitope, a situation analogous to a key fitting into a lock. Only those cells that recognize their cognate epitope become effector cells.

T-cells can be of the "helper" or "cytotoxic" (cytotoxic) type. Helper T cells secrete growth factors for lymphoid cells that stimulate the activation and function of B and T cells. The cytotoxic T cells recognize and either directly, or indirectly, kill cells that express a particular antigen. Like B cells, each T cell has receptors specific for one and only one antigenic epitope. T cell receptors recognize fragments of proteins that are displayed on the cell surface by major histocompatibility complexes (MHC).

There are two different types of MHC proteins, Class I and Class II, both of which present proteolytically degraded fragments of proteins to T cells. Class I molecules which are expressed on most cells of the body and present fragments of endogenously synthesized proteins to cytotoxic T cells. Class II molecules which are expressed on specialized antigen presenting cells (APCs) such as macrophages, monocytes, dendritic cells and B cells present protein fragments to T helper cells. (Chen, C H and Wu, T C, *J Biomed Sci.*, 5(4):231-52 1998).

In most cases, Class I molecules present foreign proteins synthesized in a cell. For presentation by Class II, the foreign protein either can be synthesized in the cell or taken up by the cell from the outside (i.e., presented in the form of a free protein or peptide). If an antigen is synthesized in a cell and presented by both Class I and Class II molecules, both antibody producing B cells and cytotoxic T cells are produced. However, if an antigen originated outside of a cell and is expressed only by Class II, the specific immune response is largely limited to T helper cells and antibody production. [THE SCIENTIFIC FUTURE OF DNA FOR IMMUNIZATION, American Academy of Microbiology, Robinson, et al., Eds., 1-29, 1997]

Accordingly, the typical response to soluble protein antigens is a Class II mediated response. The present invention represents compositions and methods which allow soluble protein antigens to enter the Class I presentation pathway.

In addition, some progeny of antigen-stimulated T cells do not develop into effector cells, but become memory cells that are capable of surviving for long periods of time in the absence of additional antigenic challenge. Such memory cells are quiescent and do not produce effector molecules unless they are stimulated by antigen. (See, e.g., Abbas, A K et al., Eds. CELLULAR AND MOLECULAR IMMUNOLOGY, W.B. Saunders Co., pages 116-123; 130-134, 1997).

Naïve T cells (or T cells that have not been previously exposed to a given antigen) require only the correct MHC I-restricting molecule to survive, however to expand, they also must be exposed to antigen. In contrast, memory T cells have a lower functional activation threshold that facilitates secondary responses which are more rapid and stronger than that of naive T cells.

A. Polypeptide Antigens

The present invention is based on the discovery that immunostimulatory compositions comprising a polypeptide antigen component and a sequence component derived from the intracellular domain of the HER-2 protein are effective to generate a protective DC-induced, T cell-mediated immune response against the polypeptide antigen.

Polypeptide antigens of particular interest are those associated with cancer cells, tumors and/or infectious agents.

For example, "tumor-specific antigens" and "tumor-associated antigens" that are characteristic of a particular tissue type, including particular tumor tissues find utility in the immunostimulatory fusion proteins of the invention. Exemplary tumor antigens include, but are not limited to HER-2/neu; prostatic acid phosphate (PAP); MART-1 (associated with melanoma; Coulie, et al., *J. Exp. Med.* 180:35, 1994; Hawakami, et al., *PNAS* 91:3515, 1994; Bakker, et al., *J. Exp. Med.* 179:1005, 1994); the tumor rejection antigen precursors, MAGE, BAGE and GAGE; NY-ESO (cloned from an esophageal cancer); SART-3 (a squamous cell carcinoma antigen), immunoglobulin antigens specific to particular B-cell lymphomas, tumor-associated antigens such as carcinoembryonic antigen (CEA), p53, c-myc, neural cell adhesion molecule (N-CAM) and polymorphic epithelial mucin (PEM), in addition to any of a number of proteins expressed on tumor cells.

Also of interest are antigens specific to particular infectious agents, e.g., viral agents including, but not limited to human immunodeficiency virus (HIV), hepatitis B virus (HBV), influenza, human papilloma virus (HPV), foot and mouth (coxsackieviruses), the rabies virus, herpes simplex virus (HSV), and the causative agents of gastroenteritis, including rotaviruses, adenoviruses, caliciviruses, astroviruses and Norwalk virus; bacterial agents including, but not limited to *E. coli, Salmonella thyphimurium, Pseudomonas aeruginosa, Vibrio cholerae, Neisseria gonorrhoeae, Helicobacter pylori, Hemophilus influenzae, Shigella dysenteriae, Staphylococcus aureus, Mycobacterium tuberculosis* and *Streptococcus pneumoniae*, fungal agents and parasites such as *Giardia*.

HER-2, An Exemplary Antigen for Use in Immunostimulatory Fusion Proteins

Malignant tumors express a number of proteins including molecules belong to the group of transformation-related molecules such as the oncogene HER-2/Neu/ErbB-2.

Likewise, oncogene product peptide antigens have been identified that are common to specific tumor types. These polypeptides find use as reagents that can generally stimulate T-cell responses effective to react with tumors bearing such antigens. The oncogene product peptide antigen, HER-2/neu (Beckmann et al., *Eur. J. Cancer* 28:322, 1992) is associated with human breast and gynecological cancers.

The association of HER-2 overexpression in cancer cells with malignant phenotypes and chemoresistance is consistent with poor clinical outcome for patients with HER-2-overexpressing tumors. The following is a brief summary of HER-2 overexpression associated with various cancers:

Amplification and overexpression of the HER-2 gene is found in 25-30% of primary breast cancers and is associated with a poor clinical outcome. In vitro studies of HER-2 overexpression promoted down-regulation of the estrogen receptor (ER) in estrogen-dependent breast tumor cells (Pietras et al., 1995, *Oncogene* 10: 2435), consistent with clinical data that shows HER-2 overexpression is associated with the ER-negative phenotype (Zeillinger et al., 1989, *Oncogene* 4: 109; Adnane et al., 1989, *Oncogene* 4: 1389), and the failure of tamoxifen therapy in patients with HER-2 overexpression (Wright et al., 1992; *Br. J. Cancer* 65:118).

A study on colorectal cancer patients. demonstrated that the level of HER-2 expression correlated with the progression of colorectal cancer, the relapse-free period and postoperative survival time, and could serve as an independent prognostic factor in HER-2-positive colorectal cancers (Kapitanovic et al., 1997, *Gastroenterology* 112: 1103).

The expression of HER-2 protein has also been described as an independent prognostic indicator in ovarian (Slamon et al., 1989, *Science* 244: 707) and endometrial cancers (Saffari et al., 1995, *Cancer Res.* 55: 5693).

Overexpression of HER-2 in NIH/3T3 cells resulted in cellular transformation and tumor growth in athymic mice (Di Fiore et al., 1987, *Science* 237: 178; Hudziak et al., 1987, *Proc. Natl. Acad. Sci. USA* 84: 7159). Cellular and animal experiments have shown that the enhanced HER-2 tyrosine kinase activity increased the expression of malignant phenotypes (Hudziak et al., 1987, *Proc. Natl. Acad. Sci. USA* 84: 7159; Muller et al., 1988, *Cell* 54: 105; Yu & Hung, 1991, *Oncogene* 6:1991; Yu et al., 1993, *Cancer Res.* 53: 891; Zhau et al., 1996, *Prostate* 28: 73). Transgenic mice overexpressing activated c-neu oncogene driven by a mouse mammary tumor promoter, developed synchronously multiple mammary tumors involving the entire glands (Muller et al., 1988, *Cell* 54: 105).

Overexpression of HER-2 was also reported to induce resistance to chemotherapeutic drugs in NSCLC, gastric adenocarcinoma and breast cancers (Tsai et al., 1993, *J. Natl. Cancer Inst.* 85: 897; Tsai et al., 1995, *J. Natl. Cancer Inst.*

87: 682; Paik et al., 1991, *Proc. Am. Assoc. Cancer Res.* 32:291; Wright et al., 1992, *Br. J. Cancer* 65:118).

HER-2 peptide and polypeptide antigens can be isolated, synthesized or recombinantly expressed according to methods known in the art. The DNA coding sequence for HER-2/Neu/ErbB-2 may be found at sequence database GenBank™ Accession No. M11730 (human c-erb-B-2 mRNA).

Such isolated HER-2 antigens can be complexed with any of a number of molecules that enhance the immune response to the antigen, as discussed below, either chemically, or as fusion proteins produced recombinantly, according to methods well known in the art.

III. Immunostimulatory Fusion Proteins

The present invention is based on the discovery that immunostimulatory fusion proteins comprising a polypeptide antigen sequence component and a sequence component derived from the intracellular domain of the HER-2 protein are effective to generate a protective DC-induced, T cell-mediated protective immune response against the antigenic component of the fusion protein.

An exemplary intracellular domain of the HER-2 protein is presented herein, however it will be understood that shorter fragments of the exemplary sequence may also exhibit activity. Most importantly, a sequence component derived from the intracellular domain of the HER-2 protein has been demonstrated to contribute to the immunostimulatory activity of fusion proteins comprising such sequence components.

An immunostimulatory fusion protein construct of the invention may also include one or more sequence components selected from the group consisting of GM-CSF, a reporter sequence such as the OVA-derived octapeptide SIINFEKL ($OVA_{257-264}$) (SEQ ID NO:22), one or more peptide signal sequences and a synthetic purification tag, e.g., an added C-terminal amino acid sequence.

Exemplary immunostimulatory fusion protein constructs described herein have a 32 amino acid PAP signal sequence[1], a 3 amino acid mature PAP sequence[2], a 3 amino acid HER-2 signal sequence[3], and either a C-terminal amino acid purification tag sequence of 9 amino acid residues comprising three consecutive alanines and six consecutive histidines, or a C-terminal amino acid tag sequence of 15 amino acid residues comprising glycine, alanine, 4 consecutive prolines, three consecutive alanines, and six consecutive histidines and the features summarized in Table 1, below.

[1]32 amino acids corresponding to amino acids 1 to 32 of sequence database GenBank™ accession No. NM_001099
[2]3 amino acids corresponding to amino acids 33 to 35 of sequence database GenBank™ accession No. NM_001099
[3]3 amino acids corresponding to amino acids 19 to 21 of sequence database GenBank™ accession No. M11730

TABLE 1

Components Of Exemplary HER-2 Fusion Proteins.

| Construct | HER-2 extracellular sequence[4] | SIINFEKL ($OVA_{257-264}$) | HER-2 intracellular sequence[5] | GM-CSF |
|---|---|---|---|---|
| HER500 | + | − | + | — |
| HER500•hGM-CSF | + | − | + | 127 aa (human) |
| HER500* | + | + | + | — |
| HER500*•rGM-CSF | + | + | + | 127 aa (rat) |
| HER300*•rGM-CSF | + | + | − | 127 aa (rat) |

[4]289 amino acids corresponding to amino acids 22 to 310 of Genebank accession No. M11730
[5]217 amino acids corresponding to amino acids 1038 to 1254 of Genebank accession No. M11730

It will understood that a fusion protein comprising a polypeptide antigen sequence component and a sequence component derived from the intracellular domain of the HER-2 protein are alone effective to generate a protective DC-induced, T cell-mediated protective immune response against the antigenic component of the fusion protein.

Accordingly, the SIINFEKL (SEQ ID NO:22) ($OVA_{257-264}$) sequence, the PAP signal sequence, the mature PAP amino acid sequence, the HER-2 signal sequence, and the C-terminal peptide tag sequence set forth above are not necessary to generate such as response.

The immunostimulatory fusion proteins of the invention may be modified by joining them, either covalently or non-covalently, with a reporter molecule. A wide variety of reporter molecules are known in the art and the selection of the reporter determines the assay format. For example, as detailed in Example 1, the OVA-derived immunodominant octapeptide SIINFEKL (SEQ ID NO:22) ($OVA_{257-264}$) was incorporated into exemplary immunostimulatory HER-2 fusion constructs and antigen presentation of the constructs evaluated. Briefly, the IL-2 secreting mouse T cell hybridoma B3Z, which responds to SIINFEKL (SEQ ID NO:22) ($OVA_{257-264}$), when bound to mouse MHC class I, was stimulated with DC that were pre-pulsed with the HER-2 fusion constructs, and the magnitude of response evaluated by measuring [$^3$H]thymidine incorporation in proliferating IL-2 dependent cells, as an indicator of antigen presentation.

Additional examples of fusion proteins for use in practicing the invention include, but are not limited to those which include the sequence of a cancer antigen directly fused to the 217 amino acids of membrane distal intracellular HER-2 domain, without additional linker or signal peptide components. Examples of such fusion proteins include, but are not limited to: a fusion protein comprising 180 amino acids of the human autoimmunogenic cancer/testis antigen, NY-ESO-1 (amino acids 1 to 180 of sequence database GenBank™ Accession No. U87459), fused to the 217 amino acids of membrane distal intracellular HER-2 domain (amino acids 1038 to 1254 of sequence database GenBank™ Accession No. M 11730), presented herein as SEQ ID NO: 27, the coding sequence for which is presented as SEQ ID NO: 28); a fusion protein comprising 962 amino acids of the squamous cell carcinoma antigen, SART3- IC (amino acids 1 to 962 of sequence database GenBank™ Accession No. AB020880), fused to the 217 amino acids of membrane distal intracellular HER-2 domain (amino acids 1038 to 1254 of sequence database GenBank™ Accession No. M 11730), presented herein as SEQ ID NO: 29, the coding sequence for which is presented as SEQ ID NO: 30).

As known in the art, a recombinant polypeptide may also be produced as a fusion with a heterologous polypeptide, such as a signal sequence or other polypeptide having a specific cleavage site at the N-terminus of the mature protein or polypeptide. In general, the signal sequence is specific to the vector/host cell system used to express the recombinant protein.

Recombinant polypeptides or fusion proteins that include a tag sequence placed for example at the amino- or carboxyl-terminus of the polypeptide are also known in the art. The tag sequence enables the polypeptide to be readily detected using an antibody against the tag and facilitates affinity purification of the polypeptide.

Granulocyte-macrophage colony stimulating factor (GM-CSF), has been included in exemplary fusion constructs of the invention. GM-CSF, a glycoprotein with an apparent molecular weight of about 23-33,000 by SDS-PAGE, is a cytokine that has pleiotropic function both in hematopoiesis as well as in immunology. Human and rat GM-CSF have been shown to bind to cells of the monocyte-macrophage, neutrophil and eosinophil cell lineages. Binding of GM-CSF to high affinity receptors results in rapid internalization and degradation of GM-CSF (Metcalf and Nicola in THE HEMOPOETIC COLONY-STIMULATING FACTORS, Cambridge University Press, NY (1995)). The immunostimulatory effect of a polypeptide complex consisting essentially of GM-CSF and a polypeptide antigen is further described in U.S. Ser. No. 08/579,823 (allowed), expressly incorporated by reference herein. Both human and rat GM-CSF are synthesized with a 17-amino acid hydrophobic leader sequence that is proteolytically cleaved during secretion. The mature polypeptides are 127 amino acids in length, and the sequences may be found at GenBank Accession Nos. NM_000758 and U00620, respectively.

It will be appreciated that the HER-2 extracellular sequence[6] described herein is an example of an antigenic sequence that may be incorporated into an immunostimulatory fusion protein of the invention. It follows that any of a number of antigens associated with tumor cells or an infectious agent, may similarly be incorporated into an immunostimulatory fusion protein of the invention and be effective to generate a protective DC-induced, T cell-mediated protective immune response against the antigenic component of the fusion protein. Exemplary antigens are further described in Section IIA, above.

[6] 289 amino acids corresponding to amino acids 22 to 310 of sequence database GenBank™ accession No. M11730.

Exemplary HER-2 Antigen Compositions

An immunostimulatory fusion protein of the invention is made by chemical linkage of the antigenic sequence component to the sequence component derived from the intracellular domain of the HER-2 protein, or by expression of a recombinant and continuous nucleic acid coding sequence which is expressed as a fusion protein. Chemical linkage and/or recombinant protein expression may also be used to incorporate additional peptidic sequences into the fusion protein, e.g., a reporter sequence, a signal peptide sequence and/or a purification tag.

Exemplary human HER-2-derived recombinant and continuous nucleic acid coding sequences which have been expressed as fusion proteins are described below.

The exemplary HER500 construct (SEQ ID NO:6) was produced by expression of a coding sequence including in the 5' to 3' direction: the coding sequence for a 32 amino acid PAP signal sequence, the coding sequence for a 3 amino acid sequence of the mature PAP protein, an Ala Arg linker, the coding sequence for a 3 amino acid HER-2 signal sequence, the coding sequence for 289 amino acids of the mature HER-2 membrane distal extracellular domain, the coding sequence for 217 amino acids of the HER-2 membrane distal intracellular domain and the coding sequence for three consecutive alanines, and six consecutive histidines.

The exemplary HER500.hGM-CSF construct (SEQ ID NO:7) was produced by expression of a coding sequence including in the 0.5° to 3' direction: the coding sequence for a 32 amino acid PAP signal sequence, the coding sequence for a 3 amino acid sequence of the mature PAP protein, an Ala Arg linker, the coding sequence for a 3 amino acid HER-2 signal sequence, the coding sequence for 289 amino acids of mature HER-2 membrane distal extracellular domain, the coding sequence for 217 amino acids of the HER-2 membrane distal intracellular domain, an Ala Ala linker, the coding sequence for mature human GM-CSF (127 residues), and the coding sequence for glycine, alanine, four consecutive prolines, three consecutive alanines, and six consecutive histidines.

The exemplary HER500* construct (SEQ ID NO:8) was produced by expression of a coding sequence including in the 5' to 3' direction: the coding sequence for a 32 amino acid PAP signal sequence, the coding sequence for a 3 amino acid sequence of the mature PAP protein, an Ala Arg linker, the coding sequence for a 3 amino acid HER-2 signal sequence, the coding sequence for 289 amino acids of mature HER-2 membrane distal extracellular domain, an Ala linker, the coding sequence for the OVA- derived immunodominant octapeptide SIINFEKL ($OVA_{267-264}$)(SEQ ID NO:22), the coding sequence for 217 amino acids of the HER-2 membrane distal intracellular domain, three consecutive alanines, and six consecutive histidines.

The exemplary HER500*.rGM-CSF construct (SEQ ID NO:9) was produced by expression of a coding sequence including in the 5' to 3' direction: the coding sequence for a 32 amino acid PAP signal sequence, the coding sequence for a 3 amino acid sequence of the mature PAP protein, an Ala Arg linker, the coding sequence for a 3 amino acid HER-2 signal sequence, the coding sequence for 289 amino acids of mature HER-2 membrane distal extracellular domain, an Ala linker, the coding sequence for the OVA-derived immunodominant octapeptide SIINFEKL ($OVA_{257-264}$)(SEQ ID NO:22), the coding sequence for 217 amino acids of the HER-2 membrane distal intracellular domain, an Ala Ala linker, the coding sequence for mature rat GM-CSF (127 residues), and the coding sequence for glycine, alanine, four consecutive prolines, alanine, and six consecutive histidines.

The exemplary HER300*.rGM-CSF construct (SEQ ID NO:10) was produced by expression of a coding sequence including in the 5' to 3' direction: the coding sequence for a 32 amino acid PAP signal sequence, the coding sequence for a 3 amino acid sequence of the mature PAP protein, an Ala Arg linker, the coding sequence for a 3 amino acid HER-2 signal sequence, the coding sequence for 289 amino acids of mature HER-2 membrane distal extracellular domain, an Ala linker, the coding sequence for the OVA-derived immunodominant octapeptide SIINFEKL ($OVA_{257-264}$(SEQ ID NO:22), an Ala linker, the coding sequence for mature rat GM-CSF (127 residues), and the coding sequence for glycine, alanine, four consecutive prolines, alanine, and six consecutive histidines.

Methods for production of immunostimulatory fusion proteins by chemical linkage of an antigenic sequence to a sequence derived from the intracellular domain of the HER-2 protein include conventional coupling techniques known in the art. In constructs which also include one or more added peptidic sequences, chemical linkage is also accomplished using conventional coupling techniques known in the art. For example, the peptides can be coupled using a dehydrating agent such as dicyclohexyl-carbodiimide (DCCI) to form a peptide bond between the two peptides. Alternatively, linkages may be formed through sulfhydryl groups, epsilon amino groups, carboxyl groups or other reactive groups present in the polypeptides, using commercially available reagents. (Pierce Co., Rockford, Ill.);

IV. Production of Recombinant Fusion Proteins

The invention includes immunostimulatory fusion proteins produced using recombinant techniques. Such an immunostimulatory fusion protein may be produced by any of a number of methods routinely employed by those of skill in the art.

Unless otherwise indicated, all terms used herein have the same meaning as they would to one skilled in the relevant art. Practitioners are particularly directed to Sambrook et al. (1989) MOLECULAR CLONING: A LABORATORY MANUAL (Second Edition), Cold Spring Harbor Press, Plainview, N.Y. and Ausubel F M et al. (1989) CURRENT PROTOCOLS IN MOLECULAR BIOLOGY, John Wiley & Sons, New York, N.Y., for definitions and techniques routinely used by those of skill in the art.

The fusion proteins may be produced by culturing recombinant prokaryotic or eukaryotic host cells comprising nucleic acid sequences encoding the fusion protein under conditions promoting expression of the fusion proteins, followed by recovery of the fusion protein from the host cells or the cell culture medium.

The nucleic acid encoding sequence an immunostimulatory fusion protein of the invention is inserted into any one of a variety of expression vectors for expressing a polypeptide, as long as it is replicable and viable in the host. In general, the nucleic acid coding sequence is inserted into an appropriate restriction endonuclease site or site(s) using routine techniques. Such procedures and related sub-cloning procedures are deemed to be within the scope of those skilled in the art. The vector may comprise regulatory sequences, including for example, non-coding sequences, such as introns and control elements, i.e., promoter and terminator elements or 5' and/or 3' untranslated regions, effective for expression of the coding sequence in a suitable host and/or in a vector or host environment in which the immunostimulatory fusion protein coding sequence is not normally expressed, operably linked to the coding sequence. Large numbers of suitable vectors and promoters are known to those of skill in the art, are commercially available, examples of which are described in Sambrook, et al., (supra).

The present invention also relates to host cells which have been genetically engineered to contain a vector effective to express an immunostimulatory fusion protein of the invention by recombinant techniques. Host cells are genetically engineered (i.e., transduced, transformed or transfected) with an appropriate vector which may be, for example, a cloning or expression vector. The vector may take the form of a plasmid, a viral particle, a phage, etc. The culture conditions, such as temperature, pH and the like, are those routinely used for the host cell selected for expression, and will be apparent to those skilled in the art.

Methods of introducing nucleic acids into cells for expression of heterologous proteins are also known to the ordinarily skilled artisan. Examples include calcium phosphate transfection, DEAE-Dextran mediated transfection, electroporation, nuclear microinjection, bacterial protoplast fusion with intact cells, and the use of polycations, e.g., polybrene or polyornithine. General aspects of transformation involving mammalian cells have been described in U.S. Pat. No. 4,399, 216, and Keown et al., *Methods in Enzymology*, 185:527-537 (1990), both or which are expressly incorporated by reference herein.

Suitable host cells for cloning or expressing an immunostimulatory fusion protein of the invention include prokaryote, yeast, insect and higher eukaryotic cells. Suitable prokaryotes include but are not limited to eubacteria, such as gram-negative or gram-positive organisms, for example, *E. coli*.

Suitable host cells for the expression of a glycosylated immunostimulatory fusion protein of the invention are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. The selection of the appropriate host cell is deemed to be within the skill in the art.

A process for producing such an immunostimulatory fusion protein comprises culturing host cells under conditions suitable for expression of the fusion protein and recovering the fusion protein from the cell culture. In general, principles, protocols, and practical techniques for maximizing the productivity of cell cultures can be found in MAMMALIAN CELL BIOTECHNOLOGY: A PRACTICAL APPROACH, M. Butler, ed. (IRL Press, 1991) and Sambrook et al., supra. More specifically, techniques for expression in the Baculovirus system are described in Engelhard E K et al. *Proc. Nat. Acad. Sci.* 91:3224-3227, 1994, expressly incorporated by reference herein.

Host cells transformed with nucleotide sequences encoding an immunostimulatory fusion protein of the invention may be cultured under conditions suitable for the expression and recovery of the encoded protein from the cell culture. The protein produced by a recombinant cell may be secreted, membrane-bound, or contained intracellularly depending on the particular sequence and/or the vector used.

As understood by those of skill in the art, an expression vector containing a polynucleotide encoding an immunostimulatory fusion protein of the invention can be designed with signal sequences which direct secretion of the modified immunostimulatory fusion protein through a prokaryotic or eukaryotic cell membrane.

Example 1 details the construction of exemplary immunostimulatory HER-2 fusion proteins, the nucleic acid and deduced amino acid sequences of which are presented in Table 2.

Expression vectors comprising the coding sequence for various HER-2 fusion proteins were used to transfect mammalian 293-EBNA cells and insect SF21 cells. Once constructed, expressed and purified, HER2 fusion proteins containing either rat GM-CSF or human GM-CSF were tested for GM-CSF bioactivities in appropriate assays, routinely employed by those of skill in the art. Both insect and mammalian cell-derived fusion proteins exhibited GM-CSF activity, as evidenced by their ability to support growth of GM-CSF dependent cell lines. Similarly, the presence of HER-2 was verified using HER-2-specific monoclonal antibodies in both Western blot analysis and in an ELISA test, according to methods well-known in the art.

While the foregoing description describes particular embodiments of the present invention, it will be appreciated that persons skilled in the art can substitute the coding sequence for various antigens, and may use different vectors and cell lines for expression, according to known methods and thereby prepare immunostimulatory fusion protein compositions in accordance with the principles described herein.

Whether produced by chemical coupling or by expression of a continuos coding sequence as a recombinant fusion protein, DC may be exposed to an immunostimulatory fusion protein of the invention and be presented by such DC in the context of MHC I, resulting in a cellular immune response to the fusion protein.

V. Generation Of Activated Dendritic Cells (DC)

A. Isolation and Characterization of DC Precursors and DC

Human dendritic cell precursors (DC precursors) may be obtained from any of a number of sources including but not limited to peripheral blood, cord blood, bone marrow and lymphoid organs.

DC precursors isolated and enriched by any of a number of methods known in the art will result in a DC precursor population effective for carrying out the methods of the present invention.

In a preferred approach, DC precursors are obtained from peripheral blood. In this approach, peripheral blood mononuclear cells (PBMC) are collected from healthy donors by standard leukapheresis and DC precursors isolated, for example, by either a one-step or a successive two-step buoyant density centrifugation using buoyant density solution BDS 77 or BDS 77 and 65, respectively (Dendreon Corp.), as described in co-owned U.S. Ser. No. 60/168,991 (0021).

DC precursors may be obtained from a healthy subject or a subject known to be suffering from a disease associated with the expression of a particular antigen. Such DC precursors may be allogeneic or autologous.

Once DC precursors are obtained, they are cultured under appropriate conditions and for a time sufficient to expand the cell population and maintain the DC's in a state for optimal antigen uptake, processing and presentation.

In one preferred approach to culture of DC precursors, DC are generated from such DC precursors by culture ex vivo in serum free or protein-free medium for 40 hours, in the absence of exogenously added cytokines, as detailed in co-owned U.S. Ser. No. 60/158,618. Briefly, DC precursors are cultured in-teflon bags (American Fluoroseal) at a density of $1 \times 10^7$ per ml in Aim V medium supplemented with 2 mM glutamine in a humidified incubator at 37° C. under 5% $CO_2$ for 40 hours. During the culture period DC precursors are pulsed with Ag.

Preferred aspects of DC isolation and culture include the use of culture medium lacking exogenously supplied cytokines and culture under serum-free conditions in a manner effective to result in the generation of Ag-loaded superactivated DC.

The purity of DC in this fraction may be quantified using, for example, flow cytometry (i.e., FACS) analysis for phenotypic characterization as further described in co-owned U.S. Ser. No. 60/158,618, together with functional characterization. Cell surface phenotype analysis is carried out using samples consisting of approximately $1-3 \times 10^7$ cells, which are incubated in 10% normal mouse serum in PBS for 10 min., washed in PBS and resuspended in 250-750 μl PBS. The cell suspension is then dispensed at 30 μl/well into round-bottom 96-well plates. FITC-, PE-, and PerCP-conjugated mAb are added at 10 μl/well and cells are incubated for 20 min. in the dark on ice. Cells are then washed with 200 μl/well of PBS and resuspended in 400 μl/well in PBS, then analyzed by FACScan (Becton Dickinson) using cells labeled with isotype-matched control Ab as a negative control. Preferred functional characteristics of mature DCs include the acquisition of allostimulatory and Ag-presenting abilities.

Ag-loaded superactivated DCs have already processed an Ag and have the ability to present the Ag to the immune cells and quickly generate Ag-specific immune responses, e.g., CTL-mediated T cell responses to tumor antigens.

According to another aspect of the invention, DC's can be preserved by cryopreservation either before or after exposure to a HER-2 fusion protein of the invention. Exemplary methods for cryopreservation are further described in co-owned U.S. Ser. No. 60,168,991. For small scale cryopreservation, cells can be resuspended at $20\text{-}200 \times 10^6$ ml in precooled 5% human serum albumin (HAS) (Swiss Red Cross). An equal volume of 20% dimethylsulfoxide (DMSO) in the above HAS solution was then added dropwise. The mixture is aliquoted in cryovials at 1 ml/vial and frozen at −80° C. in a cryochamber (available from the company Nalgene™) overnight. The vials are transferred to a liquid nitrogen tank in the morning. For large scale cryopreservation, cells can be resuspended at $30\text{-}600 \times 10^6$/ml in AIM V. An equal volume of 20% AIM V is then added gradually. The mixture is frozen in freezing containers (Cryocyte, Baxter) at 20 ml/bag using a rate-controlled freezing system (available from the company Forma™).

B. Evaluation of Antigenicity of Fusion Proteins

An antigen presentation assay may be used to evaluate the antigen presenting ability of various immunostimulatory fusion proteins. An exemplary assay is described in Example 1, wherein the IL-2 secreting mouse T cell hybridoma B3Z, which responds to the mouse MHC class I ($H2\text{-}K^b$) bound OVA-derived peptide SIINFEKL (SEQ ID NO:22) ($OVA_{257-264}$; Jameson et al., 1993, *J. Exp. Med.* 177:1541), is stimulated with various DC that have been pre-pulsed with engineered HER-2 fusion proteins, and the magnitude of response is evaluated by measuring [3H]thymidine incorporation in proliferating IL-2 dependent cells.

The assay format described herein may be used to evaluate antigen presentation using a titration of the antigen together with a fixed number of APC.

B. In Vivo Assays in Animal Models

An immunostimulatory fusion protein of the invention may be evaluated in vivo in animal models. In such cases, pre-immunization of animals with the immunostimulatory fusion protein composition, or superactivated DC treated ex vivo with the composition is effective to suppress in vivo growth of tumors or an infectious agent.

In one example of this approach, pre-immunization of mice with activated DC pulsed ex vivo with the HER-2 fusion protein composition, HER500*.rGM-CSF (SEQ ID NO:4), which has an antigenic component consisting of 289 amino acids derived from the extracellular domain of HER2 fused to 217 amino acids derived from the intracellular domain of HER2, suppressed the in vivo growth of HER-2-expressing autologous tumors in mice (Example 2). In another approach, animals, e.g., mice, are inoculated with a particular infectious agent or tumor-forming cells, then treated with an immunostimulatory fusion protein of the invention and evaluated for the ability of the antigenic composition to suppress in vivo growth of the infectious agent or an established tumor.

Example 3 illustrates this approach, in that post-infection injection of mice with activated DC pulsed ex vivo with the HER-2 fusion protein compositions, HER500*.rGM-CSF (SEQ ID NO:4), HER500*.hGM-CSF (SEQ ID NO:2), HER500* (SEQ ID NO:3), and HER500 (SEQ ID NO: 1), increased the survival time for mice previously inoculated with HER-2-expressing autologous tumor cells.

The results of the animal studies confirm that in order to generate an effective anti-tumor response, an immuostimulatory fusion protein of the invention must comprise antigenic sequence component and a sequence component derived from the intracellular domain of HER-2.

VI. Compositions and Methods for Immunotherapy and Cancer Therapy

The present invention provides immunostimulatory fusion protein compositions that are able to effectively present antigen for the induction of both $CD8^+$ CTL-mediated as well as $CD4^+$ Th cell proliferative responses.

As such, the immunostimulatory fusion protein compositions of the present invention are universally useful and can be employed in a wide range of immunotherapeutic, immunoprophylactic and cancer therapeutic applications involving generation of primary and secondary immune responses.

The invention also provides modified soluble polypeptide or protein antigens presented in the context of MHC Class I.

In a preferred embodiment, immunization with a modified soluble protein antigen of the invention results in an MHC Class I-mediated cellular immune response to an antigen which would not elicit a cellular immune response of the same magnitude, if provided in an unmodified form.

Immunization with such a modified soluble protein antigen results in an MHC Class I-mediated cellular immune response which is greater in magnitude and accordingly provides greater protection than a cellular immune response to the same antigen if provided in an unmodified form.

In one preferred embodiment, the invention provides an immunostimulatory composition comprising DCs exposed ex vivo to an immunostimulatory fusion protein comprising a polypeptide antigen sequence component and a sequence component derived from the intracellular domain of the HER-2 protein, as described above, which is able to more effectively induce T-cell responses, than a composition comprising the polypeptide antigen alone.

An immunostimulatory composition comprising DCs exposed ex vivo to an immunostimulatory fusion protein of the invention alone, or in combination with the immunostimulatory fusion protein finds utility in immunotherapy of a subject and can function as a vaccine.

In a related aspect, the invention includes a method of immunizing a subject against a polypeptide antigen associated with a particular type of cancer or infectious disease. The method includes exposing or pulsing DC with an immunostimulatory fusion protein composition, as further described below.

In practicing the methods of the invention, the exposing step can be carried out in vitro (ex vivo), in vivo or both in vitro and in vivo. For example, an immunostimulatory fusion protein of the invention may be directly injected into a subject or DC may be exposed to the immunostimulatory fusion protein in vitro in a manner effective to induce cell-surface presentation of the antigenic component of the fusion protein and the pulsed DC returned to the subject.

An antigenic composition comprising an immunostimulatory fusion protein alone or in combination with DC stimulated by in vitro exposure to the immunostimulatory fusion protein can be used, for example, in direct in vivo administration, ex vivo somatic therapy, in vivo implantable devices or in ex vivo extracorporeal devices.

It will be understood that any of a number of methods may be used to pulse DC with an immunostimulatory fusion protein of the invention, to make them effective to present antigen in the context of MHC I. The experiments detailed herein demonstrate that activation of DC by exposure to immunostimulatory fusion proteins facilitates processing of the antigenic component of the fusion protein through the "endogenous" class I pathway such that antigens are presented in association with MHC class I molecules, and accordingly are able to activate $CD8^+$ CTL.

From the foregoing, it will be appreciated that the invention provides compositions and methods having the unique feature that processing of soluble protein antigens occurs through the MHC class I, as opposed to class II, pathway.

VII. Therapeutic Applications

A. Exposing DC Ex Vivo to Immunostimulatory Fusion Protein Compositions

The invention is based on the discovery that DC can be exposed to an immunostimulatory fusion protein composition, either in vitro (ex vivo), or in vivo in a subject, resulting in a protective T cell mediated response against the antigenic component of the fusion protein.

DC are treated in vitro (ex vivo) with an immunostimulatory fusion protein composition, followed by administration to a subject. The subject may be the same individual from whom the DC were obtained (autologous transplantation) or a different individual (allogeneic transplantation). In allogeneic transplantation, the donor and recipient are matched based on similarity of HLA antigens in order to minimize the immune response of both donor and recipient cells against the other.

A subject may be treated with an immunostimulatory fusion protein composition of the invention alone or in combination with a therapeutic regimen typically used for the condition under treatment, e.g. radiation therapy and/or chemotherapy for the treatment of cancer.

In general, DC precursors are obtained, cultured under serum-free conditions in medium lacking exogenously supplied cytokines, as described above, followed by in vitro (ex vivo) exposure of the DC to an immunostimulatory fusion protein composition of the invention followed by re-infusion of the activated DC into the subject.

Re-infused ex vivo immunostimulatory fusion protein composition-treated DC provide a means for rapid generation of an immune response to the antigenic component of the fusion protein.

B. In Vivo Administration of an Immunostimulatory Fusion Protein Composition

In another aspect, the invention is directed to methods of treating a subject by in vivo administration of an immunostimulatory fusion protein composition of the invention.

In one embodiment, the subject has a type of cancer which expresses a tumor-specific antigen. In accordance with the present invention, an immunostimulatory fusion protein may be made which comprises a tumor-specific antigen sequence component and a sequence component derived from the intracellular domain of HER-2. In such cases, DC pulsed ex vivo with this immunostimulatory fusion protein are administered to a subject, alone or in combination with the fusion protein, resulting in an improved therapeutic outcome for the subject, evidenced by, e.g., a slowing or diminution of the growth of cancer cells or a solid tumor which expresses the tumor-specific antigen, or a reduction in the total number of cancer cells or total tumor burden.

In a related embodiment, the subject has been diagnosed as having a viral, bacterial, fungal or other type of infection, which is associated with the expression of a particular antigen, e.g., a viral antigen. In accordance with the present invention, an immunostimulatory fusion protein may be made which comprises a sequence component consisting of the antigen, e.g., an HBV-specific antigen, together with a sequence component derived from the intracellular domain of HER-2. In such cases, DC pulsed ex vivo with the immunostimulatory fusion protein are administered to a subject, alone or in combination with the fusion protein, resulting in an improved therapeutic outcome for the subject as evidenced by a slowing in the growth of the causative infectious agent within the subject and/or a decrease in, or elimination of, detectable symptoms typically associated with the particular infectious disease.

In either situation, in vivo administration of an immunostimulatory fusion protein of the invention to a subject provides a means to generate a protective DC-induced, T cell-mediated immune response to the antigen in the subject, dependent upon (1) the antigenic composition administered, (2) the duration, dose and frequency of administration, and (2) the general condition of the subject.

In one example, the subject has a HER-2-expressing cancer and administration of an immunostimulatory fusion protein composition of the invention which includes HER2 as the antigenic component of the fusion protein provides a means to improve the therapeutic outcome of the subject. In this embodiment, the immunostimulatory HER-2 composition is administered to the subject in a manner effective to result in a cellular immune response to HER-2-expressing cancer cells in the subject.

C. Treating Patients

Effective delivery of the immunostimulatory fusion protein composition is an important aspect of the invention. In accordance with the invention, such routes of delivery include, but are not limited to, various systemic routes, including parenteral routes, e.g., intravenous (IV), subcutaneous (SC), intraperitoneal (IP), and intramuscular (IM) injection.

It will be appreciated that methods effective to deliver an immunostimulatory fusion protein to dendritic cells or to introduce an immunostimulatory fusion protein or DC composition in close proximity to antigen-expressing cells are also contemplated.

In one preferred embodiment, the immunostimulatory composition is a fusion protein, contained in a pharmaceutically acceptable carrier, and delivered by the intravenous route. In a further aspect of this embodiment, the immunostimulatory fusion protein composition is administered at regular intervals for a short time period, e.g., in bi-weekly intervals for two months or less. However, in some cases the fusion protein composition is administered intermittently over a longer period of time.

Typically, one or more doses of the immunostimulatory fusion protein are administered, generally at bi-weekly intervals for a period of about two months. Preferred doses for administration by the IV, SC or IM route are from about 5 μg/kg per patient to about 5 mg/kg per patient.

In another preferred embodiment, the immunostimulatory composition comprises DC exposed ex vivo to an immunostimulatory fusion protein, contained in a pharmaceutically acceptable carrier, and delivered by the IV, SC or IM route.

In one aspect of this embodiment, the immunostimulatory fusion protein composition comprises from $10^7$ to $10^{11}$ DC, which have been exposed to from 100 ng/ml to 1 mg/ml of a given immunostimulatory fusion protein, in a manner effective to generate Ag-loaded DC as described in Examples 2 and 3. Doses of about $10^7$ to $10^{11}$ DC are then administered to the subject by intravenous or SC or IM injection according to established procedures for a short time period, e.g., at bi-weekly intervals for 2 months or less. However, in some cases the immunostimulatory fusion protein composition is administered intermittently over a longer period of time.

Typically, one or more doses of the immunostimulatory fusion protein composition are administered, generally at regular intervals for a period of about 2 months. In general, the method comprises administering to a subject, in a suitable pharmaceutical carrier, an amount of an immunostimulatory fusion protein or DC composition effective to result in an improved therapeutic outcome for the subject under treatment.

It follows that the immunostimulatory fusion protein or DC composition may be administered in any convenient vehicle, which is physiologically acceptable. Such an immunostimulatory fusion protein or DC composition may include any of a variety of standard physiologically acceptable carrier employed by those of ordinary skill in the art. Examples of such pharmaceutical carriers include, but are not limited to, saline, phosphate buffered saline (PBS), water and Ringer's solution. It will be understood that the choice of suitable physiologically acceptable carrier will vary dependent upon the chosen mode of administration.

Sustained release compositions are also contemplated within the scope of this application. These may include semi-permeable polymeric matrices in the form of shaped articles such as films or microcapsules.

In preferred applications of the method, the subject is a human subject. The subject may also be a cancer patient, in particular a patient diagnosed as having a cancer which expresses a particular cancer-specific or cancer-associated antigen, and the patient may or may not be under with chemotherapy and/or radiation therapy.

It will be understood that the effective in vivo dose of an immunostimulatory fusion protein or DC composition of the invention will vary according to the frequency and route of administration as well as the condition of the subject under treatment. Accordingly, such in vivo therapy will generally require monitoring by tests appropriate to the condition being treated and a corresponding adjustment in the dose or treatment regimen in order to achieve an optimal therapeutic outcome.

D. Monitoring Treatment

The efficacy of a given therapeutic regimen involving the methods described herein, may be monitored, e.g., by monitoring the induction of a CTL response, a helper T-cell response, and/or the antibody response to the antigenic component of the fusion protein in peripheral blood using methods well known in the art in addition to monitoring the status of the cancer and the biological condition of the subject, at various time points following such administration.

In cases where the subject has been diagnosed as having a particular type of cancer, the status of the cancer is also monitored using diagnostic techniques appropriate to the type of cancer under treatment. Similarly, in cases where the subject has been diagnosed as having a particular type of infection, the status of the infection is also monitored using diagnostic techniques appropriate to the type of type of infection under treatment.

The immunostimulatory fusion protein or DC composition treatment regimen may be adjusted (dose, frequency, route, etc.), as indicated, based on the condition of the subject under treatment and the results of the assays described above.

VIII. Utility

The present invention provides immunostimulatory fusion protein compositions that are able to effectively present antigen for the induction of both CD8$^+$ CTL-mediated as well as CD4$^+$ Th cell proliferative responses.

As such, the immunostimulatory fusion protein compositions of the invention are universally useful and can be employed in a wide range of immunotherapeutic, immunoprophylactic and cancer therapeutic applications involving generation of primary and secondary immune responses.

The immunostimulatory fusion protein compositions of the invention find utility in immunotherapy of cancers which are associated with expression of a particular antigen. For example, the HER-2 fusion protein compositions described herein find utility in immunotherapy of HER-2 expressing tumors, such as, breast carcinoma, ovarian cancer and colon cancer.

The advantages of the present invention include induction of enhanced cellular immunity to isolated or soluble polypeptide or protein antigens by presenting an immunostimulatory fusion protein of the invention to a dendritic cell (DC), resulting in DC activation. As discussed above, such induction is not generally observed using soluble, polypeptide or protein antigens as induction materials. The generation of such activated DC, may be accomplished in vitro (ex vivo) using autologous or allogeneic DC or may take place in vivo following administration of an immunostimulatory fusion protein of the invention to a subject.

All patent and literature references cited in the present specification are hereby expressly incorporated by reference in their entirety.

The following examples illustrate but are not intended in any way to limit the invention.

EXAMPLE 1

Production Of Exemplary HER-2 Fusion Proteins

In one example, human HER-2 was cloned from a SK-BR3 cell line according to methods known in the art. The stop codon at the 3' end of the sequence was mutated away, and a Not I site inserted in its place, to fuse the HER-2 cDNA to C-terminal tag peptide, rat GM-CSF, or human GM-CSF DNA. GM-CSF DNA was cloned from a PBMC library according to standard methods. A Not I site was inserted at the 5' end of the DNA, and an Xba I cloning site was inserted at the 3' end, along with an in-frame stop codon. PCR-generated cDNA's were digested with appropriate restriction enzymes and cloned into restriction vectors for transfection into specific mammalian or insect cell lines.

Expression vectors comprising the coding sequence for various HER-2 fusion proteins were used to transfect mammalian 293-EBNA cells (available from the company Invitrogen™) (transient expression) and insect SF21 cells (available from the company Clontech™, Palo Alto, Calif.). Fusion protein products were recovered from the tissue culture supernatants, and affinity purified by passage over a metal affinity column, (NTA resin, Qiagen). For HER500-hGM-CSF, analysis by SDS-PAGE revealed protein bands migrating at 120 kDa and 110 kDa as products from mammalian and insect cells, respectively. The predicted size of the 690 polypeptide backbone is 74877 kDa.

Human HER-2-derived proteins were produced as recombinant proteins using the following coding sequences.

The HER500*.rGM-CSF construct (SEQ ID NO: 4) was produced by expression of a coding sequence which included, in the 5' to 3' direction: a 32 amino acid PAP signal peptide, a 3 amino acid sequence of the mature PAP protein, an Ala Arg linker, a 3 amino acid HER-2 signal sequence, 289 amino acids of the mature HER-2 membrane distal extracellular domain, an Ala linker, the OVA-derived immunodominant octapeptide SIINFEKL ($OVA_{257-264}$)(SEQ ID NO:22), 217 amino acids of the HER-2 membrane distal intracellular domain, an Ala Ala linker, a 127 amino acid mature rat GM-CSF sequence, and Gly Ala Pro Pro Pro Ala His His His His His His (SEQ ID NO:17).

The HER300*.rGM-CSF construct (SEQ ID NO: 5) was produced by expression of a coding sequence which included, in the 5' to 3' direction: a 32 amino acid PAP signal sequence, a 3 amino acid sequence of the mature PAP protein, an Ala Arg linker, a 3 amino acid HER-2 signal sequence, 289 amino acids of the mature HER-2 membrane distal extracellular domain, an Ala linker, the OVA-derived immunodominant octapeptide SIINFEKL ($OVA_{257-264}$)(SEQ ID NO:22), an Ala linker, a 127 amino acid mature rat GM-CSF sequence, and Gly Ala Pro Pro Pro Ala His His His His His His (SEQ ID NO:17).

BP8 baculovirus expression vectors (available from the company Clontech™) comprising the coding sequence for the HER500*.rGM-CSF (SEQ ID NO: 9) or HER300*.rGM-CSF (SEQ ID NO: 10) fusion proteins were used to transfect SF21 cells. Fusion protein products were recovered from tissue culture supernatants, and affinity purified by metal affinity chromatography. Analysis by SDS-PAGE revealed protein bands migrating at 105 kDa for HER500*.rGM-CSF and 60 kDa for HER300*.rGM-CSF.

Once constructed, expressed and purified, HER-2 fusion molecules containing rat GM-CSF or human GM-CSF were tested for GM-CSF bioactivity appropriate assays and the presence of HER-2 was verified using HER-2-specific monoclonal antibodies in both Western blot analysis and in an ELISA test, according to methods well-known in the art.

Evaluation of In Vitro Presentation of HER-2 Fusion Proteins

The IL-2 secreting mouse T cell hybridoma B3Z, which responds to the mouse MHC class I ($H2-K^b$) bound OVA-derived peptide SIINFEKL ($OVA_{257-264}$; Jameson et al., 1993, J. Exp. Med. 177:1541) (SEQ ID NO:22), was used to evaluate the antigen presenting ability of HER-2 fusion proteins containing the OVA-derived immunodominant peptide SIINFEKL (SEQ ID NO:22).

Tissue cultures were maintained in IMDM medium supplemented with 10% FOS, 2 mM L-glutamine, 0.1 mg/ml kanamycin sulfate and $3 \times 10^{-5}$ M 2-ME (available from the company Gibco™, Grand Island, N.Y.) at 37° C. in a humidified atmosphere containing 5% $CO_2$ (tissue culture incubator).

Enriched preparations of activated DC were obtained by incubating autologous C57BL/6 spleen cells in tissue culture flasks for 2 h at 37° C., removing non-adherent cells, and culturing the remaining adherent cells for 2 days with 1 μM ionomycin.

An IL-2 secretion assay was performed as described previously [Kruisbeek, 1998, in Coligan et al. (eds.) Current Protocols in Immunology, Wiley, New York, N.Y., 1:3.14]. More specifically, $10^5$ hybridoma cells were cultured in 0.2-ml microwells in the presence of $3 \times 10^4$ activated DC and various concentrations of HER-2 antigens. One day later, culture supernatants were harvested and tested at 50% concentration for their ability to support the proliferation of $10^4$ HT-2 cells (an IL-2 dependent cell line) for 24 h, as measured by [$^3$H]thymidine incorporation during the final 6 h culture period.

The response of B3Z cells to the HER300*.rGM-CSF and HER500*.rGM-CSF fusion proteins relative to OVA (Grade VII, 99% pure chicken ovalbumin purchased from the company Sigma™, St. Louis, Mo.), was evaluated in vitro. The cell proliferation response indicated as CPM based on 3H thymidine uptake (FIG. 1) indicate that HER300*.rGM-CSF and HER500*.rGM-CSF fusion proteins are more efficient in stimulating B3Z than native OVA itself (about, 10-fold, and ≦100-fold, respectively). The 10-fold superiority of HER500*.rGM-CSF over HER300*.rGM-CSF indicates that the enhanced presentation of Ag is correlated with the inclusion of the additional intracellular HER-2 domain derived 217 amino acids in the fusion protein (which are present in HER500*.rGM-CSF but absent in HER300*.rGM-CSF).

EXAMPLE 2

Prevention of In Vivo Tumor Growth by Pre-Immunization with Ag-Pulsed DC

The effect of pre-immunization with HER-2-pulsed activated DC on suppression of in vivo growth of HER-2-expressing autologous tumors was evaluated in a murine model.

The mouse tumor cell line E.HER-2 was generated by transfecting EL-4 cells (C57BL/6 mouse strain derived thymoma; ATCC, Rockville, Md.) with the full length human HER-2 cDNA according to standard methods.

Human HER-2-derived proteins were produced as recombinant proteins as previously described in Example 1, using the following coding sequences.

The HER500 construct (SEQ ID NO: 1) was produced by expression of a coding sequence which included, in the 5' to 3' direction: a 32 amino acid PAP signal sequence, a 3 amino acid sequence of the mature PAP protein, an Ala Arg linker, 3 amino acids of HER-2 signal sequence, 289 amino acids of mature HER-2 membrane distal extracellular domain, 217 amino acids of the HER-2 membrane distal intracellular domain and a C-terminal tag consisting of Ala Ala Ala His His His His His His (SEQ ID NO:15).

The HER500.hGM-CSF construct (SEQ ID NO: 2) was produced by expression of a coding sequence which included, in the 5' to 3' direction: a 32 amino acid PAP signal sequence, a 3 amino acid sequence of the mature PAP protein, an Ala Arg linker, 3 amino acids of HER-2 signal sequence, 289 amino acids of the mature HER-2 membrane distal extracellular domain, 217 amino acids of the HER-2 membrane distal intracellular domain, an Ala Ala linker, a 127 amino acid mature human GM-CSF sequence and a C-terminal tag consisting of Gly Ala Pro Pro Pro Pro Ala Ala Ala His His His His His His (SEQ ID NO:16).

The HER500* construct (SEQ ID NO: 3) was produced by expression of a coding sequence which included, in the 5' to 3' direction: the coding sequence for: a 32 amino acid PAP signal sequence, a 3 amino acid sequence of the mature PAP protein, an Ala Arg linker, 3 amino acids of HER-2 signal sequence, 289 amino acids of the mature HER-2 membrane distal extracellular domain, a Ala linker, the OVA-derived immunodominant octapeptide SIINFEKL ($OVA_{257-264}$) (SEQ ID NO:22), 217 amino acids of the HER2 membrane distal intracellular domain and a C-terminal tag consisting of Ala Ala Ala His His His His His His (SEQ ID NO:15).

The HER500*rGM-CSF construct (SEQ ID NO: 4) was produced by expression of a coding sequence which included, in the 5' to 3' direction: a 32 amino acid PAP signal sequence, a 3 amino acid sequence of the mature PAP protein, an Ala Arg linker, 3 amino acids of HER-2 signal sequence, 289 amino acids of the mature HER-2 membrane distal extracellular domain, an Ala linker, the OVA-derived immunodominant octapeptide SIINFEKL ($OVA_{257-264}$) (SEQ ID NO:22), 217 amino acids of the HER2 membrane distal intracellular domain, an Ala Ala linker, a 127 amino acid mature rat GM-CSF sequence and a C-terminal tag consisting of Gly Ala Pro Pro Pro Pro Ala His His His His His His (SEQ ID NO:17).

The HER300*rGM-CSF construct (SEQ ID NO: 5) was produced by expression of a coding sequence which included, in the 5' to 3' direction: a 32 amino acid PAP signal sequence, a 3 amino acid sequence of the mature PAP protein, an Ala Arg linker, 3 amino acids of HER-2 signal sequence, 289 amino acids of the mature HER-2 membrane distal extracellular domain, an Ala linker, the OVA-derived imunodominant octapeptide SIINFEKL ($OVA_{257-264}$)(SEQ ID NO:22), an Ala linker, a 127 amino acid mature rat GM-CSF sequence and a C-terminal tag consisting of Gly Ala Pro Pro Pro Pro Pro Ala His His His His His His (SEQ ID NO:17).

Eight-week old randomized female C57BL/6 mice were given 3 IP injections of $2.5 \times 10^5$ Ag-pulsed activated DC in 0.1 ml PBS at 2-weeks intervals. Enriched preparations of activated DC were obtained by incubating female C57BL/6 spleen cells in tissue culture flasks for 2 h at 37° C., removing non-adherent cells, and subsequently culturing the remaining adherent cells for 2 days in the presence of 1 µM ionomycin (Sigma, St. Louis, Mo.; Czerniecki et al., 1997, *J. Immunol.* 159: 3823; Ridge et al., 1998, *Nature* 393: 474). The DC obtained in this manner were pulsed by 16 h co-culture with each of the indicated HER-2 fusion proteins at 1 µM, washed two times and injected into mice. Two weeks after the last in vivo immunization, mice were challenged with an IP injection of $5 \times 10^5$ E.HER-2 cells in 0.1 ml PBS. Mice were monitored daily and their survival recorded. The results of two independent experiments are shown in FIGS. 2A and 2B, respectively.

Figure 2A:
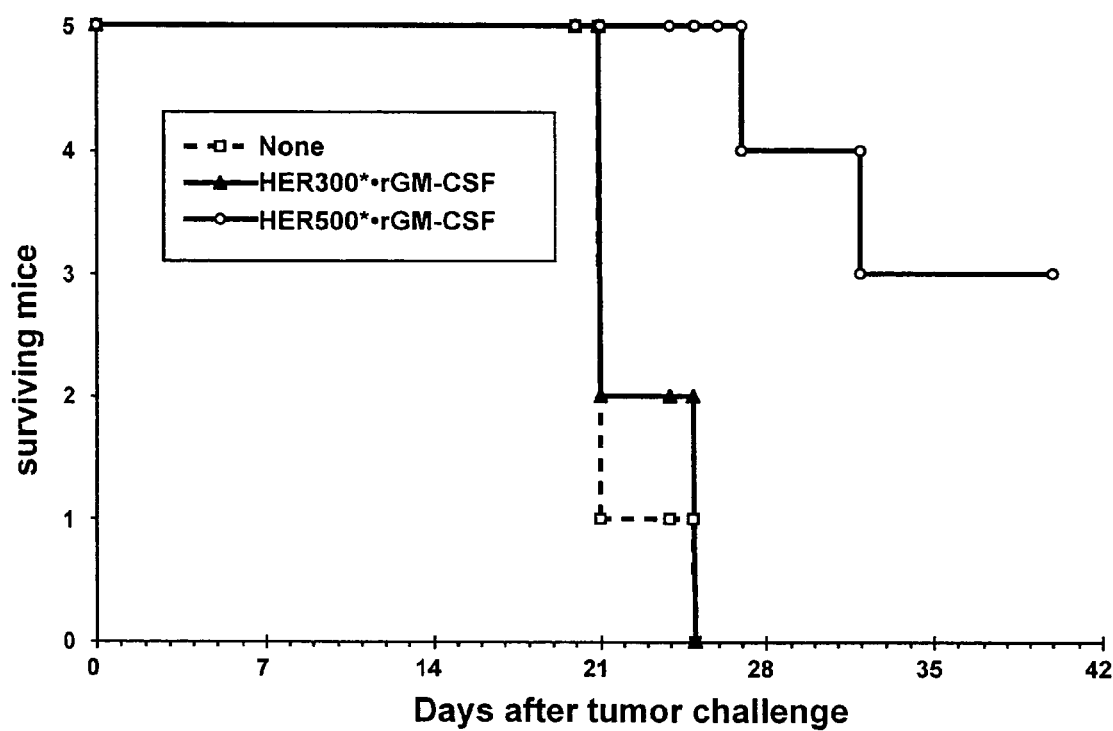
FIG. 2A shows the results of an experiment directed to the effect of pre-immunization with Ag-pulsed superactivated DC on the survival of mice up to 42 days after challenge with tumor cells, using "None" (open squares), "HER300*.rGM-CSF" (closed triangles) and HER500*.rGM-CSF (open circles), as the immunizing antigen.
Figure 2B:
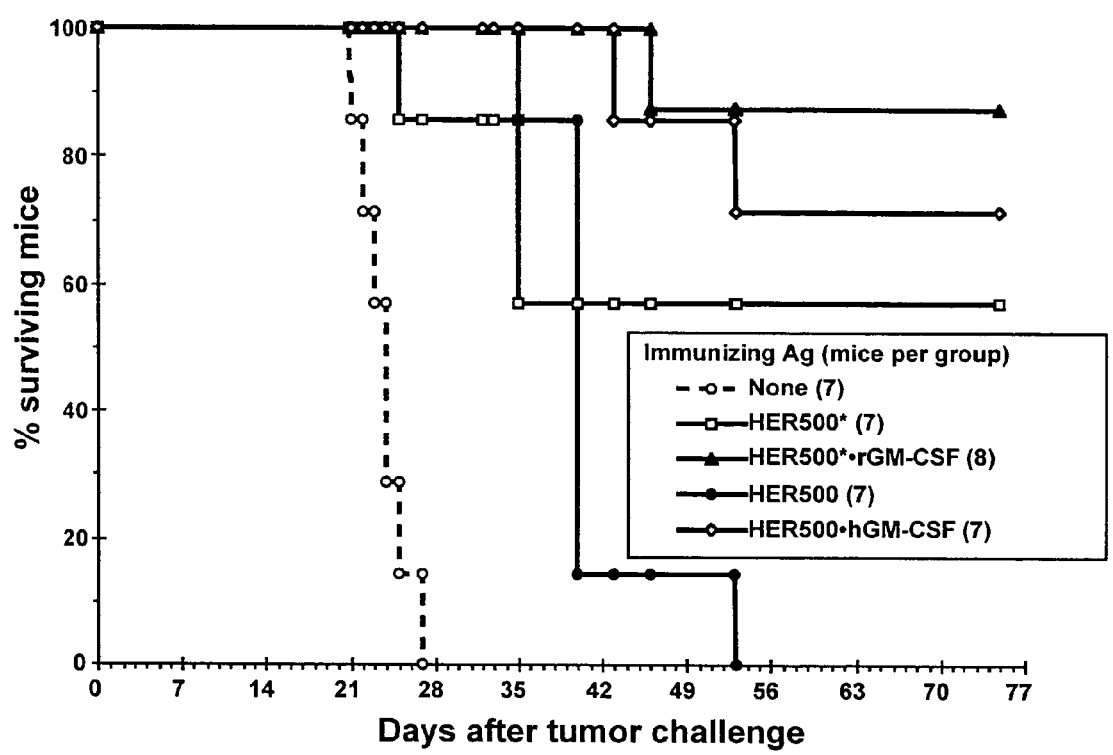
FIG. 2B shows the results of another experiment directed to the effect of pre-immunization with Ag-pulsed superactivated DC on the survival of mice up to 77 days after challenge with tumor cells, using "None" (open circles, 7 mice), "HER500*" (open squares, 7 mice), HER500*.rGM-CSF (closed triangles, 8 mice), "HER500" (closed circles, 7 mice), and HER500.hGM-CSF (closed diamonds, 7 mice), as the immunizing antigen.

While immunization with HER500.rGM-CSF-pulsed DC prevented the tumor growth, treatment with HER300*.rGM-CSF had no effect (FIG. 2A). These results are consistent with the results obtained in vitro in that they confirm the importance of the intracellular HER-2 domain derived segment in attaining a strong level of Ag presentation in order to generate an effective anti-tumor response. Experimental results shown in FIG. 2B demonstrate that a significant level of in vivo protection against a HER-2 expressing tumor can also be generated (a) when HER500-containing immunogens are either fused to the human GM-CSF (HER500.hGM-CSF), (b) in the absence of any GM-CSF when both an intracellular and extracellular portion of the HER-2 antigen is resent in the construct (HER500 and HER500*), and (c) in the absence of the OVA-derived peptide SIINFEKL (SEQ ID NO:22) (HER500 and HER500.hGM-CSF).

EXAMPLE 3

Figure 3:
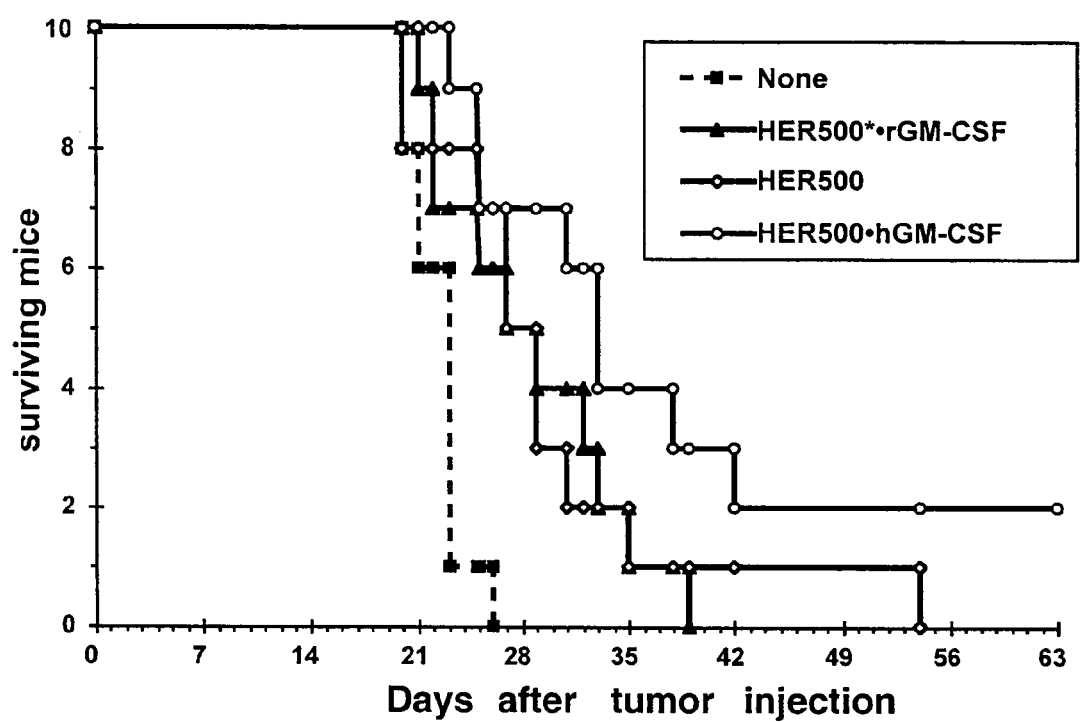
FIG. 3 shows the results of an experiment directed to the effect of post-infection immunization with Ag-pulsed superactivated DC on the survival of mice (10/group) up to 63 days after tumor cell injection, using "None" (closed squares), "HER500*.rGM-CSF" (closed triangles), HER500 (closed diamonds), and "HER500.hGM-CSF" (open circles) as the immunizing antigen.

In Vivo Suppression of an Established Tumor by Immunization with Ag-Pulsed Activated DC The efficacy of immunotherapy with different HER-2 fusion proteins was further evaluated by administration of the HER-2 fusion proteins to tumor-bearing laboratory mice (i.e., animals that were pre-injected with HER-2 expressing tumor cells). Twelve-week old IP injection of $5 \times 10^5$ E.HER-2 cells in 0.1 ml PBS on day 0, followed by 2 IP injections of $2.5 \times 10^5$ Ag-pulsed activated DC in 0.1 ml PBS (prepared as described in Example 2) one and 12 days later, respectively. Mice were monitored daily and their survival recorded. As shown in FIG. 3, treatment with DC pulsed with the HER500-containing antigenic constructs (HER500*.rGM-CSF, HER500, and HER500.hGM-CSF), exhibited a notable therapeutic effect, considerably prolonging the survival of tumor-bearing mice.

TABLE 2

Sequence Listing Table[7]

| Description | SEQ ID NO |
|---|---|
| HER500 amino acid sequence:<br>MRAAPLLLARAASLSLGFLFLLFFWLDRSVLAKELARGAASTQVCTGTDMKLRLPASPETHLDMLRHLYQGC<br>QVVQGNLELTYLPTNASLSFLQDIQEVQGYVLIAHNQVRQVPLQRLRIVRGTQLFEDNYALAVLDNGDPLNNT<br>TPVTGASPGGLRELQLRSLTEILKGGVLIQRYPQLCYQDTILWKDIFHKNNQLALTLIDTNRSACHPCSPMCKG<br>SRCWGESSEDCQSLTRTVCAGGCARCKGPLPTDCCHEQCAAGCTGPKHSDCLACLHFNHSGICELHCPALVTY<br>NTDTFESMPNPEGRYTFGASCVTACPYNYLSTDVGSGAGGMVHHRHRSSSTRSGGGDLTLGLEPSEEEAPRSP<br>LAPSEGAGSDVFDGDLGMGAAKGLQSLPTHDPSPLQRYSEDPTVPLPSETDGYVAPLTCSPQPEYVNQPDVRP<br>QPPSPREGPLPAARPAGATLERAKTLSPGKNGVVKDVFAFGGAVENPEYLTPQGGAAPQPHPPPAFSPAFDNLY<br>YWDQDPPERGAPPSTFKGTPTAENPEYLGLDVPAAAHHHHHH | 1 |

TABLE 2-continued

Sequence Listing Table[7]

| Description | SEQ ID NO |
|---|---|
| HER500●hGM-CSF amino acid sequence:<br>MRAAPLLLARAASLSLGFLFLLFFWLDRSVLAKELARGAASTQVCTGTDMKLRLPASPETHDLDMLRHLYQGC<br>QVVQGNLELTYLPTNASLSFLQDIQEVQGYVLIAHNQVRQVPLQRLRIVRGTQLFENYALAVLDNGDPLNNT<br>TPVTGASPGGLRELQLRSLTEILKGGVLIQRNPQLCYQDTILWKDIFHKNNQLALTLIDTNRSRACHPCSPMCKG<br>SRCWGESSEDCQSLTRTVCAGGCARCKGPLPTDCCHEQCAAGCTGPKHSDCLACLHFNHSGICELHCPALVTY<br>NTDTFESMPNPEGRYFGASCVTACPYNYLSTDVGSGAGGMVHHRHRSSSTRSGGGDLTLGLEPSEEEAPRSPL<br>APSEGAGSDVFDGDLGMGAAKGLQSLPTHDPSPLQRYSEDPTVPLPSETDGYVAPLTCSPQPEYVNQPDVRPQP<br>PSPREGPLPAARPAGATLERAKTLSPGKNGVVKDVFAFGGAVENPEYLTPQGGAAPQPHPPPAFSPAFDNLYY<br>WDQDPPERGAPPSTFKGTPTAENPEYLGLDVPAAAPARSPSPSTQPWEHVNAIQEARRLLNLSRDTAAEMNET<br>VEVISEMFDLQEPTCLQTRLELYKQGLRGSLTKLKGPLTMMASHYKQHCPPTPETSCATQIITFESFKENLKDFL<br>LVIPFDCWEPVQEGAPPPPAAAHHHHHH | 2 |
| HER500* amino acid sequence:<br>MRAAPLLLARAASKSLGFLFLLFFWLDRSVLAKELARGAASTQVCTGTDMKLRLPASPETHLDMLRHLYQGC<br>QVVQGNLELTYLPTNASLSFLQDIQEVQGYVLIAHNQVRQVPLQRLRIVRGTQLFEDNYALAVLDNGDPLNNT<br>TPVTGASPGGLRELQLRSLTRILKGGVLIQRNPQLCYQDTILWKDIFHKNNQLALTLIDTNRSRACHPCSPMCKG<br>SRCWGESSEDCQSLTRTVCAGGCARCKGPLPTDCCHEQCAAGCTGPKHSDCLACLHFNHNSGICELHCPALVTY<br>NTDTFESMPNPEGRYTFGASCVTACPYNTLSTDVGSASIINFEKLGAGGMVHHRHRSSSTRSGGGDLTLGLEPS<br>EEEAPRSPLAPSEGAGSDVFDGDLGMAGAAKGLQSLPTHDPSPLQRYSEDPTVPLPSETDGYVAPLTCSPQPEYV<br>NQPDVRPQPPSPREGPLPAARPAGATLERAKTLSPGKNGVVKDVFAFGGAVENPEYLTPQGGAAPQPHPPPAFS<br>PAFDNLYYWDQDPPERGAPPSTFKGTPTAENPEYLGLDVPAAAHHHHHH | 3 |
| HER500*●rGM-CSF amino acid sequence:<br>MRAAPLLLARAASKSLGFLFLLFFWLDRSVLAKELARGAASTQVCTGTDMKLRLPASPETHLDMLRHLYQGC<br>QVVQGNLELTYLPTNASLSFLQDIQEVQGYVLIAHNQVRQVPLQRLRIVRGTQLFEDNYALAVLDNGDPLNNT<br>TPVTGASPGGLRELQLRSLTRILKGGVLIQRNPQLCYQDTILWKDIFHKNNQLALTLIDTNRSRACHPCSPMCKG<br>SRCWGESSEDCQSLTRTVCAGGCARCKGPLPTDCCHEQCAAGCTGPKHSDCLACLHFNHNSGICELHCPALVTY<br>NTDTFESMPNPEGRYTFGASCVTACPYNTLSTDVGSASIINFEKLGAGGMVHHRHRSSSTRSGGGDLTLGLEPS<br>EEEAPRSPLAPSEGAGSDVFDGDLGMAGAAKGLQSLPTHDPSPLQRYSEDPTVPLPSETDGYVAPLTCSPQPEYV<br>NQPDVRPQPPSPREGPLPAARPAGATLERAKTLSPGKNGVVKDVFAFGGAVENPEYLTPQGGAAPQPHPPPAFS<br>LENEKNEDVDIISNEFSIQRPTCVQTRLKLYKQGLRGNLTKLNGALTMIASHYQTNCPPTPETDCEIEVTTFEDFI<br>KNLKGFLFDIPFDCWKVQKGAYPPPPAHHHHHH | 4 |
| HER300*●rGM-CSF amino acid sequence:<br>MRAAPLLLARAASKSLGFLFLLFFWLDRSVLAKELARGAASTQVCTGTDMKLRLPASPETHLDMLRHLYQGC<br>QVVQGNLELTYLPTNASLSFLQDIQEVQGYVLIAHNQVRQVPLQRLRIVRGTQLFEDNYALAVLDNGDPLNNT<br>TPVTGASPGGLRELQLRSLTRILKGGVLIQRNPQLCYQDTILWKDIFHKNNQLALTLIDTNRSRACHPCSPMCKG<br>SRCWGESSEDCQSLTRTVCAGGCARCKGPLPTDCCHEQCAAGCTGPKHSDCLACLHFNHNSGICELHCPALVTY<br>NTDTFESMPNPEGRYTFGASCVTACPYNTLSTDVGSASIINFEKLGAGGMVHHRHRSSSTRSGGGDLTLGLEPS<br>MRALENEKNEDVDIISNEFSIQRPTCVQTRLKLYKQGLRGNLTKLNGALTMIASHYQTNCPPTPETDCEIEVTTF<br>EDFIKNLKGFLFDIPFDCWKPVQKGAPPPPAHHHHHH | 5 |
| HER500 nucleoude coding sequence:<br>ATGAGAGCTGCACCCCTCCTCCTGGCCAGGGCAGCAAGCCTTAGCCTTGGCTTCTTGTTTCTGCTTTTTTTC<br>TGGCTAGACCGAAGTGTACTAGCCAAGGAGTTGGCGCGCGGGGCCGCGTCGACCCAAGTGTGCACCGGCA<br>CAGACATGAAGCTGCGGCTCCCTGCCAGTCCCGAGACCCACCTGGACATGCTCCGCCACCTCTACCAGGG<br>CTGCCAGGTGGTGCAGGGAAACCTGGAACTCACCTACCTGCCCACCAATGCCAGCCTGTCCTTCCTGCAG<br>GATATCCAGGAGGTGCAGGGCTACGTGCTCATCGCTCACAACCAAGTGAGGCAGGTCCCACTGCAGAGGC<br>TGCGGATTGTGCGAGGCACCCAGCTCTTTGAGGACAACTATGCCCTGGCCGTGCTAGACAATGGAGACCC<br>GCTGAACAATACCACCCCTGTCACAGGGGCCTCCCCAGGAGGCCTGCGGGAGCTGCAGCTTCGAAGCCTC<br>ACAGAGATCTTGAAAGGAGGGGTCTTGATCCAGCGGAACCCCCAGCTCTGCTACCAGGACACGATTTTGT<br>GGAAGGACATCTTCCACAAGAACAACCAGCTGGCTCTCACACTGATAGACAFFAACCGCTCTCGGGCCTG<br>CCACCCCTGTTCTCCGATGTGTAAGGGCTCCCGCTGCTGGGGACAGAGTTCTGAGGATTGTCAGAGCCTGA<br>CGCGCACTGTCTGTGCCGGTGGCTGTGCCCGCTGCAAGGGGCCACTGCCCACTGACTGCTGCCATGAGCA<br>GTGTGCTGCCGGCTGCACGGGCCCAAGCACTCTGACTGCCTGGCCTGCCTCCACTTCAACCACAGTGGA<br>TCTGTGAGCTGCACTGCCCAGCCCTGGTCACCTACAACACAGACACGTTTGAGTCCATGCCCAATCCCGAG<br>GGCCGGTATACATTCGGCGCCAGCTGTGTGACTGCCTGTCCCTACAACTACCTTTCTACGGACGTGGGATC<br>GGGCGCTGGGGCATGGTCCACCACAGGCACCGCAGCTCATCTACCAGGAGTGGCGGTGGGGACCTGACA<br>CTAGGGCTGGAGCCCTCTGAAGAGGAGGCCCCAGGTCTCACTGGCACCCTCCGAAGGGGCTGGCTCCG<br>ATGTATTTGATGGTGACCTGGGAATGGGGGCAGCCAAGGGGCTGCAAAGCCTCCCCACACATGACCCCAG<br>CCCTCTACAGCGGTACAGTGAGGACCCCACAGTACCCCTGCCCTCTGAGACTGATGGCTACGTTGCCCCCC<br>TGACCTGCAGCCCCAGCCTGAATATGTGAACCAGCCAGATGTTCGGCCCCAGCCCCTTCGCCCCCGAGA<br>GGGCCCTCTGCCTGCTGCCCGACCTGCTGGTGCCACTCTGGAAAGGGCCAAGACTCTCTCCCCAGGGAGA<br>AATGGGGTCGTCAAAGACGTTTTTGCCTTTGGGGGTGCCGTGGAGAACCCCGAGTACTTGACACCCCAGG<br>GAGGAGCTGCCCCTCAGCCCCACCCTCCTCCTGCCTTCAGCCCAGCCTTCGACAACCTCTATTACTGGAC<br>CAGGACCCACCAGAGCGGGGGGCTCCACCCAGCACCTTCAAAGGGACACCTACGGCAGAGAACCCAGAG<br>TACCTGGGTCTGGACGTGCCAGCGGCCGCACATCACCATCACCATCAC | 6 |
| HER500●hGM-CSF nucleonde coding sequence:<br>ATGAGAGCTGCACCCCTCCTCCTGGCCAGGGCAGCAAGCCTTAGCCTTGGCTTCTTGTTTCTGCTTTTTTTC<br>TGGCTAGACCGAAGTGTACTAGCCAAGGAGTTGGCGCGCGGGGCCGCGTCGACCCAAGTGTGCACCGGCA<br>CAGACATGAAGCTGCGGCTCCCTGCCAGTCCCGAGACCCACCTGGACATGCTCCGCCACCTCTACCAGGG | 7 |

TABLE 2-continued

Sequence Listing Table[7]

| Description | SEQ ID NO |
|---|---|
| CTGCCAGGTGGTGCAGGGAAACCTGGAACTCACCTACCTGCCCACCAATGCCAGCCTGTCCTTCCTGCAG<br>GATATCCAGGAGGTGCAGGGCTACGTGCTCATCGCTCACAACCAAGTGAGGCAGGTCCCACTGCAGAGGC<br>TGCGGATTGTGCGAGGCACCCAGCTCTTTGAGGACAACTATGCCCTGGCCGTGCTAGACAATGGAGACCC<br>GCTGAACAATACCACCCCTGTCACAGGGGCCTCCCCAGGAGGCCTGCGGGAGCTGCAGCTTCGAAGCCTC<br>ACAGAGATCTTGAAAGGAGGGGTCTTGATCCAGCGGAACCCCCAGCTCTGCTACCAGGACACGATTTTGT<br>GGAAGGACATCTTCCACAAGAACAACCAGCTGGCTCTCACACTGATAGACAFFAACCGCTCTCGGGCCTG<br>CCACCCCTGTTCTCCGATGTGTAAGGGCTCCCGCTGCTGGGGACAGAGTTCTGAGGATTGTCAGAGCCTGA<br>CGCGCACTGTCTGTGCCGGTGGCTGTGCCCGCTGCAAGGGGCCACTGCCCACTGACTGCTGCCATGAGCA<br>GTGTGCTGCCGGCTGCACGGGCCCAAGCACTCTGACTGCCTGGCCTGCCTCCACTTCAACCACAGTGGCA<br>TCTGTGAGCTGCACTGCCCAGCCCTGGTCACCTACAACACAGACACGTTTGAGTCCATGCCCAATCCCGAG<br>GGCCGGTATACATTCGGCGCCAGCTGTGTGACTGCCTGTCCCTACAACTACCTTTCTACGGACGTGGGATC<br>GGGCGCTGGGGCATGGTCACCACAGGCACCGCAGCTCATCTACCAGGAGTGGCGGTGGGGACCTGACA<br>CTAGGGCTGGAGCCCTCTGAAGAGGAGGCCCCCAGGTCTCCACTGGCACCCTCCGAAGGGGCTGGCTCCG<br>ATGTATTTGATGGTGACCTGGGAATGGGGGCAGCCAAGGGGCTGCAAAGCCTCCCCACACATGACCCCAG<br>CCCTCTACAGCGGTACAGTGAGGACCCCACAGTACCCCTGCCCTCTGAGACTGATGGCTACGTTGCCCCCC<br>TGACCTGCAGCCCCAGCCTGAATATGTGAACCAGCCAGATGTTCGGCCCCAGCCCCCTTCGCCCCGAGA<br>GGGCCCTCTGCCTGCTGCCCGACCTGCTGGTGCCACTCTGGAAAGGGCCAAGACTCTCTCCCCAGGGAAG<br>AATGGGGTCGTCAAAGACGTTTTTGCCTTTGGGGGTGCCGTGGAGAACCCCGAGTACTTGACACCCCAGG<br>GAGGAGCTGCCCCTCAGCCCCACCCTCCTCCTGCCTTCAGCCCAGCCTTCGACAACCTCTATTACTGGAC<br>CAGGACCCACCAGAGCGGGGGCTCCACCCAGCACCTTCAAAGGGACACCTACGGCAGAGAACCCAGAG<br>TACCTGGGTCTGGACGTGCCAGCGGCCGCACCCGCCCGCTCGCCCAGCCCCAGCACACAGCCCTGGGAGC<br>ATGTGAATGCCATCCAGGAGGCCCGGCGTCTCCTGAACCTGAGTAGAGACACTGCTGCTGAGATGAATGA<br>AACAGTAGAAGTCATCTCAGAAATGTTTGACCTCCAGGAGCCGACCTGCCTACAGACCCGCCTGGAGCTG<br>TACAAGCAGGGCCTGCGGGCAGCCTCACCAAGCTCAAGGGCCCCTTGACCATGATGGCCAGCCACTACA<br>AACAGCACTGCCCTCCAACCCCGGAAACTTCCTGTGCAACCCAGATTATCACCTTTGAAAGTTTCAAAGAG<br>AACCTGAAGGACTTTCTGCTTGTCATCCCCTTTGACTGCTGGGAGCCAGTCCAGGAGGGCGCGCCACCCCC<br>GCCGGCGGCCGCACATCACCATCACCATCAC | |
| HER500* nucleotide coding sequence:<br>ATGAGAGCTGCACCCCTCCTCCTGGCCAGGGCAGCAAGCCTTAGCCTTGGCTTCTTGTTTCTGCTTTTTTC<br>TGGCTAGACCGAAGTGTACTAGCCAAGGAGTTGGCGCGCGGGGCCGCGTCGACCCAAGTGTGCACCGGCA<br>CAGACATGAAGCTGCGGCTCCCTGCCAGTCCCGAGACCCACCTGGACATGCTCCGCACCTCTACCAGGG<br>CTGCCAGGTGGTGCAGGGAAACCTGGAACTCACCTACCTGCCCACCAATGCCAGCCTGTCCTTCCTGCAG<br>GATATCCAGGAGGTGCAGGGCTACGTGCTCATCGCTCACAACCAAGTGAGGCAGGTCCCACTGCAGAGGC<br>TGCGGATTGTGCGAGGCACCCAGCTCTTTGAGGACAACTATGCCCTGGCCGTGCTAGACAATGGAGACCC<br>GCTGAACAATACCACCCCTGTCACAGGGGCCTCCCCAGGAGGCCTGCGGGAGCTGCAGCTTCGAAGCCTC<br>ACAGAGATCTTGAAAGGAGGGGTCTTGATCCAGCGGAACCCCCAGCTCTGCTACCAGGACACGATTTTGT<br>GGAAGGACATCTTCCACAAGAACAACCAGCTGGCTCTCACACTGATAGACAFFAACCGCTCTCGGGCCTG<br>CCACCCCTGTTCTCCGATGTGTAAGGGCTCCCGCTGCTGGGGACAGAGTTCTGAGGATTGTCAGAGCCTGA<br>CGCGCACTGTCTGTGCCGGTGGCTGTGCCCGCTGCAAGGGGCCACTGCCCACTGACTGCTGCCATGAGCA<br>GTGTGCTGCCGGCTGCACGGGCCCAAGCACTCTGACTGCCTGGCCTGCCTCCACTTCAACCACAGTGGCA<br>TCTGTGAGCTGCACTGCCCAGCCCTGGTCACCTACAACACAGACACGTTTGAGTCCATGCCCAATCCCGAG<br>GGCCGGTATACATTCGGCGCCAGCTGTGTGACTGCCTGTCCCTACAACTACCTTTCTACGGACGTGGGATC<br>CGCTAGCATCATTAATTTCGAGAAGTTGGGCGCTGGGGCATGGTCCACCACAGGCACCGCAGCTCATCT<br>ACCAGGAGTGGCGGTGGGGACCTGACACTAGGGCTGGAGCCCTCTGAAGAGGAGGCCCCCAGGTCTCCAC<br>TGGCACCCTCCGAAGGGGCTGGCTCCGATGTATTTGATGGTGACCTGGGAATGGGGGCAGCCAAGGGGCT<br>GCAAAGCCTCCCCACACATGACCCCAGCCCTCTACAGCGGTACAGTGAGGACCCCACAGTACCCCTGCCC<br>TCTGAGACTGATGGCTACGTTGCCCCCCTGACCTGCAGCCCCCAGCCTGAATATGTGAACCAGCCAGATGT<br>TCGGCCCCAGCCCCCTTCGCCCCGAGAGGGCCCTCTGCTGCTGCCCGACCTGCTGGTGCCACTCTGGAAA<br>GGGCCAAGACTCTCTCCCCAGGGAAGAATGGGGTCGTCAAAGACGTTTTTGCCTTTGGGGGTGCCGTGGA<br>GAACCCCGAGTACTTGACACCCCAGGGAGGAGCTGCCCCTCAGCCCCACCCTCCTCCTGCCTTCAGCCCA<br>GCCTTCGACAACCTCTATTACTGGGACCAGGACCCACCAGAGCGGGGGCTCCACCCAGCACCCTTCAAAG<br>GGACACCTACGGCAGAGAACCCAGAGTACCTGGGTCTGGACGTGCCAGCGGCCGCACATCACCATCACCA<br>TCAC | 8 |
| HER500*●rGM-CSF nucleonde coding sequence:<br>ATGAGAGCTGCACCCCTCCTCCTGGCCAGGGCAGCAAGCCTTAGCCTTGGCTTCTTGTTTCTGCTTTTTTC<br>TGGCTAGACCGAAGTGTACTAGCCAAGGAGTTGGCGCGCGGGGCCGCGTCGACCCAAGTGTGCACCGGCA<br>CAGACATGAAGCTGCGGCTCCCTGCCAGTCCCGAGACCCACCTGGACATGCTCCGCACCTCTACCAGGG<br>CTGCCAGGTGGTGCAGGGAAACCTGGAACTCACCTACCTGCCCACCAATGCCAGCCTGTCCTTCCTGCAG<br>GATATCCAGGAGGTGCAGGGCTACGTGCTCATCGCTCACAACCAAGTGAGGCAGGTCCCACTGCAGAGGC<br>TGCGGATTGTGCGAGGCACCCAGCTCTTTGAGGACAACTATGCCCTGGCCGTGCTAGACAATGGAGACCC<br>GCTGAACAATACCACCCCTGTCACAGGGGCCTCCCCAGGAGGCCTGCGGGAGCTGCAGCTTCGAAGCCTC<br>ACAGAGATCTTGAAAGGAGGGGTCTTGATCCAGCGGAACCCCCAGCTCTGCTACCAGGACACGATTTTGT<br>GGAAGGACATCTTCCACAAGAACAACCAGCTGGCTCTCACACTGATAGACAFFAACCGCTCTCGGGCCTG<br>CCACCCCTGTTCTCCGATGTGTAAGGGCTCCCGCTGCTGGGGACAGAGTTCTGAGGATTGTCAGAGCCTGA<br>CGCGCACTGTCTGTGCCGGTGGCTGTGCCCGCTGCAAGGGGCCACTGCCCACTGACTGCTGCCATGAGCA<br>GTGTGCTGCCGGCTGCACGGGCCCAAGCACTCTGACTGCCTGGCCTGCCTCCACTTCAACCACAGTGGCA<br>TCTGTGAGCTGCACTGCCCAGCCCTGGTCACCTACAACACAGACACGTTTGAGTCCATGCCCAATCCCGAG<br>GGCCGGTATACATTCGGCGCCAGCTGTGTGACTGCCTGTCCCTACAACTACCTTTCTACGGACGTGGGATC<br>CGCTAGCATCATTAATTTCGAGAAGTTGGGCGCTGGGGCATGGTCCACCACAGGCACCGCAGCTCATCT<br>ACCAGGAGTGGCGGTGGGGACCTGACACTAGGGCTGGAGCCCTCTGAAGAGGAGGCCCCCAGGTCTCCAC<br>TGGCACCCTCCGAAGGGGCTGGCTCCGATGTATTTGATGGTGACCTGGGAATGGGGGCAGCCAAGGGGCT | 9 |

TABLE 2-continued

Sequence Listing Table[7]

| Description | SEQ ID NO |
|---|---|
| GCAAAGCCTCCCCACACATGACCCCAGCCCTCTACAGCGGTACAGTGAGGACCCCACAGTACCCCTGCCC<br>TCTGAGACTGATGGCTACGTTGCCCCCCTGACCTGCAGCCCCCCAGCCTGAATATGTGAACCAGCCAGATGT<br>TCGGCCCCAGCCCCCTTCGCCCCGAGAGGGCCCTCTGCTGCTGCCCGACCTGCTGGTGCCACTCTGGAAA<br>GGGCCAAGACTCTCTCCCCAGGGAAGAATGGGGTCGTCAAAGACGTTTTTGCCTTTGGGGGTGCCGTGGA<br>GAACCCCGAGTACTTGACACCCCAGGGAGGAGCTGCCCCTCAGCCCCACCCTCCTCCTGCCTTCAGCCCA<br>GCCTTCGACAACCTCTATTACTGGGACCAGGACCCACCAGAGCGGGGGCTCCACCCAGCACCCTTCAAAG<br>GGACACCTACGGCAGAGAACCCAGAGTACCTGGGTCTGGACGTGCCAGCGGCCGCACATCACCATCACCA<br>CAACCCTGTCACCCGGCCCTGGAAGCATGTAGATGCCATCAGAAGCTCTGAGCCTCCTAAATGACATG<br>CGTGCTCTGGAGAACGAAAAGAACGAAGACGTAGACATCATCTCTAATGAGTTCTCCATCCAGAGGCCGA<br>CATGTGTGCAGACCCGCCTGAAGCTATACAAGCAGGGTCTACGGGGCAACCTCACCAAACTCAATGGCGC<br>CTTGACCATGATAGCCAGCCACTACCAGACGAACTGCCCTCCAACCCCGGAAAACTGACTGTGAAATAGAA<br>GTCACCACCTTTGAGGATTTCATAAAGAACCTTAAAGGCTTTCTGTTTGATATCCCTTTTGACTGCTGGAA<br>GCCGGTCCAGAAAGGCGCGCCACCCCCGCCGGCGCATCACCATCACCATCAC | |
| HER300*●rGM-CSF nucleotide coding sequence:<br>ATGAGAGCTGCACCCCTCCTCCTGGCCAGGGCAGCAAGCCTTAGCCTTGGCTTCTTGTTTCTGCTTTTTTTC<br>TGGCTAGACCGAAGTGTACTAGCCAAGGAGTTGGCGCGCGGGGCCGCGTCGACCCAAGTGTGCACCGGCA<br>CAGACATGAAGCTGCGGCTCCCTGCCAGTCCCGAGACCCACCTGGACATGCTCCGCCACCTCTACCAGGG<br>CTGCCAGGTGGTGCAGGGAAACCTGGAACTCACCTACCTGCCCACCAATGCCAGCCTGTCCTTCCTGCAG<br>GATATCCAGGAGGTGCAGGGCTACGTGCTCATCGCTCACAACCAAGTGAGGCAGGTCCCACTGCAGAGGC<br>TGCGGATTGTGCGAGGCACCCAGCTCTTTGAGGACAACTATGCCCTGGCCGTGCTAGACAATGGAGACCC<br>GCTGAACAATACCACCCCTGTCACAGGGGCCTCCCCAGGAGGCCTGCGGGAGCTGCAGCTTCGAAGGCCTC<br>ACAGAGATCTTGAAAGGAGGGGTCTTGATCCAGCGGAACCCCCAGCTCTGCTACCAGGACACGATTTTGT<br>GGAAGGACATCTTCCACAAGAACAACCAGCTGGCTCTCACACTGATAGACAFFAACCGCTCTCGGGCCTG<br>CCACCCCTGTTCTCCGATGTGTAAGGGCTCCCGCTGCTGGGACAGAGTTCTGAGGATTGTCAGAGCCTGA<br>CGCGCACTGTCTGTGCCGGTGGCTGTGCCCGCTGCAAGGGGCCACTGCCCACTGACTGCTGCCATGAGCA<br>GTGTGCTGCCGGCTGCACGGGCCCAAGCACTCTGACTGCCTGCCTCCACTTCAACCACAGTGGCA<br>TCTGTGAGCTGCACTGCCCAGCCCTGGTCACCTACAACACAGACACGTTTGAGTCCATGCCCAATCCCGAG<br>GGCCGGTATACATTCGGCGCCAGCTGTGTGACTGCCTGTCCCTACAACTACCTTTCTACGGACGTGGGATC<br>CGCTAGCATCATTAATTTCGAGAAGTTGGCCGCCCCCACCCGCTCACCCAACCCTGTCACCCGGCCCTGGA<br>AGCATGTAGATGCCATCAAAGAAGCTCTGAGCCTCCTAAATGACATGCGTGCTCTGGAGAACGAAAAGAA<br>CGAAGACGTAGACATCATCTCTAATGAGTTCTCCATCCAGAGGCCGACATGTGTGCAGACCCGCCTGAAG<br>CTATACAAGCAGGGTCTACGGGGCAACCTCACCAAACTCAATGGCGCCTTGACCATGATAGCCAGCCACT<br>ACCAGACGAACTGCCCTCCAACCCCGGAAACTGACTGTGAAATAGAAGTCACCACCTTTGAGGATTTCAT<br>AAAGAACCTTAAAGGCTTTCTGTTTGATATCCCTTTTGACTGCTGGAAGCCGGTCCAGAAAGGCGCGCCAC<br>CCCCGCCGGCGCATCACCATCACCATCAC | 10 |
| 32 amino acid PAP signal sequence:<br>(corresponding to amino acids 1 to 32 of GenBank Accession No. NM_001099)<br>MRAAPLLLARAASLSLGFLFLLFFWLDRSVLA | 11 |
| 3 amino acid mature PAP amino acid:<br>(corresponding to amino acids 33 to 35 of GenBank Accession No. NM_001099)<br>KEL | 12 |
| 3 amino acid HER-2 signal sequence:<br>(corresponding to amino acids 19 to 21 GenBank Accession No. M11730)<br>GAA | 13 |
| 2 amino acid linker sequence between mature PAP and HER-2 signal sequence:<br>Ala Arg | 14 |
| C-terminal 9 amino acid sequence found on HER500 and HER500* constructs:<br>Ala Ala Ala His His His His His His | 15 |
| C-terminal 15 amino acid sequence found in HER500-hGM-CSF:<br>Gly Ala Pro Pro Pro Pro Ala Ala Ala His His His His His His | |
| C-cerminal 13 amino acid sequence found in HER500* and HER300* rat GM-CSF constructs:<br>Gly Ala Pro Pro Pro Pro Ala His His His His His | 17 |
| Mature human GM-CSF amino acid sequence:<br>(corresponding to amino acids 18 to 144 GenBank Accession No. NM_000758)<br>APARSPSPSTQPWEHVNAIQEARRLLNLSRDTAAEMNETVEVISEMFDLQEPTCLQTRLELYKQGLRGSLTKLK<br>GPLTMMASHYKQHCPPTPETSCATIITFESFKENLKDFLLVIPFDCWEPVQE | 18 |
| Mature human GM-CSF nucleotide sequence:<br>(corresponding to nucleotides 60 to 440 GenBank Accession No. NM_000758)<br>GCACCCGCCCGCTCGCCCAGCCCCAGCACGCAGCCCTGGGAGCATGTGAATGCCATCCAGGAGGCCCGGC<br>GTCTCCTGAACCTGAGTAGAGACACTGCTGCTGAGATGAATGAAACAGTAGAAGTCATCTCAGAAATGTT<br>TGACCTCCAGGAGCCGACCTGCCTACAGACCCGCCTGGAGCTGTACAAGCAGGGCCTGCGGGGCAGCCTC<br>ACCAAGCTCAAGGGCCCCTTGACCATGATGGCCAGCCACTACAAGCAGCACTGCCCTCCAACCCCGGAAA | 19 |

TABLE 2-continued

Sequence Listing Table[7]

| Description | SEQ ID NO |
|---|---|
| CTTCCTGTGCAACCCAGACTATCACCTTTGAAAGTTTCAAAGAGAACCTGAAGGACTTTCTGCTTGTCATC<br>CCCTTTGACTGCTGGGAGCCAGTCCAGGAG | |
| Mature rat GM-CSF amino acid sequence:<br>(corresponding to amino acids 1 to 127 GenBank Accession No. U00620)<br>APTRSPNPVTRPWKHVDAIKEALSKKNDMRALENEKNEDVDIISNEFSIQRPTCVQTRLKLYKQGLRGNLTKLN<br>GALTMLASHYQTNCPPTPETDCEIEVTTFEDFIKNLKGFLFDIPFDCWKPVQK | 20 |
| Mature rat GM-CSF nucleotide sequence:<br>(corresponding to nucleotide 1 to 381 GenBank Accession No. U00620)<br>GCACCCACCCGCTCACCCAACCCTGTCACCCGGCCCTGGAAGCATGTAGATGCCATCAAAGAAGCTCTGA<br>GCCTCCTAAATGACATGCGTGCTCTGGAGAACGAAAAGAACGAAGACGTAGACATCATCTCTAATGAGTT<br>CTCCATCCAGAGGCCGACATGTGTGCAGACCCGCCTGAAGCTATACAAGCAGGGTCTACGGGGCAACCTC<br>ACCAAACTCAATGGCGCCTTGACCATGATAGCCAGCCACTACCAGACGAACTGCCCTCCAACCCCGGAAA<br>CTGACTGTGAAATAGAAGTCACCACCTTTGAGGATTTCATAAAGAACCTTAAAGGCTTTCTGTTTGATATC<br>CCTTTTGACTGCTGGAAGCCGGTCCAGAAA | 21 |
| Reporter peptide in constructs HER500* and HER500*ratGM-CSF:<br>(OVA-derived immunodominant octapeptide SIINFEKL (OVA$_{257-264}$))<br>(SEQ ID NO: 22) | 22 |
| 289 amino acids of mature HER-2 membrane distal extracellular domain:<br>(amino acids 22 to 310 of GenBank Accession No. M11730)<br>STQVCTGTDMKLRLPASPETHLDMLRHLYQQGCQVVQGNLELTYLPTNASLSFLQDIQEVQGYVLIAHNQVRQV<br>PLQRLRIVRGTQLFEDNYALAVLDNGDPLNNTTPVTGASPGGLRELQLRSLTEILKGGVLIQRNPQLCYQKTIL<br>WKDIFHKNNQLALTLIDTNRSRACHPCSPMCKGSRCWGESSEDCQSLTRTVCAGGCARCKGPLPTDCCHEQCA<br>AGCTGPKHSDCLACLHFNHSGICELHCPALVTYNTDTFESMPNPEGRYTFGASCVTACPYNYLSTDVGS | 23 |
| coding sequence for 289 amino acids of mature HER-2 membrane distal extraceilular domain:<br>(nucleotides 214 to 1080 of GenBank Accession No. M11730)<br>AGCACCCAAGTGTGCACCGGCACAGACATGAAGCTGCGGCTCCCTGCCAGTCCCGAGACCCACCTGGACA<br>TGCTCCGCCACCTCTACCAGGGCTGCCAGGTGGTGCAGGGAAACCTGGAACTCACCTACCTGCCCACCAA<br>TGCCAGCCTGTCCTTCCTGCAGGATATCCAGGAGGTGCAGGGCTACGTGCTCATCGCTCACAACCAAGTG<br>AGGCAGGTCCCACTGCAGAGGCTGCGGATTGTGCGAGGCACCCAGCTCTTTGAGGACAACTATGCCCTGG<br>CCGTGCTAGACAATGGAGACCCGCTGAACAATACCACCCCTGTCACAGGGGCCTCCCCAGGAGGCCTGCG<br>GGAGCTGCAGCTTCGAAGCCTCACAGAGATCTTGAAAGGAGGGGTCTTGATCCAGCGGAACCCCCAGCTC<br>TGCTACCAGGACACGATTTTGTGGAAGGACATCTTCCACAAGAACAACCAGCTGGCTCTCACACTGATAG<br>ACACCAACCGCTCTCGGGCCTGCCACCCCTGTTCTCCGATGTGTAAGGGCTCCCGCTGCTGGGGAGAGAGT<br>TCTGAGGATTGTCAGAGCCTGACGCGCACTGTCTGTGCCGGTGGCTGTGCCCGCTGCAAGGGGCCACTGC<br>CCACTGACTGCTGCCATGAGCAGTGTGCTGCCGGCTGCACGGGCCCAAGCACTCTGACTGCCTGGCCTG<br>CCTCCACTTCAACCACAGTGGCATCTGTGAGCTGCACTGCCCAGCCCTGGTCACCTACAACACAGACACGT<br>TTGAGTCCATGCCCAATCCCGAGGGCCGGTATACATTCGGCGCCAGCTGTGTGACTGCCTGTCCCTACAAC<br>TACCTTTCTACGGACGTGGGATCC | 24 |
| 217 amino acids of the membrane distal intracellular HER-2 domain:<br>(amino acids 1038 to 1254 of GenBank Accession No. M11730)<br>GAGGGMVHHRHRSSSTRSGGGDLTLGLEPSEEEAPRSPLAPSEGAGSDVDLGMGAAKGLQSLPTHDPSPLQ<br>RYSEDPTVPLPSETDGYVAPLTCSPQPEYVNQPDVRPQPPSPREGPLPAARPAGATLERAKTLSPGKNGVVKDV<br>FAFGGAVENPEYLTPQGGAAPQPHPPPAFSPAFDNLYYWDQDPPERGAPPSTFKGTPTAINPEYLGLDVP | 25 |
| coding sequence for 217 amino acids of the membrane distal intracellular HER-2 domain:<br>(nucleotides 3262 to 3912 of GenBank Accession No. M11730)<br>GGCGCTGGGGGCATGGTCCACCACAGGCACCGCAGCTCATCTACCAGGAGTGGGTGGCGGACCTGACAC<br>TAGGGCTGGAGCCCTCTGAAGAGGAGGCCCCCAGGTCTCCACTGGCACCCTCCGAAGGGGCTGGCTCCGA<br>TGTATTTGATGGTGACCTGGGAATGGGGGCAGCCAAGGGGCTGCAAAGCCTCCCCACACATGACCCCAGC<br>CCTCTACAGCGGTACAGTGAGGACCCCACAGTACCCCTGCCCCTGCACCTGATGGCTACGTTGCCCCCCT<br>GACCTGCAGCCCCCAGCCTGATATGTGAACCAGCCAGATGTTCGGCCCCAGCCCCCTTCGCCCCGAGAG<br>GGCCCCTCTGCCTGCTGCCCGACCTGCTGGTGCCACTCTGAAAGGGCCAAGACTCTCTCCCCAGGGAAGA<br>ATGGGGTCGTCAAAGACGTTTTTGCCTTTGGGGGTGCCGTGGAGAACCCCGAGTACTTGACACCCCAGGG<br>AGGAGCTGCCCCTCAGCCCCACCCTCCTCCTGCCTTCAGCCCAGCCTTCGACAACCTCTATTACTGGGACC<br>AGGACCCACCAGAGCGGGGGCTCCACCCAGCACCTTCAAAGGGACACCTACGGCAGAGAACCCAGAGT<br>ACCTGGGTCTGGACGTGCCA | 26 |
| NY-ESO-IC Amino Acid Sequence: amino acids 1 to 180 of GenBank Accession No. U87459 fused to<br>the 217 amino acids of membrane distal intracellular HER-2 domain (amino acids 1038 to 1254<br>of GenBank ™ Accession No. M11730) | 27 |
| NY-ESO-IC DNA Sequence: nucleotides 54 to 593 of GenBank Accession No. U87459 fused to the<br>coding sequence for the 217 amino acids of the membrane distal intracellular HER-2 domain<br>(nucleotides 3262 to 3912 of GenBank Accession No. M11730): | 28 |
| SART3-IC Amino Acid Sequence: amino acids 1 to 962 of GenBank Accession No. AB020880 fused<br>to the 217 amino acids of membrane distal intracellular HER-2 domain (amino acids 1038 to<br>1254 of GenBank Accession No. M11730) | 29 |

TABLE 2-continued

Sequence Listing Table[7]

| Description | SEQ ID NO |
|---|---|
| SART3-IC DNA Sequence: nucleotides 20 to 2905 of GenBank Accession No. AB020880 fused to the coding sequence for the 217 amino acids of the membrane distal intracellular HER-2 domain (nucleotides 3262 to 3912 of GenBank Accession No. M11730) | 30 |

[7]All sequences are presented in single stranded form in the 5' to 3' direction.

It is claimed:

1. An immunostimulatory composition, comprising: dendritic cells activated in vitro by exposure to an immunostimulatory fusion protein selected from the group consisting of HER500 comprising SEQ ID NO: 1, HER500·hGM-CSF comprising SEQ ID NO: 2, HER500* comprising SEQ ID NO:3, and HER500*·rGM-CSF comprising SEQ ID NO: 4, and wherein the activated dendritic cells are capable of eliciting an immune response against the HER-2 sequence of which the fusion protein is comprised.

2. The composition of claim 1 in which the immunostimulatory fusion protein is HER500·hGM-CSF comprising SEQ ID NO:2.

3. The composition of claim 1 in which the dendritic cells are human dendritic cells.

* * * * *

UNITED STATES PATENT AND TRADEMARK OFFICE
CERTIFICATE OF CORRECTION

PATENT NO. : 7,659,117 B2  Page 1 of 1
APPLICATION NO. : 11/144912
DATED : February 9, 2010
INVENTOR(S) : Laus et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 822 days.

Signed and Sealed this

Thirtieth Day of November, 2010

David J. Kappos
*Director of the United States Patent and Trademark Office*

SEQUENCE LISTING

<160> NUMBER OF SEQ ID NOS: 30

<210> SEQ ID NO 1
<211> LENGTH: 555
<212> TYPE: PRT
<213> ORGANISM: Artificial Sequence
<220> FEATURE:
<223> OTHER INFORMATION: HER500 construct

<400> SEQUENCE: 1

```
Met Arg Ala Ala Pro Leu Leu Leu Ala Arg Ala Ala Ser Leu Ser Leu
 1               5                   10                  15

Gly Phe Leu Phe Leu Leu Phe Phe Trp Leu Asp Arg Ser Val Leu Ala
                20                  25                  30

Lys Glu Leu Ala Arg Gly Ala Ala Ser Thr Gln Val Cys Thr Gly Thr
            35                  40                  45

Asp Met Lys Leu Arg Leu Pro Ala Ser Pro Glu Thr His Leu Asp Met
        50                  55                  60

Leu Arg His Leu Tyr Gln Gly Cys Gln Val Val Gln Gly Asn Leu Glu
65                  70                  75                  80

Leu Thr Tyr Leu Pro Thr Asn Ala Ser Leu Ser Phe Leu Gln Asp Ile
                85                  90                  95

Gln Glu Val Gln Gly Tyr Val Leu Ile Ala His Asn Gln Val Arg Gln
            100                 105                 110

Val Pro Leu Gln Arg Leu Arg Ile Val Arg Gly Thr Gln Leu Phe Glu
        115                 120                 125

Asp Asn Tyr Ala Leu Ala Val Leu Asp Asn Gly Asp Pro Leu Asn Asn
    130                 135                 140

Thr Thr Pro Val Thr Gly Ala Ser Pro Gly Gly Leu Arg Glu Leu Gln
145                 150                 155                 160

Leu Arg Ser Leu Thr Glu Ile Leu Lys Gly Gly Val Leu Ile Gln Arg
                165                 170                 175

Asn Pro Gln Leu Cys Tyr Gln Asp Thr Ile Leu Trp Lys Asp Ile Phe
            180                 185                 190

His Lys Asn Asn Gln Leu Ala Leu Thr Leu Ile Asp Thr Asn Arg Ser
        195                 200                 205

Arg Ala Cys His Pro Cys Ser Pro Met Cys Lys Gly Ser Arg Cys Trp
    210                 215                 220

Gly Glu Ser Ser Glu Asp Cys Gln Ser Leu Thr Arg Thr Val Cys Ala
225                 230                 235                 240

Gly Gly Cys Ala Arg Cys Lys Gly Pro Leu Pro Thr Asp Cys Cys His
                245                 250                 255
```

-continued

```
Glu Gln Cys Ala Ala Gly Cys Thr Gly Pro Lys His Ser Asp Cys Leu
                260                 265                 270
Ala Cys Leu His Phe Asn His Ser Gly Ile Cys Glu Leu His Cys Pro
            275                 280                 285
Ala Leu Val Thr Tyr Asn Thr Asp Thr Phe Glu Ser Met Pro Asn Pro
        290                 295                 300
Glu Gly Arg Tyr Thr Phe Gly Ala Ser Cys Val Thr Ala Cys Pro Tyr
305                 310                 315                 320
Asn Tyr Leu Ser Thr Asp Val Gly Ser Gly Ala Gly Gly Met Val His
                325                 330                 335
His Arg His Arg Ser Ser Ser Thr Arg Ser Gly Gly Gly Asp Leu Thr
                340                 345                 350
Leu Gly Leu Glu Pro Ser Glu Glu Ala Pro Arg Ser Pro Leu Ala
            355                 360                 365
Pro Ser Glu Gly Ala Gly Ser Asp Val Phe Asp Gly Asp Leu Gly Met
        370                 375                 380
Gly Ala Ala Lys Gly Leu Gln Ser Leu Pro Thr His Asp Pro Ser Pro
385                 390                 395                 400
Leu Gln Arg Tyr Ser Glu Asp Pro Thr Val Pro Leu Pro Ser Glu Thr
                405                 410                 415
Asp Gly Tyr Val Ala Pro Leu Thr Cys Ser Pro Gln Pro Glu Tyr Val
            420                 425                 430
Asn Gln Pro Asp Val Arg Pro Gln Pro Pro Ser Pro Arg Glu Gly Pro
        435                 440                 445
Leu Pro Ala Ala Arg Pro Ala Gly Ala Thr Leu Glu Arg Ala Lys Thr
        450                 455                 460
Leu Ser Pro Gly Lys Asn Gly Val Val Lys Asp Val Phe Ala Phe Gly
465                 470                 475                 480
Gly Ala Val Glu Asn Pro Glu Tyr Leu Thr Pro Gln Gly Gly Ala Ala
                485                 490                 495
Pro Gln Pro His Pro Pro Pro Ala Phe Ser Pro Ala Phe Asp Asn Leu
            500                 505                 510
Tyr Tyr Trp Asp Gln Asp Pro Pro Glu Arg Gly Ala Pro Pro Ser Thr
        515                 520                 525
Phe Lys Gly Thr Pro Thr Ala Glu Asn Pro Glu Tyr Leu Gly Leu Asp
530                 535                 540
Val Pro Ala Ala Ala His His His His His His
545                 550                 555

<210> SEQ ID NO 2
<211> LENGTH: 690
<212> TYPE: PRT
<213> ORGANISM: Artificial Sequence
<220> FEATURE:
<223> OTHER INFORMATION: HER500-hGM-CSF construct

<400> SEQUENCE: 2

Met Arg Ala Ala Pro Leu Leu Leu Ala Arg Ala Ala Ser Leu Ser Leu
1               5                   10                  15
Gly Phe Leu Phe Leu Leu Phe Phe Trp Leu Asp Arg Ser Val Leu Ala
            20                  25                  30
Lys Glu Leu Ala Arg Gly Ala Ser Thr Gln Val Cys Thr Gly Thr
        35                  40                  45
Asp Met Lys Leu Arg Leu Pro Ala Ser Pro Glu Thr His Leu Asp Met
    50                  55                  60
```

```
Leu Arg His Leu Tyr Gln Gly Cys Gln Val Val Gln Gly Asn Leu Glu
 65                  70                  75                  80

Leu Thr Tyr Leu Pro Thr Asn Ala Ser Leu Ser Phe Leu Gln Asp Ile
             85                  90                  95

Gln Glu Val Gln Gly Tyr Val Leu Ile Ala His Asn Gln Val Arg Gln
            100                 105                 110

Val Pro Leu Gln Arg Leu Arg Ile Val Arg Gly Thr Gln Leu Phe Glu
            115                 120                 125

Asp Asn Tyr Ala Leu Ala Val Leu Asp Asn Gly Asp Pro Leu Asn Asn
130                 135                 140

Thr Thr Pro Val Thr Gly Ala Ser Pro Gly Gly Leu Arg Glu Leu Gln
145                 150                 155                 160

Leu Arg Ser Leu Thr Glu Ile Leu Lys Gly Gly Val Leu Ile Gln Arg
                165                 170                 175

Asn Pro Gln Leu Cys Tyr Gln Asp Thr Ile Leu Trp Lys Asp Ile Phe
            180                 185                 190

His Lys Asn Asn Gln Leu Ala Leu Thr Leu Ile Asp Thr Asn Arg Ser
        195                 200                 205

Arg Ala Cys His Pro Cys Ser Pro Met Cys Lys Gly Ser Arg Cys Trp
210                 215                 220

Gly Glu Ser Ser Glu Asp Cys Gln Ser Leu Thr Arg Thr Val Cys Ala
225                 230                 235                 240

Gly Gly Cys Ala Arg Cys Lys Gly Pro Leu Pro Thr Asp Cys Cys His
                245                 250                 255

Glu Gln Cys Ala Ala Gly Cys Thr Gly Pro Lys His Ser Asp Cys Leu
            260                 265                 270

Ala Cys Leu His Phe Asn His Ser Gly Ile Cys Glu Leu His Cys Pro
        275                 280                 285

Ala Leu Val Thr Tyr Asn Thr Asp Thr Phe Glu Ser Met Pro Asn Pro
290                 295                 300

Glu Gly Arg Tyr Thr Phe Gly Ala Ser Cys Val Thr Ala Cys Pro Tyr
305                 310                 315                 320

Asn Tyr Leu Ser Thr Asp Val Gly Ser Gly Ala Gly Gly Met Val His
                325                 330                 335

His Arg His Arg Ser Ser Ser Thr Arg Ser Gly Gly Gly Asp Leu Thr
            340                 345                 350

Leu Gly Leu Glu Pro Ser Glu Glu Ala Pro Arg Ser Pro Leu Ala
        355                 360                 365

Pro Ser Glu Gly Ala Gly Ser Asp Val Phe Asp Gly Asp Leu Gly Met
370                 375                 380

Gly Ala Ala Lys Gly Leu Gln Ser Leu Pro Thr His Asp Pro Ser Pro
385                 390                 395                 400

Leu Gln Arg Tyr Ser Glu Asp Pro Thr Val Pro Leu Pro Ser Glu Thr
            405                 410                 415

Asp Gly Tyr Val Ala Pro Leu Thr Cys Ser Pro Gln Pro Glu Tyr Val
            420                 425                 430

Asn Gln Pro Asp Val Arg Pro Gln Pro Pro Ser Pro Arg Glu Gly Pro
        435                 440                 445

Leu Pro Ala Ala Arg Pro Ala Gly Ala Thr Leu Glu Arg Ala Lys Thr
450                 455                 460

Leu Ser Pro Gly Lys Asn Gly Val Val Lys Asp Val Phe Ala Phe Gly
465                 470                 475                 480

Gly Ala Val Glu Asn Pro Glu Tyr Leu Thr Pro Gln Gly Gly Ala Ala
```

```
                         485                 490                 495
Pro Gln Pro His Pro Pro Ala Phe Ser Pro Ala Phe Asp Asn Leu
            500                 505                 510

Tyr Tyr Trp Asp Gln Asp Pro Glu Arg Gly Ala Pro Pro Ser Thr
            515                 520                 525

Phe Lys Gly Thr Pro Thr Ala Glu Asn Pro Glu Tyr Leu Gly Leu Asp
            530                 535                 540

Val Pro Ala Ala Ala Pro Ala Arg Ser Pro Ser Pro Ser Thr Gln Pro
545                 550                 555                 560

Trp Glu His Val Asn Ala Ile Gln Glu Ala Arg Arg Leu Leu Asn Leu
            565                 570                 575

Ser Arg Asp Thr Ala Ala Glu Met Asn Glu Thr Val Glu Val Ile Ser
            580                 585                 590

Glu Met Phe Asp Leu Gln Glu Pro Thr Cys Leu Gln Thr Arg Leu Glu
            595                 600                 605

Leu Tyr Lys Gln Gly Leu Arg Gly Ser Leu Thr Lys Leu Lys Gly Pro
            610                 615                 620

Leu Thr Met Met Ala Ser His Tyr Lys Gln His Cys Pro Pro Thr Pro
625                 630                 635                 640

Glu Thr Ser Cys Ala Thr Gln Ile Ile Thr Phe Glu Ser Phe Lys Glu
            645                 650                 655

Asn Leu Lys Asp Phe Leu Leu Val Ile Pro Phe Asp Cys Trp Glu Pro
            660                 665                 670

Val Gln Glu Gly Ala Pro Pro Pro Ala Ala Ala His His His His
            675                 680                 685

His His
    690

<210> SEQ ID NO 3
<211> LENGTH: 564
<212> TYPE: PRT
<213> ORGANISM: Artificial Sequence
<220> FEATURE:
<223> OTHER INFORMATION: HER500* construct

<400> SEQUENCE: 3

Met Arg Ala Ala Pro Leu Leu Leu Ala Arg Ala Ala Ser Leu Ser Leu
1               5                   10                  15

Gly Phe Leu Phe Leu Leu Phe Phe Trp Leu Asp Arg Ser Val Leu Ala
            20                  25                  30

Lys Glu Leu Ala Arg Gly Ala Ala Ser Thr Gln Val Cys Thr Gly Thr
            35                  40                  45

Asp Met Lys Leu Arg Leu Pro Ala Ser Pro Glu Thr His Leu Asp Met
            50                  55                  60

Leu Arg His Leu Tyr Gln Gly Cys Gln Val Val Gln Gly Asn Leu Glu
65                  70                  75                  80

Leu Thr Tyr Leu Pro Thr Asn Ala Ser Leu Ser Phe Leu Gln Asp Ile
            85                  90                  95

Gln Glu Val Gln Gly Tyr Val Leu Ile Ala His Asn Gln Val Arg Gln
            100                 105                 110

Val Pro Leu Gln Arg Leu Arg Ile Val Arg Gly Thr Gln Leu Phe Glu
            115                 120                 125

Asp Asn Tyr Ala Leu Ala Val Leu Asp Asn Gly Asp Pro Leu Asn Asn
            130                 135                 140

Thr Thr Pro Val Thr Gly Ala Ser Pro Gly Gly Leu Arg Glu Leu Gln
```

```
                                    -continued
145                 150                 155                 160

Leu Arg Ser Leu Thr Glu Ile Leu Lys Gly Gly Val Leu Ile Gln Arg
            165                 170                 175

Asn Pro Gln Leu Cys Tyr Gln Asp Thr Ile Leu Trp Lys Asp Ile Phe
            180                 185                 190

His Lys Asn Asn Gln Leu Ala Leu Thr Leu Ile Asp Thr Asn Arg Ser
            195                 200                 205

Arg Ala Cys His Pro Cys Ser Pro Met Cys Lys Gly Ser Arg Cys Trp
            210                 215                 220

Gly Glu Ser Ser Glu Asp Cys Gln Ser Leu Thr Arg Thr Val Cys Ala
225                 230                 235                 240

Gly Gly Cys Ala Arg Cys Lys Gly Pro Leu Pro Thr Asp Cys Cys His
            245                 250                 255

Glu Gln Cys Ala Ala Gly Cys Thr Gly Pro Lys His Ser Asp Cys Leu
            260                 265                 270

Ala Cys Leu His Phe Asn His Ser Gly Ile Cys Glu Leu His Cys Pro
            275                 280                 285

Ala Leu Val Thr Tyr Asn Thr Asp Thr Phe Glu Ser Met Pro Asn Pro
            290                 295                 300

Glu Gly Arg Tyr Thr Phe Gly Ala Ser Cys Val Thr Ala Cys Pro Tyr
305                 310                 315                 320

Asn Tyr Leu Ser Thr Asp Val Gly Ser Ala Ser Ile Ile Asn Phe Glu
            325                 330                 335

Lys Leu Gly Ala Gly Gly Met Val His His Arg His Arg Ser Ser Ser
            340                 345                 350

Thr Arg Ser Gly Gly Gly Asp Leu Thr Leu Gly Leu Glu Pro Ser Glu
            355                 360                 365

Glu Glu Ala Pro Arg Ser Pro Leu Ala Pro Ser Glu Gly Ala Gly Ser
            370                 375                 380

Asp Val Phe Asp Gly Asp Leu Gly Met Gly Ala Ala Lys Gly Leu Gln
385                 390                 395                 400

Ser Leu Pro Thr His Asp Pro Ser Pro Leu Gln Arg Tyr Ser Glu Asp
            405                 410                 415

Pro Thr Val Pro Leu Pro Ser Glu Thr Asp Gly Tyr Val Ala Pro Leu
            420                 425                 430

Thr Cys Ser Pro Gln Pro Glu Tyr Val Asn Gln Pro Asp Val Arg Pro
            435                 440                 445

Gln Pro Pro Ser Pro Arg Glu Gly Pro Leu Pro Ala Ala Arg Pro Ala
            450                 455                 460

Gly Ala Thr Leu Glu Arg Ala Lys Thr Leu Ser Pro Gly Lys Asn Gly
465                 470                 475                 480

Val Val Lys Asp Val Phe Ala Phe Gly Gly Ala Val Glu Asn Pro Glu
            485                 490                 495

Tyr Leu Thr Pro Gln Gly Gly Ala Ala Pro Gln Pro His Pro Pro Pro
            500                 505                 510

Ala Phe Ser Pro Ala Phe Asp Asn Leu Tyr Tyr Trp Asp Gln Asp Pro
            515                 520                 525

Pro Glu Arg Gly Ala Pro Pro Ser Thr Phe Lys Gly Thr Pro Thr Ala
            530                 535                 540

Glu Asn Pro Glu Tyr Leu Gly Leu Asp Val Pro Ala Ala His His
545                 550                 555                 560

His His His His
```

<210> SEQ ID NO 4
<211> LENGTH: 697
<212> TYPE: PRT
<213> ORGANISM: Artificial Sequence
<220> FEATURE:
<223> OTHER INFORMATION: HER500*-rGM-CSF construct

<400> SEQUENCE: 4

```
Met Arg Ala Ala Pro Leu Leu Leu Ala Arg Ala Ala Ser Leu Ser Leu
 1               5                  10                  15

Gly Phe Leu Phe Leu Leu Phe Phe Trp Leu Asp Arg Ser Val Leu Ala
                20                  25                  30

Lys Glu Leu Ala Arg Gly Ala Ala Ser Thr Gln Val Cys Thr Gly Thr
            35                  40                  45

Asp Met Lys Leu Arg Leu Pro Ala Ser Pro Glu Thr His Leu Asp Met
        50                  55                  60

Leu Arg His Leu Tyr Gln Gly Cys Gln Val Val Gln Gly Asn Leu Glu
    65                  70                  75                  80

Leu Thr Tyr Leu Pro Thr Asn Ala Ser Leu Ser Phe Leu Gln Asp Ile
                85                  90                  95

Gln Glu Val Gln Gly Tyr Val Leu Ile Ala His Asn Gln Val Arg Gln
               100                 105                 110

Val Pro Leu Gln Arg Leu Arg Ile Val Arg Gly Thr Gln Leu Phe Glu
           115                 120                 125

Asp Asn Tyr Ala Leu Ala Val Leu Asp Asn Gly Asp Pro Leu Asn Asn
       130                 135                 140

Thr Thr Pro Val Thr Gly Ala Ser Pro Gly Gly Leu Arg Glu Leu Gln
145                 150                 155                 160

Leu Arg Ser Leu Thr Glu Ile Leu Lys Gly Gly Val Leu Ile Gln Arg
               165                 170                 175

Asn Pro Gln Leu Cys Tyr Gln Asp Thr Ile Leu Trp Lys Asp Ile Phe
           180                 185                 190

His Lys Asn Asn Gln Leu Ala Leu Thr Leu Ile Asp Thr Asn Arg Ser
       195                 200                 205

Arg Ala Cys His Pro Cys Ser Pro Met Cys Lys Gly Ser Arg Cys Trp
   210                 215                 220

Gly Glu Ser Ser Glu Asp Cys Gln Ser Leu Thr Arg Thr Val Cys Ala
225                 230                 235                 240

Gly Gly Cys Ala Arg Cys Lys Gly Pro Leu Pro Thr Asp Cys Cys His
               245                 250                 255

Glu Gln Cys Ala Ala Gly Cys Thr Gly Pro Lys His Ser Asp Cys Leu
           260                 265                 270

Ala Cys Leu His Phe Asn His Ser Gly Ile Cys Glu Leu His Cys Pro
       275                 280                 285

Ala Leu Val Thr Tyr Asn Thr Asp Thr Phe Glu Ser Met Pro Asn Pro
   290                 295                 300

Glu Gly Arg Tyr Thr Phe Gly Ala Ser Cys Val Thr Ala Cys Pro Tyr
305                 310                 315                 320

Asn Tyr Leu Ser Thr Asp Val Gly Ser Ala Ser Ile Ile Asn Phe Glu
               325                 330                 335

Lys Leu Gly Ala Gly Gly Met Val His His Arg His Arg Ser Ser Ser
           340                 345                 350

Thr Arg Ser Gly Gly Gly Asp Leu Thr Leu Gly Leu Glu Pro Ser Glu
       355                 360                 365
```

```
Glu Glu Ala Pro Arg Ser Pro Leu Ala Pro Ser Glu Gly Ala Gly Ser
            370                 375                 380

Asp Val Phe Asp Gly Asp Leu Gly Met Gly Ala Ala Lys Gly Leu Gln
385                 390                 395                 400

Ser Leu Pro Thr His Asp Pro Ser Pro Leu Gln Arg Tyr Ser Glu Asp
                405                 410                 415

Pro Thr Val Pro Leu Pro Ser Glu Thr Asp Gly Tyr Val Ala Pro Leu
            420                 425                 430

Thr Cys Ser Pro Gln Pro Glu Tyr Val Asn Gln Pro Asp Val Arg Pro
            435                 440                 445

Gln Pro Pro Ser Pro Arg Glu Gly Pro Leu Pro Ala Ala Arg Pro Ala
    450                 455                 460

Gly Ala Thr Leu Glu Arg Ala Lys Thr Leu Ser Pro Gly Lys Asn Gly
465                 470                 475                 480

Val Val Lys Asp Val Phe Ala Phe Gly Gly Ala Val Glu Asn Pro Glu
                485                 490                 495

Tyr Leu Thr Pro Gln Gly Gly Ala Ala Pro Gln Pro His Pro Pro Pro
            500                 505                 510

Ala Phe Ser Pro Ala Phe Asp Asn Leu Tyr Tyr Trp Asp Gln Asp Pro
            515                 520                 525

Pro Glu Arg Gly Ala Pro Pro Ser Thr Phe Lys Gly Thr Pro Thr Ala
            530                 535                 540

Glu Asn Pro Glu Tyr Leu Gly Leu Asp Val Pro Ala Ala Ala Pro Thr
545                 550                 555                 560

Arg Ser Pro Asn Pro Val Thr Arg Pro Trp Lys His Val Asp Ala Ile
                565                 570                 575

Lys Glu Ala Leu Ser Leu Leu Asn Asp Met Arg Ala Leu Glu Asn Glu
            580                 585                 590

Lys Asn Glu Asp Val Asp Ile Ile Ser Asn Glu Phe Ser Ile Gln Arg
                595                 600                 605

Pro Thr Cys Val Gln Thr Arg Leu Lys Leu Tyr Lys Gln Gly Leu Arg
            610                 615                 620

Gly Asn Leu Thr Lys Leu Asn Gly Ala Leu Thr Met Ile Ala Ser His
625                 630                 635                 640

Tyr Gln Thr Asn Cys Pro Pro Thr Pro Glu Thr Asp Cys Glu Ile Glu
                645                 650                 655

Val Thr Thr Phe Glu Asp Phe Ile Lys Asn Leu Lys Gly Phe Leu Phe
            660                 665                 670

Asp Ile Pro Phe Asp Cys Trp Lys Pro Val Gln Lys Gly Ala Pro Pro
            675                 680                 685

Pro Pro Ala His His His His His
    690                 695

<210> SEQ ID NO 5
<211> LENGTH: 479
<212> TYPE: PRT
<213> ORGANISM: Artificial Sequence
<220> FEATURE:
<223> OTHER INFORMATION: HER300*-rGM-CSF construct

<400> SEQUENCE: 5

Met Arg Ala Ala Pro Leu Leu Leu Ala Arg Ala Ala Ser Leu Ser Leu
 1               5                  10                  15

Gly Phe Leu Phe Leu Leu Phe Phe Trp Leu Asp Arg Ser Val Leu Ala
             20                  25                  30
```

-continued

```
Lys Glu Leu Ala Arg Gly Ala Ala Ser Thr Gln Val Cys Thr Gly Thr
             35                  40                  45

Asp Met Lys Leu Arg Leu Pro Ala Ser Pro Glu Thr His Leu Asp Met
 50                  55                  60

Leu Arg His Leu Tyr Gln Gly Cys Gln Val Val Gln Gly Asn Leu Glu
 65                  70                  75                  80

Leu Thr Tyr Leu Pro Thr Asn Ala Ser Leu Ser Phe Leu Gln Asp Ile
                 85                  90                  95

Gln Glu Val Gln Gly Tyr Val Leu Ile Ala His Asn Gln Val Arg Gln
            100                 105                 110

Val Pro Leu Gln Arg Leu Arg Ile Val Arg Gly Thr Gln Leu Phe Glu
            115                 120                 125

Asp Asn Tyr Ala Leu Ala Val Leu Asp Asn Gly Asp Pro Leu Asn Asn
            130                 135                 140

Thr Thr Pro Val Thr Gly Ala Ser Pro Gly Gly Leu Arg Glu Leu Gln
145                 150                 155                 160

Leu Arg Ser Leu Thr Glu Ile Leu Lys Gly Gly Val Leu Ile Gln Arg
                165                 170                 175

Asn Pro Gln Leu Cys Tyr Gln Asp Thr Ile Leu Trp Lys Asp Ile Phe
            180                 185                 190

His Lys Asn Asn Gln Leu Ala Leu Thr Leu Ile Asp Thr Asn Arg Ser
            195                 200                 205

Arg Ala Cys His Pro Cys Ser Pro Met Cys Lys Gly Ser Arg Cys Trp
            210                 215                 220

Gly Glu Ser Ser Glu Asp Cys Gln Ser Leu Thr Arg Thr Val Cys Ala
225                 230                 235                 240

Gly Gly Cys Ala Arg Cys Lys Gly Pro Leu Pro Thr Asp Cys Cys His
                245                 250                 255

Glu Gln Cys Ala Ala Gly Cys Thr Gly Pro Lys His Ser Asp Cys Leu
            260                 265                 270

Ala Cys Leu His Phe Asn His Ser Gly Ile Cys Glu Leu His Cys Pro
            275                 280                 285

Ala Leu Val Thr Tyr Asn Thr Asp Thr Phe Glu Ser Met Pro Asn Pro
290                 295                 300

Glu Gly Arg Tyr Thr Phe Gly Ala Ser Cys Val Thr Ala Cys Pro Tyr
305                 310                 315                 320

Asn Tyr Leu Ser Thr Asp Val Gly Ser Ala Ser Ile Ile Asn Phe Glu
                325                 330                 335

Lys Leu Ala Ala Pro Thr Arg Ser Pro Asn Pro Val Thr Arg Pro Trp
            340                 345                 350

Lys His Val Asp Ala Ile Lys Glu Ala Leu Ser Leu Leu Asn Asp Met
            355                 360                 365

Arg Ala Leu Glu Asn Glu Lys Asn Glu Asp Val Asp Ile Ile Ser Asn
            370                 375                 380

Glu Phe Ser Ile Gln Arg Pro Thr Cys Val Gln Thr Arg Leu Lys Leu
385                 390                 395                 400

Tyr Lys Gln Gly Leu Arg Gly Asn Leu Thr Lys Leu Asn Gly Ala Leu
                405                 410                 415

Thr Met Ile Ala Ser His Tyr Gln Thr Asn Cys Pro Pro Thr Pro Glu
            420                 425                 430

Thr Asp Cys Glu Ile Glu Val Thr Thr Phe Glu Asp Phe Ile Lys Asn
            435                 440                 445

Leu Lys Gly Phe Leu Phe Asp Ile Pro Phe Asp Cys Trp Lys Pro Val
```

```
                450                 455                 460
Gln Lys Gly Ala Pro Pro Pro Ala His His His His His
465                 470                 475

<210> SEQ ID NO 6
<211> LENGTH: 1665
<212> TYPE: DNA
<213> ORGANISM: Artificial Sequence
<220> FEATURE:
<223> OTHER INFORMATION: HER500 construct

<400> SEQUENCE: 6
atgagagctg caccccctcct cctggccagg gcagcaagcc ttagccttgg cttcttgttt      60
ctgctttttt tctggctaga ccgaagtgta ctagccaagg agttggcgcg cggggccgcg     120
tcgacccaag tgtgcaccgg cacagacatg aagctgcggc tccctgccag tcccgagacc     180
cacctggaca tgctccgcca cctctaccag ggctgccagg tggtgcaggg aaacctggaa     240
ctcacctacc tgcccaccaa tgccagcctg tccttcctgc aggatatcca ggaggtgcag     300
ggctacgtgc tcatcgctca caaccaagtg aggcaggtcc cactgcagag gctgcggatt     360
gtgcgaggca cccagctctt tgaggacaac tatgccctgg ccgtgctaga caatggagac     420
ccgctgaaca taccacccc tgtcacaggg gcctccccag gaggcctgcg ggagctgcag     480
cttcgaagcc tcacagagat cttgaaagga gggtcttga tccagcggaa ccccagctc     540
tgctaccagg acgcgatttt gtggaaggac atcttccaca gaacaaccca gctggctctc     600
acactgatag acaccaaccg ctctcgggcc tgccacccct gttctccgat gtgtaagggc     660
tcccgctgct ggggagagag ttctgaggat tgtcagagcc tgacgcgcac tgtctgtgcc     720
ggtggctgtg cccgctgcaa ggggccactg cccactgact gctgccatga gcagtgtgct     780
gccggctgca gggcccccaa gcactctgac tgcctggcct gcctccactt caaccacagt     840
ggcatctgtg agctgcactg cccagcccctg gtcacctaca cacagacac gtttgagtcc     900
atgcccaatc ccgagggccg gtatacattc ggcgccagct gtgtgactgc ctgtccctac     960
aactaccttt ctacggacgt gggatcgggc gctgggggca tggtccacca caggcaccgc    1020
agctcatcta ccaggagtgg cggtggggac ctgacactag gctggagcc tctgaagag    1080
gaggcccca ggtctccact ggcacccctcc gaaggggctg gctccgatgt atttgatggt    1140
gacctgggaa tggggcagc caaggggctg caaagcctcc ccacacatga ccccagccct    1200
ctacagcggt acagtgagga ccccacagta cccctgccct ctgagactga tggctacgtt    1260
gccccccctga cctgcagccc ccagcctgaa tatgtgaacc agccagatgt tcggccccag    1320
cccccttcgc cccgagaggg ccctctgcct gctgcccgac tgctggtgc cactctggaa    1380
agggccaaga ctctctcccc aggaagaat ggggtcgtca agacgttttt tgcctttggg    1440
ggtgccgtgg agaaccccga gtacttgaca ccccagggag gagctgcccc tcagccccac    1500
cctcctcctg ccttcagccc agccttcgac aacctctatt actgggacca ggacccacca    1560
gagcgggggg ctccacccag cacctttcaaa gggacaccta cggcagagaa cccagagtac    1620
ctgggtctgg acgtgccagc ggccgcacat caccatcacc atcac                    1665

<210> SEQ ID NO 7
<211> LENGTH: 2070
<212> TYPE: DNA
<213> ORGANISM: Artificial Sequence
<220> FEATURE:
<223> OTHER INFORMATION: HER500-hGM-CSF construct
```

<400> SEQUENCE: 7

```
atgagagctg caccccctcct cctggccagg gcagcaagcc ttagccttgg cttcttgttt      60
ctgcttttt  tctggctaga ccgaagtgta ctagccaagg agttggcgcg cggggccgcg     120
tcgacccaag tgtgcaccgg cacagacatg aagctgcggc tccctgccag tcccgagacc     180
cacctggaca tgctccgcca cctctaccag ggctgccagg tggtcaggg  aaacctggaa     240
ctcacctacc tgcccaccaa tgccagcctg tccttcctgc aggatatcca ggaggtgcag     300
ggctacgtgc tcatcgctca aaccaagtg  aggcaggtcc cactgcagag gctgcggatt     360
gtgcgaggca cccagctctt tgaggacaac tatgccctgg ccgtgctaga caatggagac     420
ccgctgaaca ataccacccc tgtcacaggg gcctccccag gaggcctgcg ggagctgcag     480
cttcgaagcc tcacagagat cttgaaagga ggggtcttga tccagcggaa cccccagctc     540
tgctaccagg acacgatttt gtggaaggac atcttccaca gaacaaccca gctggctctc     600
acactgatag acaccaaccg ctctcgggcc tgccaccccct gttctccgat gtgtaagggc     660
tcccgctgct ggggagagag ttctgaggat tgtcagagcc tgacgcgcac tgtctgtgcc     720
ggtggctgtg cccgctgcaa ggggccactg cccactgact gctgccatga gcagtgtgct     780
gccggctgca cgggccccaa gcactctgac tgcctggcct gcctccactt caaccacagt     840
ggcatctgtg agctgcactg cccagccctg gtcacctaca cacagacac  gtttgagtcc     900
atgcccaatc ccgagggccg gtatacattc ggcgccagct gtgtgactgc ctgtccctac     960
aactaccttt ctacggacgt gggatcgggc gctgggggca tggtccacca caggcaccgc    1020
agctcatcta ccaggagtgg cggtggggac ctgacactag gctggagcc  ctctgaagag    1080
gaggccccca ggtctccact ggcaccctcc gaagggggctg gctccgatgt atttgatggt    1140
gacctgggaa tgggggcagc caaggggctg caaagcctcc ccacacatga ccccagccct    1200
ctacagcggt acagtgagga ccccacagta cccctgccct ctgagactga tggctacgtt    1260
gccccccctga cctgcagccc ccagcctgaa tatgtgaacc agccagatgt tcggccccag    1320
cccccttcgc cccgagaggg ccctctgcct gctgcccgac ctgctggtgc cactctggaa    1380
agggccaaga ctctctcccc aggaagaat  ggggtcgtca agacgttttt tgcctttggg    1440
ggtgccgtgg agaaccccga gtacttgaca ccccagggag gagctgcccc tcagccccac    1500
cctcctcctg ccttcagccc agccttcgac aacctctatt actgggacca ggacccacca    1560
gagcgggggg ctccacccag caccttcaaa gggacaccta cggcagagaa cccagagtac    1620
ctgggtctgg acgtgccagc ggccgcaccc gcccgctcgc ccagcccag  cacacagccc    1680
tgggagcatg tgaatgccat ccaggaggcc cggcgtctcc tgaacctgag tagagacact    1740
gctgctgaga tgaatgaaac agtagaagtc atctcagaaa tgtttgacct ccaggagccg    1800
acctgcctac agacccgcct ggagctgtac aagcagggcc tgcggggcag cctcaccaag    1860
ctcaagggcc ccttgaccat gatggccagc cactacaaaa agcactgccc tccaaccccg    1920
gaaacttcct gtgcaaccca gattatcacc tttgaaagtt tcaaagagaa cctgaaggac    1980
tttctgcttg tcatccccctt tgactgctgg gagccagtcc aggagggcgc gccacccccg    2040
ccggcggccg cacatcacca tcaccatcac                                      2070
```

<210> SEQ ID NO 8
<211> LENGTH: 1692
<212> TYPE: DNA
<213> ORGANISM: Artificial Sequence
<220> FEATURE:
<223> OTHER INFORMATION: HER500* construct

<400> SEQUENCE: 8

```
atgagagctg cacccctcct cctggccagg gcagcaagcc ttagccttgg cttcttgttt    60
ctgcttttt tctggctaga ccgaagtgta ctagccaagg agttggcgcg cggggccgcg   120
tcgacccaag tgtgcaccgg cacagacatg aagctgcggc tccctgccag tcccgagacc   180
cacctggaca tgctccgcca cctctaccag ggctgccagg tggtgcaggg aaacctggaa   240
ctcacctacc tgcccaccaa tgccagcctg tccttcctgc aggatatcca ggaggtgcag   300
ggctacgtgc tcatcgctca caaccaagtg aggcaggtcc cactgcagag gctgcggatt   360
gtgcgaggca cccagctctt tgaggacaac tatgccctgg ccgtgctaga caatggagac   420
ccgctgaaca ataccacccc tgtcacaggg gcctccccag gaggcctgcg ggagctgcag   480
cttcgaagcc tcacagagat cttgaaagga ggggtcttga tccagcggaa ccccccagctc   540
tgctaccagg acacgatttt gtggaaggac atcttccaca gaacaaccca gctggctctc   600
acactgatag acaccaaccg ctctcgggcc tgccacccct gttctccgat gtgtaagggc   660
tcccgctgct ggggagagag ttctgaggat tgtcagagcc tgacgcgcac tgtctgtgcc   720
ggtggctgtg cccgctgcaa ggggccactg cccactgact gctgccatga gcagtgtgct   780
gccggctgca cgggcccccaa gcactctgac tgcctggcct gcctccactt caaccacagt   840
ggcatctgtg agctgcactg cccagccctg gtcacctaca cacagacac gtttgagtcc   900
atgcccaatc ccgagggccg gtatacattc ggcgccagct gtgtgactgc ctgtccctac   960
aactaccttt ctacggacgt gggatccgct agcatcatta tttcgagaa gttgggcgct  1020
gggggcatgg tccaccacag gcaccgcagc tcatctacca ggagtggcgg tggggacctg  1080
acactagggc tggagccctc tgaagaggag gccccccaggt ctccactggc acctccgaa  1140
ggggctggct ccgatgtatt tgatggtgac ctgggaatgg gggcagccaa ggggctgcaa  1200
agcctcccca cacatgaccc cagccctcta cagcggtaca gtgaggaccc cacagtaccc  1260
ctgccctctg agactgatgg ctacgttgcc cccctgacct gcagccccca gcctgaatat  1320
gtgaaccagc cagatgttcg gccccagccc ccttcgcccc gagagggccc tctgcctgct  1380
gcccgacctg ctggtgccac tctggaaagg gccaagactc tctccccagg gaagaatggg  1440
gtcgtcaaag acgtttttgc ctttgggggt gccgtggaga accccgagta cttgacaccc  1500
cagggaggag ctgcccctca gccccaccct cctcctgcct tcagcccagc cttcgacaac  1560
ctctattact gggaccagga cccaccagag cgggggggctc cacccagcac cttcaaaggg  1620
acacctacgg cagagaaccc agagtacctg gtctggacg tgccagcggc cgcacatcac  1680
catcaccatc ac                                                      1692
```

<210> SEQ ID NO 9
<211> LENGTH: 2091
<212> TYPE: DNA
<213> ORGANISM: Artificial Sequence
<220> FEATURE:
<223> OTHER INFORMATION: HER500*-rGM-CSF construct

<400> SEQUENCE: 9

```
atgagagctg caccccctcct cctggccagg gcagcaagcc ttagccttgg cttcttgttt    60
ctgcttttt tctggctaga ccgaagtgta ctagccaagg agttggcgcg cggggccgcg   120
tcgacccaag tgtgcaccgg cacagacatg aagctgcggc tccctgccag tcccgagacc   180
cacctggaca tgctccgcca cctctaccag ggctgccagg tggtgcaggg aaacctggaa   240
```

-continued

| | |
|---|---|
| ctcacctacc tgcccaccaa tgccagcctg tccttcctgc aggatatcca ggaggtgcag | 300 |
| ggctacgtgc tcatcgctca caaccaagtg aggcaggtcc cactgcagag gctgcggatt | 360 |
| gtgcgaggca cccagctctt tgaggacaac tatgccctgg ccgtgctaga caatggagac | 420 |
| ccgctgaaca ataccacccc tgtcacaggg gcctcccag gaggcctgcg ggagctgcag | 480 |
| cttcgaagcc tcacagagat cttgaaagga ggggtcttga tccagcggaa ccccagctc | 540 |
| tgctaccagg acacgatttt gtggaaggac atcttccaca gaacaaccca gctggctctc | 600 |
| acactgatag acaccaaccg ctctcgggcc tgccacccct gttctccgat gtgtaagggc | 660 |
| tcccgctgct ggggagagag ttctgaggat tgtcagagcc tgacgcgcac tgtctgtgcc | 720 |
| ggtggctgtg cccgctgcaa ggggccactg cccactgact gctgccatga gcagtgtgct | 780 |
| gccggctgca cggcccccaa gcactctgac tgcctggcct gcctccactt caaccacagt | 840 |
| ggcatctgtg agctgcactg cccagccctg tcacctaca acacagacac gtttgagtcc | 900 |
| atgcccaatc ccgagggccg gtatacattc ggcgccagct gtgtgactgc ctgtcccctac | 960 |
| aactaccttt ctacggacgt gggatccgct agcatcatta atttcgagaa gttgggcgct | 1020 |
| gggggcatgg tccaccacag gcaccgcagc tcatctacca ggagtggcgg tggggacctg | 1080 |
| acactagggc tggagccctc tgaagaggag gcccccaggt ctccactggc accctccgaa | 1140 |
| ggggctggct ccgatgtatt tgatggtgac ctgggaatgg gggcagccaa ggggctgcaa | 1200 |
| agcctcccca cacatgaccc cagccctcta gcgcggtaca gtgaggaccc cacagtaccc | 1260 |
| ctgccctctg agactgatgg ctacgttgcc ccctgacct gcagccccca gcctgaatat | 1320 |
| gtgaaccagc cagatgttcg gccccagccc ccttcgcccc gagagggccc tctgcctgct | 1380 |
| gcccgacctg ctggtgccac tctggaaagg gccaagactc tctccccagg gaagaatggg | 1440 |
| gtcgtcaaag acgttttgc ctttggggt gccgtggaga ccccgagta cttgacaccc | 1500 |
| cagggaggag ctgcccctca gccccaccct cctcctgcct tcagcccagc cttcgacaac | 1560 |
| ctctattact gggaccagga cccaccagag cgggggctc cacccagcac cttcaaaggg | 1620 |
| acacctacgg cagagaaccc agagtacctg ggtctggacg tgccagcggc cgcccccacc | 1680 |
| cgctcaccca accctgtcac ccggccctgg aagcatgtag atgccatcaa agaagctctg | 1740 |
| agcctcctaa atgacatgcg tgctctggag aacgaaaaga cgaagacgt agacatcatc | 1800 |
| tctaatgagt tctccatcca gaggccgaca tgtgtgcaga cccgcctgaa gctatacaag | 1860 |
| cagggtctac ggggcaacct caccaaactc aatggcgcct tgaccatgat agccagccac | 1920 |
| taccagacga actgccctcc aacccggaa actgactgtg aaatagaagt caccacctt | 1980 |
| gaggatttca taaagaacct taaaggcttt ctgtttgata tccttttga ctgctggaag | 2040 |
| ccggtccaga aaggcgcgcc accccgccg gcgcatcacc atcaccatca c | 2091 |

<210> SEQ ID NO 10
<211> LENGTH: 1437
<212> TYPE: DNA
<213> ORGANISM: Artificial Sequence
<220> FEATURE:
<223> OTHER INFORMATION: HER300*rGM-CSF construct

<400> SEQUENCE: 10

| | |
|---|---|
| atgagagctg caccctcct cctggccagg gcagcaagcc ttagccttgg cttcttgttt | 60 |
| ctgcttttt tctggctaga ccgaagtgta ctagccaagg agttggcgcg cggggccgcg | 120 |
| tcgacccaag tgtgcaccgg cacagacatg aagctgcggc tccctgccag tcccgagacc | 180 |
| cacctggaca tgctccgcca cctctaccag ggctgccagg tggtgcaggg aaacctggaa | 240 |

```
ctcacctacc tgcccaccaa tgccagcctg tccttcctgc aggatatcca ggaggtgcag        300
ggctacgtgc tcatcgctca caaccaagtg aggcaggtcc cactgcagag gctgcggatt        360
gtgcgaggca cccagctctt tgaggacaac tatgccctgg ccgtgctaga caatggagac        420
ccgctgaaca ataccacccc tgtcacaggg gcctccccag gaggcctgcg ggagctgcag        480
cttcgaagcc tcacagagat cttgaaagga ggggtcttga tccagcggaa ccccagctc         540 tgctaccagg acacgatttt gtggaaggac atcttccaca gaacaaccca gctggctctc        600
acactgatag acaccaaccg ctctcgggcc tgccaccct gttctccgat gtgtaagggc         660
tcccgctgct ggggagagag ttctgaggat tgtcagagcc tgacgcgcac tgtctgtgcc        720
ggtggctgtg cccgctgcaa ggggccactg cccactgact gctgccatga gcagtgtgct        780
gccggctgca cgggccccaa gcactctgac tgcctggcct gcctccactt caaccacagt        840
ggcatctgtg agctgcactg cccagccctg gtcacctaca acacagacac gtttgagtcc        900
atgcccaatc ccgagggccg gtatacattc ggcgccagct gtgtgactgc ctgtccctac        960
aactaccttt ctacggacgt gggatccgct agcatcatta tttcgagaa gttggccgcc       1020 cccacccgct cacccaaccc tgtcacccgg ccctggaagc atgtagatgc catcaaagaa       1080
gctctgagcc tcctaaatga catgcgtgct ctggagaacg aaaagaacga agacgtagac       1140
atcatctcta atgagttctc catccagagg ccgacatgtg tgcagacccg cctgaagcta       1200
tacaagcagg gtctacgggg caacctcacc aaactcaatg gcgccttgac catgatagcc       1260
agccactacc agacgaactg ccctccaacc ccggaaactg actgtgaaat agaagtcacc       1320
acctttgagg atttcataaa gaaccttaaa ggctttctgt ttgatatccc ttttgactgc       1380
tggaagccgg tccagaaagg cgcgccaccc ccgccggcgc atcaccatca ccatcac        1437

<210> SEQ ID NO 11
<211> LENGTH: 32
<212> TYPE: PRT
<213> ORGANISM: Homo sapiens

<400> SEQUENCE: 11

Met Arg Ala Ala Pro Leu Leu Leu Ala Arg Ala Ala Ser Leu Ser Leu
1               5                   10                  15

Gly Phe Leu Phe Leu Leu Phe Phe Trp Leu Asp Arg Ser Val Leu Ala
            20                  25                  30

<210> SEQ ID NO 12
<211> LENGTH: 3
<212> TYPE: PRT
<213> ORGANISM: Homo sapiens

<400> SEQUENCE: 12

Lys Glu Leu
1

<210> SEQ ID NO 13
<211> LENGTH: 3
<212> TYPE: PRT
<213> ORGANISM: Homo sapiens

<400> SEQUENCE: 13

Gly Ala Ala
1

<210> SEQ ID NO 14
```

```
<211> LENGTH: 2
<212> TYPE: PRT
<213> ORGANISM: Artificial Sequence
<220> FEATURE:
<223> OTHER INFORMATION: linker

<400> SEQUENCE: 14

Ala Arg
 1

<210> SEQ ID NO 15
<211> LENGTH: 9
<212> TYPE: PRT
<213> ORGANISM: Artificial Sequence
<220> FEATURE:
<223> OTHER INFORMATION: C-terminal sequence of HER500 and HER500*
      constructs

<400> SEQUENCE: 15

Ala Ala Ala His His His His His His
 1               5

<210> SEQ ID NO 16
<211> LENGTH: 15
<212> TYPE: PRT
<213> ORGANISM: Artificial Sequence
<220> FEATURE:
<223> OTHER INFORMATION: C-terminal sequence of HER500-hGM-CSF construct

<400> SEQUENCE: 16

Gly Ala Pro Pro Pro Pro Ala Ala Ala His His His His His His
 1               5                  10                  15

<210> SEQ ID NO 17
<211> LENGTH: 13
<212> TYPE: PRT
<213> ORGANISM: Artificial Sequence
<220> FEATURE:
<223> OTHER INFORMATION: C-terminal sequence of HER500* and HER300* rat
      GM-CSF constructs

<400> SEQUENCE: 17

Gly Ala Pro Pro Pro Pro Ala His His His His His His
 1               5                  10

<210> SEQ ID NO 18
<211> LENGTH: 127
<212> TYPE: PRT
<213> ORGANISM: Homo sapiens

<400> SEQUENCE: 18

Ala Pro Ala Arg Ser Pro Ser Pro Ser Thr Gln Pro Trp Glu His Val
 1               5                  10                  15

Asn Ala Ile Gln Glu Ala Arg Arg Leu Leu Asn Leu Ser Arg Asp Thr
             20                  25                  30

Ala Ala Glu Met Asn Glu Thr Val Glu Val Ile Ser Glu Met Phe Asp
         35                  40                  45

Leu Gln Glu Pro Thr Cys Leu Gln Thr Arg Leu Glu Leu Tyr Lys Gln
     50                  55                  60

Gly Leu Arg Gly Ser Leu Thr Lys Leu Lys Gly Pro Leu Thr Met Met
 65                  70                  75                  80

Ala Ser His Tyr Lys Gln His Cys Pro Pro Thr Pro Glu Thr Ser Cys
                 85                  90                  95

Ala Thr Gln Ile Ile Thr Phe Glu Ser Phe Lys Glu Asn Leu Lys Asp
```

```
                        100                 105                 110
Phe Leu Leu Val Ile Pro Phe Asp Cys Trp Glu Pro Val Gln Glu
        115                 120                 125

<210> SEQ ID NO 19
<211> LENGTH: 381
<212> TYPE: DNA
<213> ORGANISM: Homo sapiens

<400> SEQUENCE: 19
gcacccgccc gctcgcccag ccccagcacg cagccctggg agcatgtgaa tgccatccag      60
gaggcccggc gtctcctgaa cctgagtaga gacactgctg ctgagatgaa tgaaacagta     120
gaagtcatct cagaaatgtt tgacctccag gagccgacct gcctacagac ccgcctggag     180
ctgtacaagc agggcctgcg gggcagcctc accaagctca agggccccctt gaccatgatg    240 gccagccact acaagcagca ctgccctcca accccggaaa cttcctgtgc aacccagact     300
atcacctttg aaagtttcaa agagaacctg aaggactttc tgcttgtcat ccccttttgac   360 tgctgggagc cagtccagga g                                               381

<210> SEQ ID NO 20
<211> LENGTH: 127
<212> TYPE: PRT
<213> ORGANISM: Rattus norvegicus

<400> SEQUENCE: 20

Ala Pro Thr Arg Ser Pro Asn Pro Val Thr Arg Pro Trp Lys His Val
 1               5                  10                  15

Asp Ala Ile Lys Glu Ala Leu Ser Leu Leu Asn Asp Met Arg Ala Leu
            20                  25                  30

Glu Asn Glu Lys Asn Glu Asp Val Asp Ile Ile Ser Asn Glu Phe Ser
        35                  40                  45

Ile Gln Arg Pro Thr Cys Val Gln Thr Arg Leu Lys Leu Tyr Lys Gln
    50                  55                  60

Gly Leu Arg Gly Asn Leu Thr Lys Leu Asn Gly Ala Leu Thr Met Ile
65                  70                  75                  80

Ala Ser His Tyr Gln Thr Asn Cys Pro Pro Thr Pro Glu Thr Asp Cys
                85                  90                  95

Glu Ile Glu Val Thr Thr Phe Glu Asp Phe Ile Lys Asn Leu Lys Gly
            100                 105                 110

Phe Leu Phe Asp Ile Pro Phe Asp Cys Trp Lys Pro Val Gln Lys
        115                 120                 125

<210> SEQ ID NO 21
<211> LENGTH: 381
<212> TYPE: DNA
<213> ORGANISM: Rattus norvegicus

<400> SEQUENCE: 21
gcacccaccc gctcacccaa ccctgtcacc cggccctgga agcatgtaga tgccatcaaa      60
gaagctctga gcctcctaaa tgacatgcgt gctctggaga acgaaaagaa cgaagacgta     120
gacatcatct ctaatgagtt ctccatccag aggccgacat gtgtgcagac ccgcctgaag    180
ctatacaagc agggtctacg gggcaacctc accaaactca atggcgcctt gaccatgata     240
gccagccact accagacgaa ctgccctcca accccggaaa ctgactgtga aatagaagtc     300
accacctttg aggatttcat aaagaacctt aaaggctttc tgtttgatat cccttttgac    360
```
tgctggaagc cggtccagaa a                                                381

<210> SEQ ID NO 22
<211> LENGTH: 8
<212> TYPE: PRT
<213> ORGANISM: Artificial Sequence
<220> FEATURE:
<223> OTHER INFORMATION: OVA-derived immunodominant octapeptide

<400> SEQUENCE: 22

Ser Ile Ile Asn Phe Glu Lys Leu
 1               5

<210> SEQ ID NO 23
<211> LENGTH: 289
<212> TYPE: PRT
<213> ORGANISM: Homo sapiens

<400> SEQUENCE: 23

Ser Thr Gln Val Cys Thr Gly Thr Asp Met Lys Leu Arg Leu Pro Ala
 1               5                   10                  15

Ser Pro Glu Thr His Leu Asp Met Leu Arg His Leu Tyr Gln Gly Cys
                20                  25                  30

Gln Val Val Gln Gly Asn Leu Glu Leu Thr Tyr Leu Pro Thr Asn Ala
            35                  40                  45

Ser Leu Ser Phe Leu Gln Asp Ile Gln Glu Val Gln Gly Tyr Val Leu
        50                  55                  60

Ile Ala His Asn Gln Val Arg Gln Val Pro Leu Gln Arg Leu Arg Ile
65                  70                  75                  80

Val Arg Gly Thr Gln Leu Phe Glu Asp Asn Tyr Ala Leu Ala Val Leu
                85                  90                  95

Asp Asn Gly Asp Pro Leu Asn Asn Thr Thr Pro Val Thr Gly Ala Ser
            100                 105                 110

Pro Gly Gly Leu Arg Glu Leu Gln Leu Arg Ser Leu Thr Glu Ile Leu
        115                 120                 125

Lys Gly Gly Val Leu Ile Gln Arg Asn Pro Gln Leu Cys Tyr Gln Asp
130                 135                 140

Thr Ile Leu Trp Lys Asp Ile Phe His Lys Asn Asn Gln Leu Ala Leu
145                 150                 155                 160

Thr Leu Ile Asp Thr Asn Arg Ser Arg Ala Cys His Pro Cys Ser Pro
                165                 170                 175

Met Cys Lys Gly Ser Arg Cys Trp Gly Glu Ser Ser Glu Asp Cys Gln
            180                 185                 190

Ser Leu Thr Arg Thr Val Cys Ala Gly Gly Cys Ala Arg Cys Lys Gly
        195                 200                 205

Pro Leu Pro Thr Asp Cys Cys His Glu Gln Cys Ala Ala Gly Cys Thr
210                 215                 220

Gly Pro Lys His Ser Asp Cys Leu Ala Cys Leu His Phe Asn His Ser
225                 230                 235                 240

Gly Ile Cys Glu Leu His Cys Pro Ala Leu Val Thr Tyr Asn Thr Asp
                245                 250                 255

Thr Phe Glu Ser Met Pro Asn Pro Glu Gly Arg Tyr Thr Phe Gly Ala
            260                 265                 270

Ser Cys Val Thr Ala Cys Pro Tyr Asn Tyr Leu Ser Thr Asp Val Gly
        275                 280                 285

Ser

<210> SEQ ID NO 24
<211> LENGTH: 867
<212> TYPE: DNA
<213> ORGANISM: Homo sapiens

<400> SEQUENCE: 24

| | | | | | |
|---|---|---|---|---|---|
| agcacccaag | tgtgcaccgg | cacagacatg | aagctgcggc | tccctgccag | tcccgagacc | 60 |
| cacctggaca | tgctccgcca | cctctaccag | ggctgccagg | tggtgcaggg | aaacctggaa | 120 |
| ctcacctacc | tgcccaccaa | tgccagcctg | tccttcctgc | aggatatcca | ggaggtgcag | 180 |
| ggctacgtgc | tcatcgctca | caaccaagtg | aggcaggtcc | cactgcagag | gctgcggatt | 240 |
| gtgcgaggca | cccagctctt | tgaggacaac | tatgccctgg | ccgtgctaga | caatggagac | 300 |
| ccgctgaaca | taccaccccc | tgtcacaggg | gcctccccag | gaggcctgcg | ggagctgcag | 360 |
| cttcgaagcc | tcacagagat | cttgaaagga | ggggtcttga | tccagcggaa | ccccagctc | 420 |
| tgctaccagg | acgcgatttt | gtggaaggac | atcttccaca | gaacaaccca | gctggctctc | 480 |
| acactgatag | acaccaaccg | ctctcgggcc | tgccacccct | gttctccgat | gtgtaagggc | 540 |
| tcccgctgct | ggggagagag | ttctgaggat | tgtcagagcc | tgacgcgcac | tgtctgtgcc | 600 |
| ggtggctgtg | cccgctgcaa | ggggccactg | cccactgact | gctgccatga | gcagtgtgct | 660 |
| gccggctgca | cggcccccaa | gcactctgac | tgcctggcct | gcctccactt | caaccacagt | 720 |
| ggcatctgtg | agctgcactg | cccagccctg | gtcacctaca | acacagacac | gtttgagtcc | 780 |
| atgcccaatc | ccgagggccg | gtatacattc | ggcgccagct | gtgtgactgc | ctgtccctac | 840 |
| aactaccttt | ctacggacgt | gggatcc | | | | 867 |

<210> SEQ ID NO 25
<211> LENGTH: 217
<212> TYPE: PRT
<213> ORGANISM: Homo sapiens

<400> SEQUENCE: 25

Gly Ala Gly Gly Met Val His Arg His Arg Ser Ser Ser Thr Arg
1               5                   10                  15

Ser Gly Gly Gly Asp Leu Thr Leu Gly Leu Glu Pro Ser Glu Glu
            20                  25                  30

Ala Pro Arg Ser Pro Leu Ala Pro Ser Glu Gly Ala Gly Ser Asp Val
        35                  40                  45

Phe Asp Gly Asp Leu Gly Met Gly Ala Ala Lys Gly Leu Gln Ser Leu
    50                  55                  60

Pro Thr His Asp Pro Ser Pro Leu Gln Arg Tyr Ser Glu Asp Pro Thr
65                  70                  75                  80

Val Pro Leu Pro Ser Glu Thr Asp Gly Tyr Val Ala Pro Leu Thr Cys
                85                  90                  95

Ser Pro Gln Pro Glu Tyr Val Asn Gln Pro Asp Val Arg Pro Gln Pro
            100                 105                 110

Pro Ser Pro Arg Glu Gly Pro Leu Pro Ala Ala Arg Pro Ala Gly Ala
        115                 120                 125

Thr Leu Glu Arg Ala Lys Thr Leu Ser Pro Gly Lys Asn Gly Val Val
    130                 135                 140

Lys Asp Val Phe Ala Phe Gly Gly Ala Val Glu Asn Pro Glu Tyr Leu
145                 150                 155                 160

Thr Pro Gln Gly Gly Ala Ala Pro Gln Pro His Pro Pro Pro Ala Phe
                165                 170                 175

-continued

```
Ser Pro Ala Phe Asp Asn Leu Tyr Tyr Trp Asp Gln Asp Pro Pro Glu
            180                 185                 190

Arg Gly Ala Pro Pro Ser Thr Phe Lys Gly Thr Pro Thr Ala Glu Asn
        195                 200                 205

Pro Glu Tyr Leu Gly Leu Asp Val Pro
    210                 215

<210> SEQ ID NO 26
<211> LENGTH: 651
<212> TYPE: DNA
<213> ORGANISM: Homo sapiens

<400> SEQUENCE: 26
ggcgctgggg gcatggtcca ccacaggcac cgcagctcat ctaccaggag tggcggtggg      60
gacctgacac tagggctgga gccctctgaa gaggaggccc ccaggtctcc actggcaccc     120
tccgaagggg ctggctccga tgtatttgat ggtgacctgg aatgggggc agccaagggg     180 ctgcaaagcc tccccacaca tgaccccagc cctctacagc ggtacagtga ggaccccaca     240 gtaccccctgc cctctgagac tgatggctac gttgccccccc tgacctgcag ccccagcct     300 gaatatgtga accagccaga tgttcggccc cagccccctt cgccccgaga gggccctctg     360
cctgctgccc gacctgctgg tgccactctg gaaagggcca agactctctc cccagggaag     420 aatgggtcg tcaaagacgt tttggccttt gggggtgccg tggagaaccc cgagtacttg     480
acaccccagg gaggagctgc ccctcagccc caccctcctc ctgccttcag cccagccttc     540
gacaacctct attactggga ccaggaccca ccagagcggg gggctccacc cagcaccttc     600
aaagggacac tacggcagaa gaacccagag tacctgggtc tggacgtgcc a              651

<210> SEQ ID NO 27
<211> LENGTH: 397
<212> TYPE: PRT
<213> ORGANISM: Artificial Sequence
<220> FEATURE:
<223> OTHER INFORMATION: NY-ESO-IC tumor antigen

<400> SEQUENCE: 27

Met Gln Ala Glu Gly Arg Gly Thr Gly Gly Ser Thr Gly Asp Ala Asp
  1               5                  10                  15

Gly Pro Gly Gly Pro Gly Ile Pro Asp Gly Pro Gly Gly Asn Ala Gly
             20                  25                  30

Gly Pro Gly Glu Ala Gly Ala Thr Gly Gly Arg Gly Pro Arg Gly Ala
         35                  40                  45

Gly Ala Ala Arg Ala Ser Gly Pro Gly Gly Gly Ala Pro Arg Gly Pro
     50                  55                  60

His Gly Gly Ala Ala Ser Gly Leu Asn Gly Cys Cys Arg Cys Gly Ala
 65                  70                  75                  80

Arg Gly Pro Glu Ser Arg Leu Leu Glu Phe Tyr Leu Ala Met Pro Phe
                 85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160
```

```
Trp Ile Thr Gln Cys Phe Leu Pro Val Phe Leu Ala Gln Pro Pro Ser
                165                 170                 175
Gly Gln Arg Arg Gly Ala Gly Met Val His Arg His Arg Ser
            180                 185                 190
Ser Ser Thr Arg Ser Gly Gly Asp Leu Thr Leu Gly Leu Glu Pro
        195                 200                 205
Ser Glu Glu Ala Pro Arg Ser Pro Leu Ala Pro Ser Glu Gly Ala
    210                 215                 220
Gly Ser Asp Val Phe Asp Gly Asp Leu Gly Met Gly Ala Ala Lys Gly
225                 230                 235                 240
Leu Gln Ser Leu Pro Thr His Asp Pro Ser Pro Leu Gln Arg Tyr Ser
                245                 250                 255
Glu Asp Pro Thr Val Pro Leu Pro Ser Glu Thr Asp Gly Tyr Val Ala
            260                 265                 270
Pro Leu Thr Cys Ser Pro Gln Pro Glu Tyr Val Asn Gln Pro Asp Val
        275                 280                 285
Arg Pro Gln Pro Pro Ser Pro Arg Glu Gly Pro Leu Pro Ala Ala Arg
    290                 295                 300
Pro Ala Gly Ala Thr Leu Glu Arg Ala Lys Thr Leu Ser Pro Gly Lys
305                 310                 315                 320
Asn Gly Val Val Lys Asp Val Phe Ala Phe Gly Gly Ala Val Glu Asn
                325                 330                 335
Pro Glu Tyr Leu Thr Pro Gln Gly Gly Ala Ala Pro Gln Pro His Pro
            340                 345                 350
Pro Pro Ala Phe Ser Pro Ala Phe Asp Asn Leu Tyr Tyr Trp Asp Gln
        355                 360                 365
Asp Pro Pro Glu Arg Gly Ala Pro Pro Ser Thr Phe Lys Gly Thr Pro
    370                 375                 380
Thr Ala Glu Asn Pro Glu Tyr Leu Gly Leu Asp Val Pro
385                 390                 395

<210> SEQ ID NO 28
<211> LENGTH: 1191
<212> TYPE: DNA
<213> ORGANISM: Artificial Sequence
<220> FEATURE:
<223> OTHER INFORMATION: NY-ESO-IC tumor antigen

<400> SEQUENCE: 28
atgcaggccg aaggccgggg cacagggggt cgacgggcg atgctgatgg cccaggaggc      60
cctggcattc ctgatggccc aggggggcaat gctggcggcc caggagaggc gggtgccacg    120
ggcggcagag gtccccgggg cgcaggggca gcaagggcct cggggccggg aggaggcgcc    180
ccgcggggtc gcatggcgg cgcggcttca gggctgaatg gatgctgcag atgcggggcc     240 aggggggccgg agaccgcct gcttgagttc tacctcgcca tgcctttcgc gacacccatg     300
gaagcagagc tggcccgcag gagcctggcc caggatgccc accgcttcc cgtgccaggg    360 gtgcttctga aggagttcac tgtgtccggc aacatactga ctatccgact gactgctgca    420
gaccaccgcc aactgcagct ctccatcagc tcctgtctcc agcagctttc cctgttgatg    480
tggatcacgc agtgctttct gcccgtgttt ttggctcagc ctcccctcagg gcagaggcgc    540 ggcgctgggg gcatggtcca ccacaggcac cgcagctcat ctaccaggag tggcggtggg    600
gacctgacac tagggctgga gccctctgaa gaggaggccc ccaggtctcc actggcaccc    660
tccgaagggg ctggctccga tgtatttgat ggtgaccctgg gaatgggggc agccaagggg    720
```

```
ctgcaaagcc tccccacaca tgaccccagc cctctacagc ggtacagtga ggaccccaca    780
gtacccctgc cctctgagac tgatggctac gttgccccccc tgacctgcag cccccagcct    840
gaatatgtga accagccaga tgttcggccc cagccccctt cgccccgaga gggccctctg    900
cctgctgccc gacctgctgg tgccactctg gaaagggcca agactctctc cccagggaag    960
aatggggtcg tcaaagacgt ttttgccttt gggggtgccg tggagaaccc cgagtacttg   1020 acccccagg gaggagctgc ccctcagccc caccctcctc ctgccttcag cccagccttc   1080
gacaacctct attactggga ccaggaccca ccagagcggg gggctccacc cagcaccttc   1140
aaagggacac tacggcagag aacccagag tacctgggtc tggacgtgcc a            1191
```

<210> SEQ ID NO 29
<211> LENGTH: 1179
<212> TYPE: PRT
<213> ORGANISM: Artificial Sequence
<220> FEATURE:
<223> OTHER INFORMATION: SART-3-IC

<400> SEQUENCE: 29

```
Met Ala Thr Ala Ala Glu Thr Ser Ala Ser Glu Pro Glu Ala Glu Ser
 1               5                  10                  15

Lys Ala Gly Pro Lys Ala Asp Gly Glu Glu Asp Glu Val Lys Ala Ala
                20                  25                  30

Arg Thr Arg Arg Lys Val Leu Ser Arg Ala Val Ala Ala Ala Thr Tyr
            35                  40                  45

Lys Thr Met Gly Pro Ala Trp Asp Gln Gln Glu Gly Val Ser Glu
    50                  55                  60

Ser Asp Gly Asp Glu Tyr Ala Met Ala Ser Ser Ala Glu Ser Ser Pro
65                  70                  75                  80

Gly Glu Tyr Glu Trp Glu Tyr Asp Glu Glu Glu Lys Asn Gln Leu
                85                  90                  95

Glu Ile Glu Arg Leu Glu Glu Gln Leu Ser Ile Asn Val Tyr Asp Tyr
            100                 105                 110

Asn Cys His Val Asp Leu Ile Arg Leu Leu Arg Leu Glu Gly Glu Leu
        115                 120                 125

Thr Lys Val Arg Met Ala Arg Gln Lys Met Ser Glu Ile Phe Pro Leu
    130                 135                 140

Thr Glu Glu Leu Trp Leu Glu Trp Leu His Asp Glu Ile Ser Met Ala
145                 150                 155                 160

Gln Asp Gly Leu Asp Arg Glu His Val Tyr Asp Leu Phe Glu Lys Ala
                165                 170                 175

Val Lys Asp Tyr Ile Cys Pro Asn Ile Trp Leu Glu Tyr Gly Gln Tyr
            180                 185                 190

Ser Val Gly Gly Ile Gly Gln Lys Gly Gly Leu Glu Lys Val Arg Ser
        195                 200                 205

Val Phe Glu Arg Ala Leu Ser Ser Val Gly Leu His Met Thr Lys Gly
    210                 215                 220

Leu Ala Leu Trp Glu Ala Tyr Arg Glu Phe Glu Ser Ala Ile Val Glu
225                 230                 235                 240

Ala Ala Arg Leu Glu Lys Val His Ser Leu Phe Arg Arg Gln Leu Ala
                245                 250                 255

Ile Pro Leu Tyr Asp Met Glu Ala Thr Phe Ala Glu Tyr Glu Glu Trp
            260                 265                 270

Ser Glu Asp Pro Ile Pro Glu Ser Val Ile Gln Asn Tyr Asn Lys Ala
        275                 280                 285
```

-continued

```
Leu Gln Gln Leu Glu Lys Tyr Lys Pro Tyr Glu Glu Ala Leu Leu Gln
    290                 295                 300
Ala Glu Ala Pro Arg Leu Ala Glu Tyr Gln Ala Tyr Ile Asp Phe Glu
305                 310                 315                 320
Met Lys Ile Gly Asp Pro Ala Arg Ile Gln Leu Ile Phe Glu Arg Ala
                325                 330                 335
Leu Val Glu Asn Cys Leu Val Pro Asp Leu Trp Ile Arg Tyr Ser Gln
            340                 345                 350
Tyr Leu Asp Arg Gln Leu Lys Val Lys Asp Leu Val Leu Ser Val His
        355                 360                 365
Asn Arg Ala Ile Arg Asn Cys Pro Trp Thr Val Ala Leu Trp Ser Arg
    370                 375                 380
Tyr Leu Leu Ala Met Glu Arg His Gly Val Asp His Gln Val Ile Ser
385                 390                 395                 400
Val Thr Phe Glu Lys Ala Leu Asn Ala Gly Phe Ile Gln Ala Thr Asp
                405                 410                 415
Tyr Val Glu Ile Trp Gln Ala Tyr Leu Asp Tyr Leu Arg Arg Arg Val
            420                 425                 430
Asp Phe Lys Gln Asp Ser Ser Lys Glu Leu Glu Leu Arg Ala Ala
        435                 440                 445
Phe Thr Arg Ala Leu Glu Tyr Leu Lys Gln Glu Val Glu Glu Arg Phe
    450                 455                 460
Asn Glu Ser Gly Asp Pro Ser Cys Val Ile Met Gln Asn Trp Ala Arg
465                 470                 475                 480
Ile Glu Ala Arg Leu Cys Asn Asn Met Gln Lys Ala Arg Glu Leu Trp
                485                 490                 495
Asp Ser Ile Met Thr Arg Gly Asn Ala Lys Tyr Ala Asn Met Trp Leu
            500                 505                 510
Glu Tyr Tyr Asn Leu Glu Arg Ala His Gly Asp Thr Gln His Cys Arg
        515                 520                 525
Lys Ala Leu His Arg Ala Val Gln Cys Thr Ser Asp Tyr Pro Glu His
    530                 535                 540
Val Cys Glu Val Leu Leu Thr Met Glu Arg Thr Glu Gly Ser Leu Glu
545                 550                 555                 560
Asp Trp Asp Ile Ala Val Gln Lys Thr Glu Thr Arg Leu Ala Arg Val
                565                 570                 575
Asn Glu Gln Arg Met Lys Ala Ala Glu Lys Ala Ala Leu Val Gln
            580                 585                 590
Gln Glu Glu Glu Lys Ala Glu Gln Arg Lys Ala Arg Ala Glu Lys
        595                 600                 605
Lys Ala Leu Lys Lys Lys Lys Ile Arg Gly Pro Glu Lys Arg Gly
    610                 615                 620
Ala Asp Glu Asp Glu Lys Glu Trp Gly Asp Asp Glu Glu Glu Gln
625                 630                 635                 640
Pro Ser Lys Arg Arg Arg Val Glu Asn Ser Ile Pro Ala Ala Gly Glu
                645                 650                 655
Thr Gln Asn Val Glu Val Ala Ala Gly Pro Ala Gly Lys Cys Ala Ala
            660                 665                 670
Val Asp Val Glu Pro Pro Ser Lys Gln Lys Glu Lys Ala Ala Ser Leu
        675                 680                 685
Lys Arg Asp Met Pro Lys Val Leu His Asp Ser Ser Lys Asp Ser Ile
    690                 695                 700
```

-continued

```
Thr Val Phe Val Ser Asn Leu Pro Tyr Ser Met Gln Glu Pro Asp Thr
705                 710                 715                 720

Lys Leu Arg Pro Leu Phe Glu Ala Cys Gly Glu Val Val Gln Ile Arg
                725                 730                 735

Pro Ile Phe Ser Asn Arg Gly Asp Phe Arg Gly Tyr Cys Tyr Val Glu
            740                 745                 750

Phe Lys Glu Glu Lys Ser Ala Leu Gln Ala Leu Glu Met Asp Arg Lys
        755                 760                 765

Ser Val Glu Gly Arg Pro Met Phe Val Ser Pro Cys Val Asp Lys Ser
    770                 775                 780

Lys Asn Pro Asp Phe Lys Val Phe Arg Tyr Ser Thr Ser Leu Glu Lys
785                 790                 795                 800

His Lys Leu Phe Ile Ser Gly Leu Pro Phe Ser Cys Thr Lys Glu Glu
                805                 810                 815

Leu Glu Glu Ile Cys Lys Ala His Gly Thr Val Lys Asp Leu Arg Leu
            820                 825                 830

Val Thr Asn Arg Ala Gly Lys Pro Lys Gly Leu Ala Tyr Val Glu Tyr
        835                 840                 845

Glu Asn Glu Ser Gln Ala Ser Gln Ala Val Met Lys Met Asp Gly Met
    850                 855                 860

Thr Ile Lys Glu Asn Ile Ile Lys Val Ala Ile Ser Asn Pro Pro Gln
865                 870                 875                 880

Arg Lys Val Pro Glu Lys Pro Glu Thr Arg Lys Ala Pro Gly Gly Pro
                885                 890                 895

Met Leu Leu Pro Gln Thr Tyr Gly Ala Arg Gly Lys Gly Arg Thr Gln
            900                 905                 910

Leu Ser Leu Leu Pro Arg Ala Leu Gln Arg Pro Ser Ala Ala Ala Pro
        915                 920                 925

Gln Ala Glu Asn Gly Pro Ala Ala Ala Pro Ala Val Ala Ala Pro Ala
    930                 935                 940

Ala Thr Glu Ala Pro Lys Met Ser Asn Ala Asp Phe Ala Lys Leu Phe
945                 950                 955                 960

Leu Arg Gly Ala Gly Gly Met Val His His Arg His Arg Ser Ser Ser
                965                 970                 975

Thr Arg Ser Gly Gly Gly Asp Leu Thr Leu Gly Leu Glu Pro Ser Glu
            980                 985                 990

Glu Glu Ala Pro Arg Ser Pro Leu Ala Pro Ser Glu Gly Ala Gly Ser
        995                 1000                1005

Asp Val Phe Asp Gly Asp Leu Gly Met Gly Ala Ala Lys Gly Leu Gln
    1010                1015                1020

Ser Leu Pro Thr His Asp Pro Ser Pro Leu Gln Arg Tyr Ser Glu Asp
1025                1030                1035                1040

Pro Thr Val Pro Leu Pro Ser Glu Thr Asp Gly Tyr Val Ala Pro Leu
                1045                1050                1055

Thr Cys Ser Pro Gln Pro Glu Tyr Val Asn Gln Pro Asp Val Arg Pro
            1060                1065                1070

Gln Pro Pro Ser Pro Arg Glu Gly Pro Leu Pro Ala Ala Arg Pro Ala
        1075                1080                1085

Gly Ala Thr Leu Glu Arg Ala Lys Thr Leu Ser Pro Gly Lys Asn Gly
    1090                1095                1100

Val Val Lys Asp Val Phe Ala Phe Gly Gly Ala Val Glu Asn Pro Glu
1105                1110                1115                1120

Tyr Leu Thr Pro Gln Gly Gly Ala Ala Pro Gln Pro His Pro Pro Pro
```

Ala Phe Ser Pro Ala Phe Asp Asn Leu Tyr Tyr Trp Asp Gln Asp Pro
     1125                1130                1135

Pro Glu Arg Gly Ala Pro Pro Ser Thr Phe Lys Gly Thr Pro Thr Ala
         1140                1145                1150

Glu Asn Pro Glu Tyr Leu Gly Leu Asp Val Pro
     1155                1160             1165

<210> SEQ ID NO 30
<211> LENGTH: 3537
<212> TYPE: DNA
<213> ORGANISM: Artificial Sequence
<220> FEATURE:
<223> OTHER INFORMATION: SART-3-IC

<400> SEQUENCE: 30

| | | | | | |
|---|---|---|---|---|---|
| atggcgactg | cggccgaaac | ctcggcttca | gaacccgagg | ctgagtccaa | ggctgggccc | 60 |
| aaggctgacg | gagaggagga | tgaggttaag | gcggctagga | caaggagaaa | ggtgttatcg | 120 |
| cgggctgtgg | ccgctgcgac | atacaagacc | atggggccag | cgtgggatca | gcaggaggaa | 180 |
| ggcgtgagcg | agagcgatgg | ggatgagtac | gccatggctt | cctccgcgga | gagctccccc | 240 |
| ggggagtacg | agtgggaata | tgacgaagag | gaggagaaaa | accagctgga | gattgagaga | 300 |
| ctggaggagc | agttgtctat | caacgtctat | gactacaact | gccatgtgga | cttgatcaga | 360 |
| ctgctcaggc | tggaagggga | gcttaccaag | gtgaggatgg | cccgccagaa | gatgagtgaa | 420 |
| atctttccct | tgactgaaga | gctctggctg | agtggctgc | atgacgagat | cagcatggcc | 480 |
| caggatggcc | tggacagaga | gcacgtgtat | gacctctttg | agaaagccgt | gaaggattac | 540 |
| atttgtccta | acatttggct | agagtatggc | cagtactcag | ttggtgggat | tggtcagaaa | 600 |
| ggtggccttg | agaaagttcg | ctccgtgttt | gaagggctc | tctcgtctgt | tggtttacat | 660 |
| atgaccaaag | gactcgccct | ctgggaggct | taccgagagt | ttgaaagtgc | gattgtggaa | 720 |
| gctgctcggc | ttgagaaagt | ccacagtctt | ttccggcgac | agttggcgat | cccactctat | 780 |
| gatatggagg | ccacatttgc | agagtatgaa | gaatggtcag | aagacccaat | accagagtca | 840 |
| gtaattcaga | actataacaa | agcactacag | cagctggaga | aatataaacc | ctatgaagaa | 900 |
| gcactgttgc | aggcagaggc | accaaggctg | cagaatatc | aagcatatat | cgattttgag | 960 |
| atgaaaattg | gcgatcctgc | tcgcattcag | ttgatctttg | agcgcgccct | ggtcgagaac | 1020 |
| tgccttgtcc | cagacttatg | gatccgttac | agtcagtacc | tagatcgaca | actgaaagta | 1080 |
| aaggatttgg | ttttatctgt | acataaccgc | gctattagaa | actgcccctg | gacagttgcc | 1140 |
| ttatggagtc | ggtacctctt | ggccatggag | agacatggag | ttgatcatca | agtaatttct | 1200 |
| gtaaccttcg | agaaagcttt | gaatgccggc | ttcatccagg | ccactgatta | tgtggagatt | 1260 |
| tggcaggcat | accttgatta | cctgaggaga | agggttgatt | tcaaacaaga | ctccagtaaa | 1320 |
| gagctggagg | agttgagggc | cgcctttact | cgtgccttgg | agtatctgaa | gcaggaggtg | 1380 |
| gaagagcgtt | tcaatgagag | tggtgatcca | agctgcgtga | ttatgcagaa | ctgggctagg | 1440 |
| attgaggctc | gactgtgcaa | taacatgcag | aaagctcggg | aactctggga | tagcatcatg | 1500 |
| accagaggaa | atgccaagta | cgccaacatg | tggctagagt | attacaacct | ggaaagagct | 1560 |
| catggtgaca | cccagcactg | ccggaaggct | ctgcaccggg | ccgtccagtg | caccagtgac | 1620 |
| tacccagagc | acgtctgcga | agtgttactc | accatggaga | ggacagaagg | ttctttagaa | 1680 |
| gattgggata | tagctgttca | gaaaactgaa | acccgattag | ctcgtgtcaa | tgagcagaga | 1740 |

```
                                 -continued
atgaaggctg cagagaagga agcagcccct gtgcagcaag aagaagaaaa ggctgaacaa    1800
cggaaaagag ctcgggctga aagaaagcg ttaaaaaaga agaaaaagat cagaggccca    1860
gagaagcgcg gagcagatga ggacgatgag aaagagtggg gcgatgatga agaagagcag    1920
ccttccaaac gcagaagggt cgagaacagc atccctgcag ctggagaaac acaaaatgta    1980
gaagtagcag cagggcccgc tgggaaatgt gctgccgtag atgtggagcc cccttcgaag    2040
cagaaggaga aggcagcctc cctgaagagg gacatgccca aggtgctgca cgacagcagc    2100
aaggacagca tcaccgtctt tgtcagcaac ctgccctaca gcatgcagga gccggacacg    2160
aagctcaggc cactcttcga ggcctgtggg gaggtggtcc agatccgacc catcttcagc    2220
aaccgtgggg atttccgagg ttactgctac gtggagttta agaagagaa atcagccctt    2280 caggcactgg agatgaccg gaaaagtgta gaagggaggc caatgtttgt ttcccccctgt    2340 gtggataaga gcaaaaaccc cgattttaag gtgttcaggt acagcacttc cctagagaaa    2400
cacaagctgt tcatctcagg cctgccttc tcctgtacta aagaggaact agaagaaatc    2460
tgtaaggctc atggcaccgt gaaggacctc aggctggtca ccaaccgggc tggcaaacca    2520
aagggcctgg cctacgtgga gtatgaaaat gaatcccagg cgtcgcaggc tgtgatgaag    2580
atggacggca tgactatcaa agagaacatc atcaaagtgg caatcagcaa ccctcctcag    2640
aggaaagttc cagagaagcc agagaccagg aaggcaccag gtggccccat gcttttgccg    2700
cagacatacg gagcgagggg aagggaagg acgcagctgt ctctactgcc tcgtgccctg    2760
cagcgcccaa gtgctgcagc tcctcaggct gagaacggcc ctgccgcggc tcctgcagtt    2820
gccgccccag cagccaccga ggcacccaag atgtccaatg ccgattttgc caagctgttt    2880
ctgagaggcg ctgggggcat ggtccaccac aggcaccgca gctcatctac caggagtggc    2940
ggtggggacc tgacactagg gctggagccc tctgaagagg aggccccag gtctccactg    3000 gcaccctccg aaggggctgg ctccgatgta tttgatggtg acctgggaat ggggcagcc    3060 aagggcctgc aaagcctccc cacacatgac cccagccctc tacagcggta cagtgaggac    3120
cccacagtac ccctgccctc tgagactgat ggctacgttg ccccctgac ctgcagcccc    3180 cagcctgaat atgtgaacca gccagatgtt cggccccagc ccccttcgcc ccgagagggc    3240
cctctgcctg ctgcccgacc tgctggtgcc actctggaaa gggccaagac tctctcccca    3300
gggaagaatg gggtcgtcaa agacgttttt gcctttgggg gtgccgtgga gaaccccgag    3360
tacttgacac cccagggag agctgcccct cagccccacc ctcctcctgc cttcagccca    3420
gccttcgaca acctctatta ctgggaccag gaccaccag agcggggggc tccacccagc    3480
accttcaaag ggacacctac ggcagagaac ccagagtacc tgggtctgga cgtgcca     3537
```